United States Patent
Cheung et al.

(10) Patent No.: US 7,786,127 B2
(45) Date of Patent: Aug. 31, 2010

(54) BENZIMIDAZOLE THIOPHENE COMPOUNDS

(75) Inventors: Mui Cheung, Collegeville, PA (US); Kyle Allen Emmitte, Durham, NC (US); James Michael Salovich, Durham, NC (US)

(73) Assignee: Glaxo SmithKline LLC, Philadelphia, PA (US)

( * ) Notice: Subject to any disclaimer, the term of this patent is extended or adjusted under 35 U.S.C. 154(b) by 225 days.

(21) Appl. No.: 12/065,668

(22) PCT Filed: Aug. 28, 2006

(86) PCT No.: PCT/US2006/033683

§ 371 (c)(1),
(2), (4) Date: Mar. 4, 2008

(87) PCT Pub. No.: WO2007/030361

PCT Pub. Date: Mar. 15, 2007

(65) Prior Publication Data

US 2008/0214567 A1    Sep. 4, 2008

Related U.S. Application Data

(60) Provisional application No. 60/714,337, filed on Sep. 6, 2005, provisional application No. 60/786,244, filed on Mar. 27, 2006.

(51) Int. Cl.
*A61K 31/4184* (2006.01)
*C07D 409/04* (2006.01)
*A61P 35/00* (2006.01)

(52) U.S. Cl. .................. 514/254.06; 544/370

(58) Field of Classification Search ............ None
See application file for complete search history.

(56) References Cited

U.S. PATENT DOCUMENTS 5,990,146 A    11/1999    Boschelli et al.
6,162,804 A    12/2000    Bilodeau et al.

FOREIGN PATENT DOCUMENTS

| WO | 0012089 A | 3/2000 |
|---|---|---|
| WO | 2004014899 A | 2/2004 |
| WO | 2005037827 A | 4/2005 |
| WO | 2005075465 A | 8/2005 |
| WO | 2007087283 A | 8/2007 |

OTHER PUBLICATIONS

N. Lee Harris et al.; World Health Organization Classification of Neoplastic Diseases of the Hematopoietic and Lymphoid Tissues: Report of the Clinical Advisory Committee Meeting -Airlie House, VA, Nov. 1997; J. Clin. Oncology; Dec. 1999; 17(12); 3838-3849; American Soc. of Clin. Onc.

M. Whitfield et al.; Common Markers of Proliferation; Nature Reviews, Cancer; Feb. 2006; 6; 99-106; Nature Publishing Group.

J. Chan; The New World Health Organization Clasification of Lymphomas: The Past, The Present and The Future; Hematological Oncology; Jul. 2001; 19; 129-150; John Wiley & Sons Ltd.

D.M. Glover et al.; Polo-Like Kinases: A Team That Plays Throughout Mitosis; Genes & Development; 1998; 12; 3777-3787.

D.R. Buckle et al.; Novel 1H-Benzimidazol-4-ols with Potent 5-Lipoxygenase Inhibitory Activity; J. Med. Chem.; 1987; 30; 2216-2221.

C. Corral et al.; Reactions of Methyl 3-Hydroxythiophene-2-carboxylate. Part 4. Synthesis of Methyl 5-Azolyl-3-hydroxythiopene-2-carboxylates; J. Het Chem; Sep. 1987; 24; 1301.

M.M. Donaldson et al.; The Mitotic Roles of Polo-Like Kinase; Journal of Cell Science; 2001; 114(13); 2357-2358.

M. Cheung; "Discovery of Novel Polo-like Kinase 1 (PLK-1) Inhibitors"; Natural Products Gordon Research Conference.; Jul. 22-27, 2007.

K. Kuntz; "Discovery of GSK461364A"; 2007 AACR Annual Meeting; Apr. 17, 2007; 870-873.

Tarasov et al.; Reaction of 1-(ortho-Aminophenyl)-1,2,3-triazole-5-thiols with cyclizing reagents; Russian J of Org Chem; 2004; 40/6; 870-873.

K.Kuntz; "Identification of GSK461364, a novel small molecule polo-like kinase 1 inhibitor for the treatment of cancer" (website abstract); 2007 AACR Annual Meeting; Apr. 2007.

J. Gray; "An Integrated Genomics Approach to Development of Marker Guided Therapy"; 2007 AACR Annual Meeting.; Apr. 10, 2007.

B. Weber; "Genomic Approaches to Targeted Cancer Drug Development"; Presentation to Penn. Univ.; Feb. 7, 2007.

S. Erskine et al.; "Biochemical Characterization of a Novel, Potent, and Selective Inhibitor of Polo-Like Kinase-1 (PLK1)"; 2007 AACR Annual Meeting; Apr. 14-18, 2007.

S. Erskine et al.; "Biochemical Characterization of a Novel, Potent, and Selective Inhibitor of Polo-Like Kinase-1 (PLK1)"; 2007 AACR Annual Meeting (meeting abstract); Apr. 14-18, 2007.

D. Sutton et al.; "Efficacy of GSK461364, a selective Plk1 inhibitor, in Human Tumor Xenograft Models"; 2007 AACR Annual Meeting (poster); Apr. 14-18, 2007.

S. Laquerre et al.; "A potent and selected Polo-like Kinase 1 (PLK1) inhibitor (GSK461364) Induces Cell Cycle Arrest and Growth Inhibition of Cancer Cell"; 2007 AACR Annual Meeting (poster); Apr. 2007.

*Primary Examiner*—Emily Bernhardt
(74) *Attorney, Agent, or Firm*—Robert H. Brink

(57) ABSTRACT

The present invention provides benzimidazole thiophene compounds, pharmaceutical compositions containing the same, and their use as pharmaceutical agents.

8 Claims, No Drawings

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: His-tag for PLK kinase domain

<400> SEQUENCE: 1

Met Lys Lys Gly His His His His His His Asp
 1               5                   10

<210> SEQ ID NO 2
<211> LENGTH: 9
<212> TYPE: PRT
<213> ORGANISM: Artificial Sequence
<220> FEATURE:
<223> OTHER INFORMATION: Optimized PLK Peptide Substrate

<400> SEQUENCE: 2

Ser Phe Asn Asp Thr Leu Asp Phe Asp
 1               5
```

BENZIMIDAZOLE THIOPHENE COMPOUNDS

This Application is a 371 Application of PCT Application No. PCT/US2006/033683, filed 28 Aug. 2006, which claims priority to U.S. Provisional Patent Application Ser. Nos. 60/714,337, filed 6 Sep. 2005 and 60/786,244, filed 27 Mar. 2006.

BACKGROUND OF THE INVENTION

The present invention relates to novel benzimidazole thiophene compounds, pharmaceutical formulations comprising these compounds, and the use of these compounds in therapy.

Polo-like kinases ("PLK") are evolutionarily conserved serine/threonine kinases that play critical roles in regulating processes in the cell cycle. PLK plays a role in the entry into and the exit from mitosis in diverse organisms from yeast to mammalian cells. PLK includes PLK1, PLK2, PLK3 and PLK4.

Overexpression of PLK1 appears to be strongly associated with neoplastic cells (including cancers). A published study has shown high levels of PLK1 RNA expression in >80% of lung and breast tumors, with little to no expression in adjacent normal tissue. Several studies have shown correlations between PLK expression, histological grade, and prognosis in several types of cancer. Significant correlations were found between percentages of PLK-positive cells and histological grade of ovarian and endometrial cancer (P<0.001). These studies noted that PLK is strongly expressed in invading endometrial carcinoma cells and that this could reflect the degree of malignancy and proliferation in endometrial carcinoma. Using RT-PCR analysis, PLK overexpression was detected in 97% of esophageal carcinomas and 73% of gastric carcinomas as compared to the corresponding normal tissues. Further, patients with high levels of PLK overexpression in esophageal carcinoma represented a significantly poorer prognosis group than those with low levels of PLK overexpression. In head and neck cancers, elevated mRNA expression of PLK1 was observed in most tumors; a Kaplan-Meier analysis showed that those patients with moderate levels of PLK1 expression survived longer than those with high levels of PLK1 expression. Analysis of patients with non-small cell lung carcinoma showed similar outcomes related to PLK1 expression.

PCT Publication No. WO2004/014899 to SmithKline Beecham discloses novel benzimidazole thiophene compounds of formula (I):

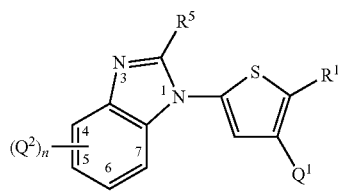

wherein:
$R^1$ is selected from the group consisting of H, alkyl, alkenyl, alkynyl, —C(O)$R^7$, —CO$_2R^7$, —C(O)N$R^7R^8$, —C(O)N($R^7$)O$R^8$, —C(O)N($R^7$)—$R^2$—O$R^8$, —C(O)N($R^7$)-Ph, —C(O)N($R^7$)—$R^2$-Ph, —C(O)N($R^7$)C(O)$R^8$, —C(O)N($R^7$)CO$_2R^8$, —C(O)N($R^7$)C(O)N$R^7R^8$, —C(O)N($R^7$)S(O)$_2R^8$, —$R^2$—O$R^7$, —$R^2$—O—C(O)$R^7$, —C(S)$R^7$, —C(S)N$R^7R^8$, —C(S)N($R^7$)-Ph, —C(S)N($R^7$)—$R^2$-Ph, —$R^2$—S$R^7$, —C(=N$R^7$)N$R^7R^8$, —C(N$R^7$)N($R^8$)-Ph, —C(=N$R^7$)N($R^8$)—$R^2$-Ph, —$R^2$—N$R^7R^8$, —CN, —O$R^7$, —S(O)$_fR^7$, —S(O)$_2$N$R^7R^8$, —S(O)$_2$N($R^7$)-Ph, —S(O)$_2$N($R^7$)—$R^2$-Ph, —N$R^7R^8$, N($R^7$)-Ph, —N($R^7$)—$R^2$-Ph, —N($R^7$)—SO$_2R^8$ and Het;

Ph is phenyl optionally substituted from 1 to 3 times with a substituent selected from the group consisting of halo, alkyl, —OH, —$R^2$—OH, —O-alkyl, —$R^2$—O-alkyl, —NH$_2$, —N(H)alkyl, —N(alkyl)$_2$, —CN and —N$_3$;

Het is a 5-7 membered heterocycle having 1, 2, 3 or 4 heteroatoms selected from N, O and S, or a 5-6 membered heteroaryl having 1, 2, 3 or 4 heteroatoms selected from N, O and S, each optionally substituted from 1 to 2 times with a substituent selected from the group consisting of halo, alkyl, oxo, —OH, —$R^2$—OH, —O-alkyl, —$R^2$—O-alkyl, —NH$_2$, —N(H)alkyl, —N(alkyl)$_2$, —CN and —N$_3$;

$Q^1$ is a group of formula: —$(R^2)_a$—$(Y^1)_b$—$(R^2)_c$—$R^3$ a, b and c are the same or different and are each independently 0 or 1 and at least one of a or b is 1;

n is 0, 1, 2, 3 or 4;

$Q^2$ is a group of formula: —$(R^2)_{aa}$—$(Y^2)_{bb}$—$(R^2)_{cc}$—$R^4$ or two adjacent $Q^2$ groups are selected from the group consisting of alkyl, alkenyl, —O$R^7$, —S(O)$_fR^7$ and —N$R^7R^8$ and together with the carbon atoms to which they are bound, they form a $C_{5-6}$cycloalkyl, $C_{5-6}$cycloalkenyl, phenyl, 5-7 membered heterocycle having 1 or 2 heteroatoms selected from N, O and S, or 5-6 membered heteroaryl having 1 or 2 heteroatoms selected from N, O and S;

aa, bb and cc are the same or different and are each independently 0 or 1;

each $Y^1$ and $Y^2$ is the same or different and is independently selected from the group consisting of —O—, —S(O)$_f$—, —N($R^7$)—, —C(O)—, —OC(O)—, —CO$_2$—, —C(O)N($R^7$)—, —C(O)N($R^7$)S(O)$_2$—, —OC(O)N($R^7$)—, —OS(O)$_2$—, —S(O)$_2$N($R^7$)—, —S(O)$_2$N($R^7$)C(O)—, —N($R^7$)S(O)$_2$—, —N($R^7$)C(O)—, —N($R^7$)CO$_2$— and —N($R^7$)C(O)N($R^7$)—;

each $R^2$ is the same or different and is independently selected from the group consisting of alkylene, alkenylene and alkynylene;

each $R^3$ and $R^4$ is the same or different and is each independently selected from the group consisting of H, halo, alkyl, alkenyl, alkynyl, —C(O)$R^7$, —C(O)N$R^7R^8$, —CO$_2R^7$, —C(S)$R^7$, —C(S)N$R^7R^8$, —C(=N$R^7$)$R^8$, —C(=N$R^7$)N$R^7R^8$, —C$R^7$=N—O$R^7$, —O$R^7$, —S(O)$_fR^7$, —S(O)$_2$N$R^7R^8$, —N$R^7R^3$, —N($R^7$)C(O)$R^8$, —N($R^7$)S(O)$_2R^8$, —NO$_2$, —CN, —N$_3$ and a group of formula (ii):

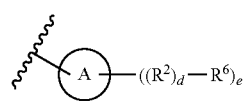

wherein:
Ring A is selected from the group consisting of $C_{5-10}$cycloalkyl, $C_{5-10}$cycyloalkenyl, aryl, 5-10 membered heterocycle having 1, 2 or 3 heteroatoms selected from N, O and S and 5-10 membered heteroaryl having 1, 2 or 3 heteroatoms selected from N, O and S each d is 0 or 1;

e is 0, 1, 2, 3 or 4;

each $R^6$ is the same or different and is independently selected from the group consisting of H, halo, alkyl, alkenyl, alkynyl, cycloalkyl, cycloalkenyl, Ph, Het, —CH(OH)—R²—OH, —C(O)R⁷, —CO₂R⁷, —CO₂—R₂-Ph, —CO₂—R²—Het, —C(O)NR⁷R⁸, —C(O)N(R⁷)C(O)R⁷, —C(O)N(R⁷)CO₂R⁷, —C(O)N(R⁷)C(O)NR⁷R⁸, —C(O)N(R⁷)S(O)₂R⁷, —C(S)R⁷, —C(S)NR⁷R⁸, —C(=NR⁷)R⁸, —C(=NR⁷)NR⁷R⁸, —CR⁷=N—OR⁸, =O, —OR⁷, —OC(O)R⁷, —OC(O)Ph, —OC(O)Het, —OC(O)NR⁷R⁸, —O—R²—S(O)₂R⁷, —S(O)ᵢR⁷, —S(O)₂NR⁷R⁸, —S(O)₂Ph, —S(O)₂Het, —NR⁷R⁸, —N(R⁷)C(O)R⁸, —N(R⁷)CO₂R⁸, —N(R⁷)—R²—CO₂R⁸, —N(R⁷)C(O)NR⁷R⁸, —N(R⁷)—R²—C(O)NR⁷R⁸, —N(R⁷)C(O)Ph, —N(R⁷)C(O)Het, —N(R⁷)Ph, —N(R⁷)Het, —N(R⁷)C(O)NR⁷—R²—NR⁷R⁸, —N(R⁷)C(O)N(R⁷)Ph, —N(R⁷)C(O)N(R⁷)Het, —N(R⁷)C(O)N(R⁷)—R²—Het, —N(R⁷)S(O)₂R⁸, —N(R⁷)—R²—S(O)₂R⁸, —NO₂, —CN and —N₃;

wherein when Q¹ is defined where b is 1 and c is 0, R³ is not halo, —C(O)R⁷, —C(O)NR⁷R⁸, —CO₂R⁷, —C(S)R⁷, —C(S)NR⁷R⁸, —C(=NR⁷)R⁸, —C(=NR⁷)NR⁷R⁸, —CR⁷=N—OR⁷—OR⁷, —S(O)ᵢR⁷, —S(O)₂NR⁷R⁸, —NR⁷R⁸, —N(R⁷)C(O)R⁸, —N(R⁷)S(O)₂R⁸, —NO₂, —CN or —N₃;

wherein when Q² is defined where bb is 1 and cc is 0, R⁴ is not halo, —C(O)R⁷, —C(O)NR⁷R⁸, —CO₂R⁷, —C(S)R⁷, —C(S)NR⁷R⁸, —C(=NR⁷)R⁸, —C(=NR⁷)NR⁷R⁸, —CR⁷=N—OR⁷, —OR, —S(O)ᵢR⁷, —S(O)₂NR⁷R⁸, —NR⁷R⁸, —N(R⁷)C(O)R⁸, —N(R⁷)S(O)₂R⁸, —NO₂, —CN or —N₃;

R⁵ is selected from the group consisting of H, halo, alkyl, cycloalkyl, OR⁷, —S(O)ᵢR⁷, —NR⁷R⁸, —NHC(O)R⁷, —NHC(O)NR⁷R⁸ and —NHS(O)₂R⁷;

f is 0, 1 or 2; and each R⁷ and each R⁸ are the same or different and are each independently selected from the group consisting of H, alkyl, alkenyl, alkynyl, cycloalkyl and cycloalkenyl;

wherein when R¹ is —CO₂CH₃ and n is 0, Q¹ is not —OH;

or a pharmaceutically acceptable salt, solvate or physiologically functional derivative thereof.

Also disclosed are pharmaceutical compositions containing these compounds, processes for their preparation and methods for treatment of conditions mediated by PLK using these compounds.

BRIEF SUMMARY OF THE INVENTION

According to a first aspect of the invention there is provided a compound selected from:

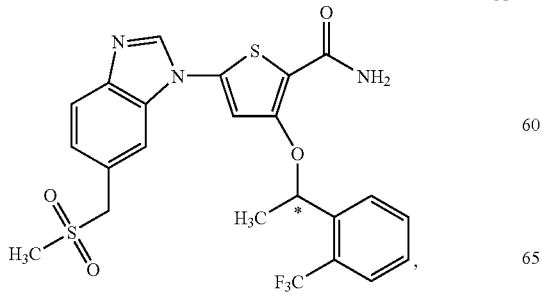
A

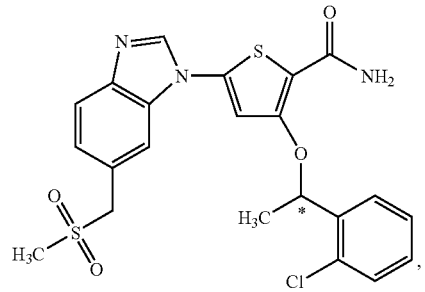
B

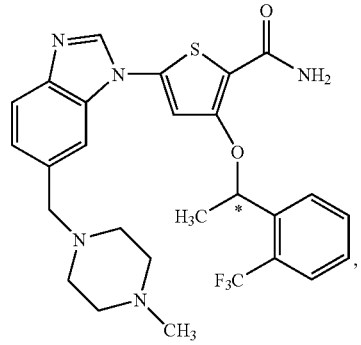
C

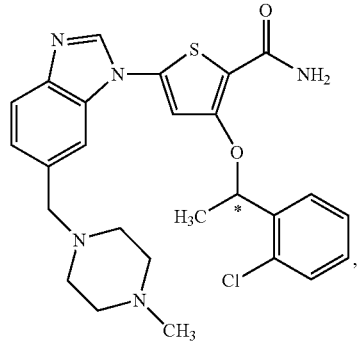
D

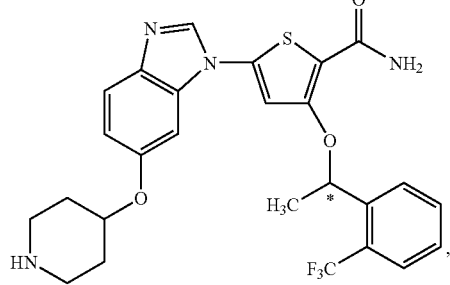
E

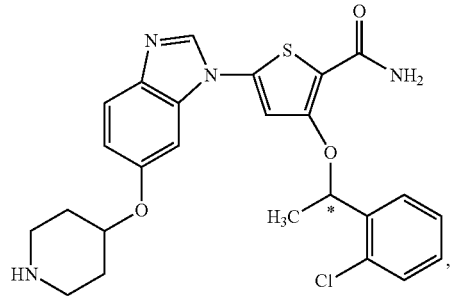
F

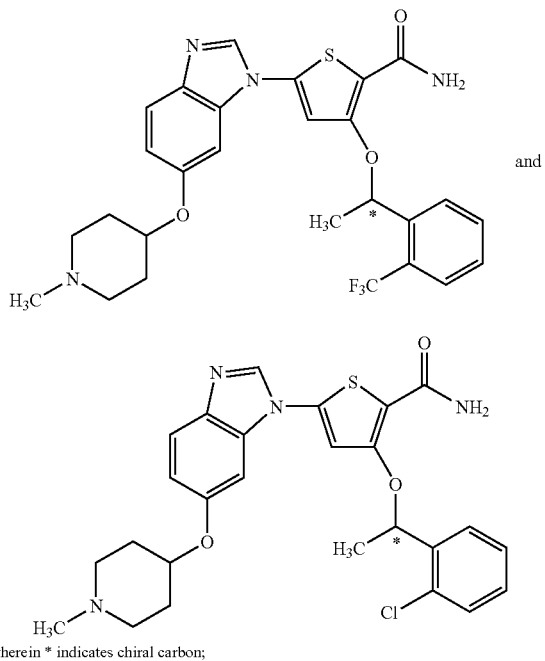

wherein * indicates chiral carbon;

and pharmaceutically acceptable salts or solvates thereof.

In another aspect, there is provided an enantiomerically enriched compound selected from A, B, C, D, E, F, G, and H wherein the stereochemistry of the chiral carbon is R.

In a third aspect of the invention there is provided a pharmaceutical composition comprising a compound selected from A, B, C, D, E, F, G and H and pharmaceutically acceptable salts or solvates thereof. In one embodiment, the pharmaceutical composition further comprises a pharmaceutically acceptable carrier, diluent or excipient.

In a fourth aspect of the invention, there is provided a method for treating a condition mediated by PLK in a mammal in need thereof. The method comprises administering to the mammal a therapeutically effective amount of a compound selected from A, B, C, D, E, F, G and H and pharmaceutically acceptable salts or solvates thereof.

In a fifth aspect of the invention, there is provided a method for treating a susceptible neoplasm in a mammal in need thereof. The method comprises administering to the mammal a therapeutically effective amount of a compound selected from A, B, C, D, E, F, G and H and pharmaceutically acceptable salts or solvates thereof. The susceptible neoplasm may be selected from the group consisting of breast cancer, colon cancer, lung cancer, including small cell lung cancer and non-small cell lung cancer, prostate cancer, endometrial cancer, gastric cancer, melanoma, ovarian cancer, pancreatic cancer, squamous cell carcinoma, carcinoma of the head and neck, esophageal carcinoma, hepatocellular carcinoma, and hematologic malignancies, such as acute leukemias and aggressive lymphomas.

In a sixth aspect of the invention, there is provided a method for treating a breast cancer in a mammal in need thereof. The method comprises administering to the mammal a therapeutically effective amount of a compound selected from A, B, C, D, E, F, G and H and pharmaceutically acceptable salts or solvates thereof.

In a seventh aspect of the invention, there is provided a method for treating ovarian cancer in a mammal in need thereof. The method comprises administering to the mammal a therapeutically effective amount of a compound selected from A, B, C, D, E, F, G and H and pharmaceutically acceptable salts or solvates thereof.

In a eighth aspect of the invention, there is provided a method for treating non-small cell lung cancer in a mammal in need thereof. The method comprises administering to the mammal a therapeutically effective amount of a compound selected from A, B, C, D, E, F, G and H and pharmaceutically acceptable salts or solvates thereof.

In a ninth aspect of the invention, there is provided a method for treating prostate cancer in a mammal in need thereof. The method comprises administering to the mammal a therapeutically effective amount of a compound selected from A, B, C, D, E, F, G and H and pharmaceutically acceptable salts or solvates thereof.

In a tenth aspect of the invention, there is provided a method for treating a hematologic malignancy in a mammal in need thereof. The method comprises administering to the mammal a therapeutically effective amount of a compound selected from A, B, C, D, E, F, G and H and pharmaceutically acceptable salts or solvates thereof.

In another aspect of the invention, there is provided a method for treating a condition characterized by inappropriate cellular proliferation. The method comprises contacting the cell with a therapeutically effective amount of a compound selected from A, B, C, D, E, F, G and H and pharmaceutically acceptable salts or solvates thereof.

In another aspect, the present invention provides a method for inhibiting proliferation of a cell. The method comprises contacting the cell with an amount of a compound selected from A, B, C, D, E, F, G and H and pharmaceutically acceptable salts or solvates thereof.

In another aspect, the present invention provides a method for inhibiting mitosis in a cell. The method comprises administering to the cell an amount of a compound selected from A, B, C, D, E, F, G and H and pharmaceutically acceptable salts or solvates thereof.

In another aspect, the present invention provides a compound selected from A, B, C, D, E, F, G and H and pharmaceutically acceptable salts or solvates thereof for use in therapy.

In yet another aspect, the present invention provides a compound selected from A, B, C, D, E, F, G and H and pharmaceutically acceptable salts or solvates thereof for use in the treatment of a condition mediated by PLK in a mammal in need thereof.

In yet another aspect, the present invention provides a compound selected from A, B, C, D, E, F, G and H and pharmaceutically acceptable salts or solvates thereof for use in the treatment of a susceptible neoplasm in a mammal.

In yet another aspect, the present invention provides a compound selected from A, B, C, D, E, F, G and H and pharmaceutically acceptable salts or solvates thereof for use in the treatment of breast cancer, ovarian cancer, non-small cell lung cancer, prostate cancer, or a hematologic malignancy in a mammal.

In another aspect, the present invention provides a compound selected from A, B, C, D, E, F, G and H and pharmaceutically acceptable salts or solvates thereof for use in the treatment of a condition characterized by inappropriate cellular proliferation.

In yet another aspect, the present invention provides a compound selected from A, B, C, D, E, F, G and H and pharmaceutically acceptable salts or solvates thereof for use in inhibiting proliferation of a cell.

In yet another aspect, the present invention provides a compound selected from A, B, C, D, E, F, G and H and pharmaceutically acceptable salts or solvates thereof for use in inhibiting mitosis in a cell.

In yet another aspect, the present invention provides the use of a compound selected from A, B, C, D, E, F, G and H and pharmaceutically acceptable salts or solvates thereof for the preparation of a medicament for the treatment of condition mediated by PLK in a mammal.

In yet another aspect, the present invention provides the use of a compound selected from A, B, C, D, E, F, G and H and pharmaceutically acceptable salts or solvates thereof for the preparation of a medicament for the treatment of a susceptible neoplasm in a mammal.

In yet another aspect, the present invention provides the use of a compound selected from A, B, C, D, E, F, G and H and pharmaceutically acceptable salts or solvates thereof for the preparation of a medicament for the treatment of a breast cancer, ovarian cancer, non-small cell lung cancer, prostate cancer, or a hematologic malignancy in a mammal.

In yet another aspect, the present invention provides the use of a compound selected from A, B, C, D, E, F, G and H and pharmaceutically acceptable salts or solvates thereof for the preparation of a medicament for the treatment of a condition characterized by inappropriate cellular proliferation in a mammal.

In yet another aspect, the present invention provides the use of a compound selected from A, B, C, D, E, F, G and H and pharmaceutically acceptable salts or solvates thereof for the preparation of a medicament for inhibiting proliferation of a cell.

In yet another aspect, the present invention provides the use of a compound selected from A, B, C, D, E, F, G and H and pharmaceutically acceptable salts or solvates thereof for the preparation of a medicament for inhibiting mitosis in a cell.

In yet another aspect, the present invention provides a pharmaceutical composition comprising a compound selected from A, B, C, D, E, F, G and H and pharmaceutically acceptable salts or solvates thereof for use in the treatment of a susceptible neoplasm, such as breast cancer, ovarian cancer, non-small cell lung cancer, prostate cancer, and hematologic malignancies, in a mammal.

DETAILED DESCRIPTION OF THE INVENTION

As used herein, "compound(s) of the invention" or "compound(s) selected from A, B, C, D, E, F, G and H" means compound(s) selected from A, B, C, D, E, F, G and H, or enantiomerically enriched compound(s) selected from A, B, C, D, E, F, G and H, or a pharmaceutically acceptable salt or solvate thereof.

As used herein, "compound(s) selected from A-1, B-1, C-1, D-1, E-1, F-1, G-1 and H-1" means compound(s) selected from A-1, B-1, C-1, D-1, E-1, F-1, G-1 and H-1 or a pharmaceutically acceptable salt or solvate thereof.

As used herein, the term "optionally" means that the subsequently described event(s) may or may not occur, and includes both event(s) that occur and events that do not occur.

Compounds of the invention exist in stereoisomeric forms (e.g. they contain one or more chiral or asymmetric carbon atoms). The term "chiral" refers to a molecule that is not superimposable on its mirror image. The term "achiral" refers to a molecule that is superimposable on its mirror image.

The term "stereoisomers" refers to compounds which are have a common chemical constitution but differ in the arrangement of the atoms or groups in space. Stereoisomers may be optical isomers or geometric isomers. Optical isomers include both enantiomers and diastereomers. An "enantiomer" is one of a pair of optical isomers containing a chiral carbon atom whose molecular configuration have left- and right-hand (chiral) forms. That is, "enantiomer" refers to each of a pair of optical isomers of a compound which are non-superimposable mirror images of one another. A "diastereomer" is one of a pair of optical isomers of a compound with two or more centers of dissymmetry and whose molecules are not mirror images of one another. The nomenclature of a chiral center is governed by the (R)—(S) system. Whether a particular compound is designated as the "R" or "S" enantiomer according to the system depends upon the nature of the atoms or groups which are bound to the chiral carbon.

Enantiomers differ in their behavior toward plane-polarized light, that is, their optical activity. An enantiomer that rotates plane-polarized light in a clockwise direction is said to be dextrorotatory and is designated by the symbol "d" or "(+)" for positive rotation. An enantiomer that rotates plane-polarized light in the counterclockwise direction is said to be levorotatory and is designated by the symbol "l" or "(−)" for negative rotation. There is no correlation between the configuration of enantiomers and the direction in which they rotate plane-polarized light. There is also no necessary correlation between the (R) and (S) designation and the direction of rotation of the plane-polarized light. The optical activity, or direction of rotation of plane-polarized light, of an enantiomer of a compound of the invention may be determined using conventional techniques.

The terms "racemate" and "racemic mixture" as used herein refer to a mixture of the (R)— and the (S)— optical isomers (e.g., enantiomers) of a compound in equal, i.e. 50:50 proportion.

The term "enantiomerically enriched" as used herein refers to preparations comprising a mixture of optical isomers in which the quantity of one enantiomer is higher than the quantity of the other. Thus, "enantiomerically enriched" refers to mixtures of optical isomers wherein the ratio of enantiomer is greater than 50:50. An enantiomerically enriched compound comprises greater than 50% by weight of one enantiomer relative to the other. For example enantiomerically enriched 5-{6-[(Methylsulfonyl)methyl]-1H-benzimidazol-1-yl}-3-({(1R)-1-[2-(trifluoromethyl)phenyl]ethyl}oxy)-2-thiophenecarboxamide refers to a composition comprising greater than 50% by weight of the (R)-enantiomer relative to the (S)-enantiomer of the compound. In one embodiment, an enantiomerically enriched compound comprises at least 75% by weight of one enantiomer relative to the other. In another embodiment, an enantiomerically enriched compound comprises at least 80% by weight of one enantiomer relative to the other. In one particular embodiment, an enantiomerically enriched compound comprises at least 85% by weight of one enantiomer relative to the other.

The term "enantiomerically pure" as used herein refers to enantiomerically enriched compounds comprising at least 90% by weight of one enantiomer relative to the other. In one embodiment, an enantiomerically pure compound comprises at least 95% by weight of one enantiomer relative to the other. In one particular embodiment, an enantiomerically pure compound comprises at least 99% by weight of one enantiomer relative to the other.

The present invention provides compounds selected from:

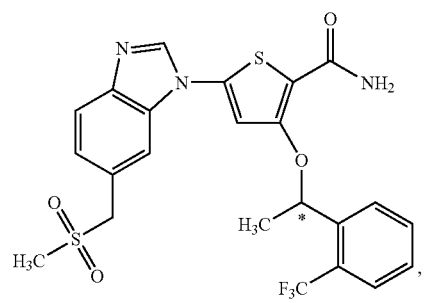
A

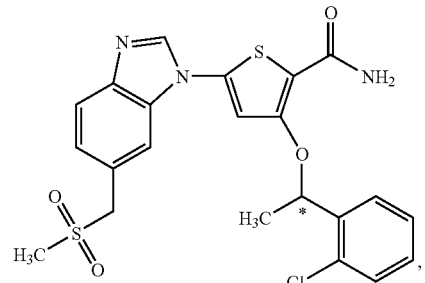
B

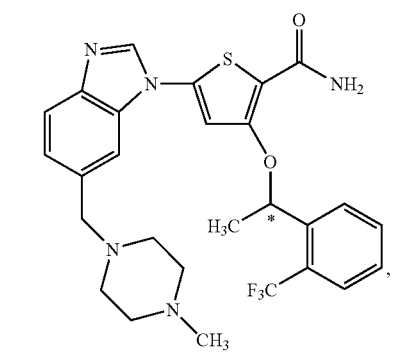
C

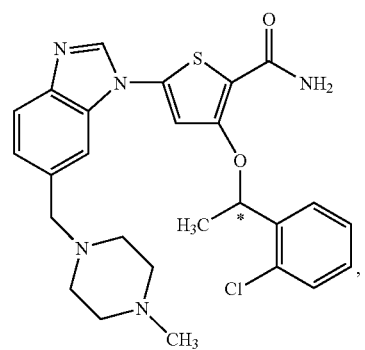
D

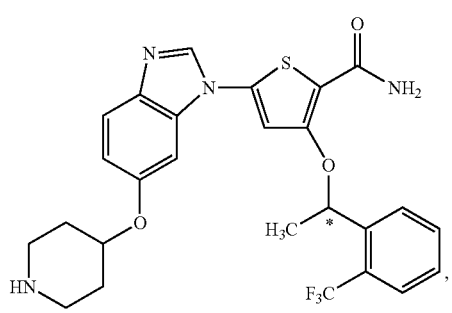
E

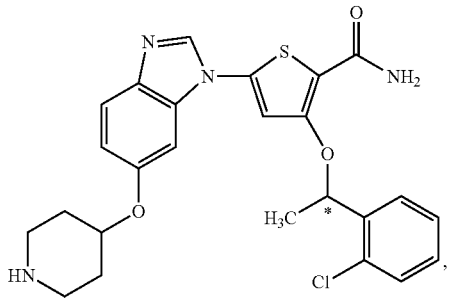
F

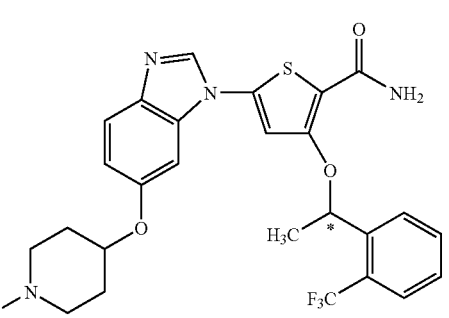
G

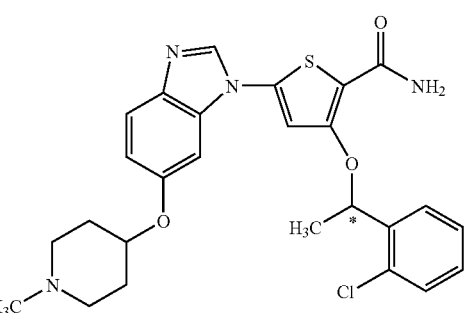
H wherein * indicates chiral carbon;

and pharmaceutically acceptable salts and solvates thereof.

In one particular embodiment, the compounds A, B, C, D, E, F, G and H are enantiomerically enriched, wherein the stereochemistry of the chiral carbon is R. In another embodiment the compounds A, B, C, D, E, F, G and H are enantiomerically pure, wherein the stereochemistry of the chiral carbon is R.

Thus, in one preferred embodiment, the present invention provides enantiomerically enriched and enantiomerically pure compounds selected from:

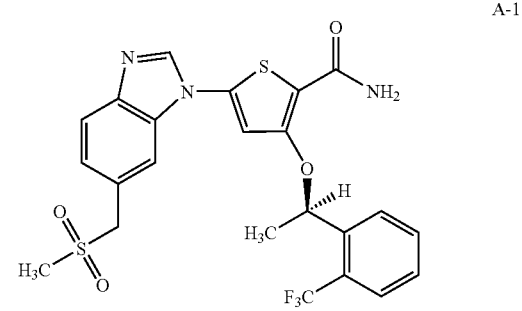
A-1

5-{6-[(Methylsulfonyl)methyl]-1H-benzimidazol-1-yl}-3-({(1R)-1-[2-(trifluoromethyl)phenyl]-ethyl}oxy)-2-thiophenecarboxamide;

3-{[(1R)-1-(2-Chlorophenyl)ethyl]oxy}-5-{6-[(4-methylpiperazin-1-yl)methyl]-1H-benzimidazol-1-yl}thiophene-2-carboxamide;

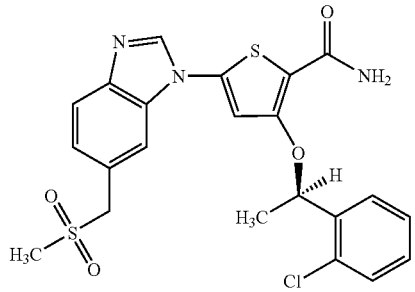

B-1

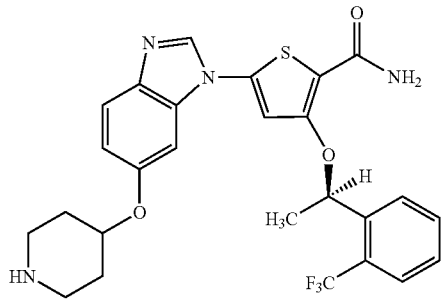

E-1

3-{[(1R)-1-(2-Chlorophenyl)ethyl]oxy}-5-{6-[(methylsulfonyl)methyl]-1H-benzimidazol-1-yl}-2-thiophenecarboxamide;

5-[6-(4-Piperidinyloxy)-1H-benzimidazol-1-yl]-3-({(1R)-1-[2-(trifluoromethyl)phenyl]ethyl}oxy)-2-thiophenecarboxamide;

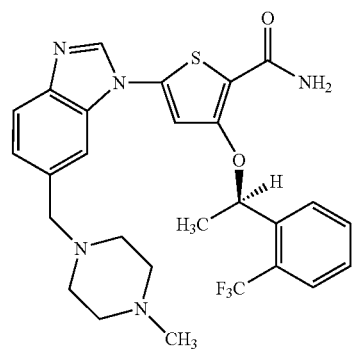

C-1

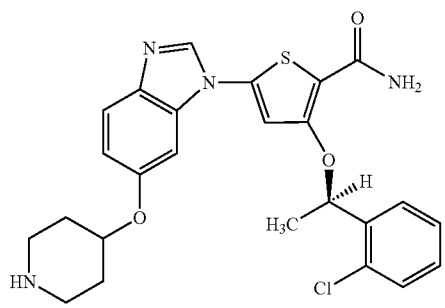

F-1

5-{6-[(4-Methylpiperazin-1-yl)methyl]-1H-benzimidazol-1-yl}-3-{(1R)-1-[2-(trifluoromethyl)phenyl]ethoxy}thiophene-2-carboxamide;

3-{[(1R)-1-(2-Chlorophenyl)ethyl]oxy}-5-[6-(4-piperidinyloxy)-1H-benzimidazol-1-yl]-2-thiophenecarboxamide;

D-1

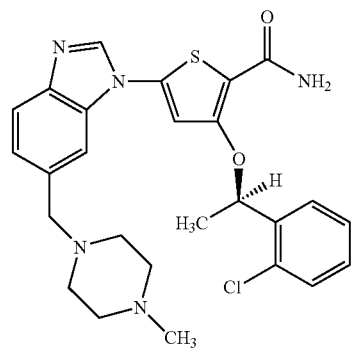

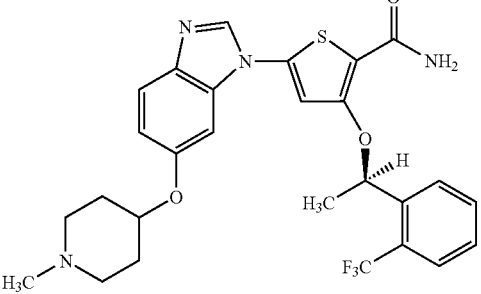

G-1

5-{6-[(1-Methyl-4-piperidinyl)oxy]-1H-benzimidazol-1-yl}-3-({(1R)-1-[2-(trifluoromethyl)phenyl]ethyl}oxy)-2-thiophenecarboxamide; and

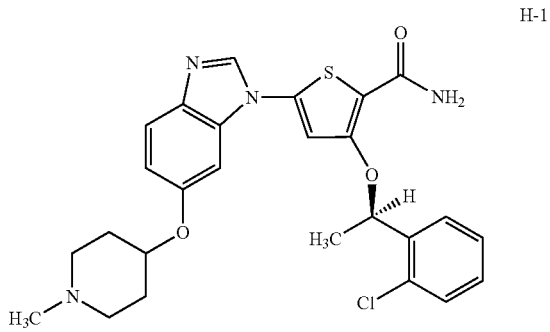

H-1

3-{[(1R)-1-(2-Chlorophenyl)ethyl]oxy}-5-{6-[(1-methyl-4-piperidinyl)oxy]-1H-benzimidazol-1-yl}-2-thiophenecarboxamide;

and pharmaceutically acceptable salts and solvates thereof.

It will be appreciated by those skilled in the art that the compounds of the present invention may be utilized in the form of a pharmaceutically acceptable salt or solvate thereof. The pharmaceutically acceptable salts of the compounds of the present invention (or the enantiomerically enriched or pure forms thereof) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic (mesylate), naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. Specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of the invention or an enaniomerically enriched or pure form thereof) and a solvent. Solvents, by way of example, include water, methanol, ethanol, or acetic acid.

Processes for preparing pharmaceutically acceptable salts and solvates of the compounds of the invention are conventional in the art. See, e.g., Burger's Medicinal Chemistry And Drug Discovery 5th Edition, Vol 1: Principles And Practice.

As will be apparent to those skilled in the art, in the processes described below for the preparation of the compounds of the invention, certain intermediates, may alternatively be in the form of pharmaceutically acceptable salts or solvates of the compound. Those terms as applied to any intermediate employed in the process of preparing the compounds of the invention have the same meanings as noted above with respect to the compounds of the invention. Processes for preparing pharmaceutically acceptable salts and solvates of such intermediates are known in the art and are analogous to the process for preparing pharmaceutically acceptable salts and solvates of the compounds of the invention.

The compounds of the present invention are typically inhibitors of PLK. By PLK inhibitor is meant a compound which exhibits $pIC_{50}$ greater than 6 in the PLK Inhibition assay described below in the examples or an $IC_{50}$ less than 10 µM in the Methylene Blue or Cell-Titre Glo Growth Inhibition assay described below in the examples; more particularly a PLK inhibitor is a compound which exhibits a $pIC_{50}$ greater than 7 or an $IC_{50}$ less than 1 µM using the methods described in the examples below.

The present invention further provides compounds of the invention for use in medical therapy in an animal, e.g. a mammal such as a human. In particular, the present invention provides compounds for use in the treatment of a condition mediated by PLK. The present invention also provides compounds for use in the treatment of a susceptible neoplasm. The term "susceptible neoplasm" is defined below. In particular, the present invention provides compounds for use in the treatment of a variety of solid tumors including but not limited to breast cancer, ovarian cancer, non-small cell lung cancer prostate cancer, and hematologic malignancies including but not limited to acute (myeloid and lymphoid) leukemias and aggressive lymphomas.

The present invention provides compounds for use in treating a condition characterized by inappropriate cellular proliferation. The present invention also provides compounds for use in inhibiting proliferation of a cell. The present invention also provides compounds for use in inhibiting mitosis in a cell.

The present invention provides methods for the treatment of several conditions or diseases, all of which comprise the step of administering a therapeutically effective amount of a compound of the invention. As used herein, the term "treatment" refers to alleviating the specified condition, eliminating or reducing the symptoms of the condition, slowing or eliminating the progression of the condition and preventing or delaying the reoccurrence of the condition in a previously afflicted subject.

As used herein, the term "therapeutically effective amount" means an amount of a compound of the invention which is sufficient, in the subject to which it is administered, to elicit the biological or medical response of a cell culture, tissue, system, animal (including human) that is being sought, for instance, by a researcher or clinician. For example, a therapeutically effective amount of a compound of the invention for the treatment of a condition mediated by PLK is an amount sufficient to treat the PLK mediated condition in the subject. Similarly, a therapeutically effective amount of a compound of the invention for the treatment of a susceptible neoplasm is an amount sufficient to treat the susceptible neoplasm in the subject. In one embodiment of the present invention, the therapeutically effective amount of a compound of the invention is an amount sufficient to inhibit cell mitosis. In one embodiment of the present invention, a therapeutically effective amount of a compound of the invention is an amount sufficient to regulate, modulate, bind or inhibit PLK.

The precise therapeutically effective amount of a compound of the invention will depend on a number of factors including, but not limited to, the age and weight of the subject being treated, the precise disorder requiring treatment and its severity, the nature of the formulation, and the route of administration, and will ultimately be at the discretion of the attendant physician or veterinarian. Typically, a compound of the invention will be given for treatment in the range of 0.1 to 200 mg/kg body weight of recipient (animal) per day or per dose or per cycle of treatment and more usually in the range of 1 to 100 mg/kg body weight per day or per dose or per cycle of treatment. Acceptable dosages, may be from about 0.1 to about 2000 mg per day, dose, or cycle of treatment, and preferably from about 0.1 to about 500 mg per day, dose, or cycle of treatment.

As one aspect, the present invention provides methods of regulating, modulating, binding, or inhibiting PLK for the treatment of conditions mediated by PLK, particularly PLK1. "Regulating, modulating, binding or inhibiting PLK" refers to regulating, modulating, binding or inhibiting PLK, particularly PLK1, activity, as well as regulating, modulating, binding or inhibiting overexpression of PLK, particularly PLK1. Such conditions include certain neoplasms (including cancers and tumors) which have been associated with PLK, particularly PLK1, and conditions characterized by inappropriate cellular proliferation.

The present invention provides a method for treating a condition mediated by PLK, particularly PLK1, which comprises administering to the animal a therapeutically effective amount of the compound of the invention. This method and other methods of the present invention are useful for the treatment of an animal such as a mammal and in particular humans. Conditions which are mediated by PLK are known in the art and include but are not limited to neoplasms and conditions characterized by inappropriate cellular proliferation.

The present invention also provides a method for treating a susceptible neoplasm (cancer or tumor) in an animal such as a mammal (e.g., a human) in need thereof, which method comprises administering to the animal a therapeutically effective amount of the compound of the invention. "Susceptible neoplasm" as used herein refers to neoplasms which are susceptible to treatment with a PLK inhibitor. Neoplasms which have been associated with PLK and are therefore susceptible to treatment with a PLK inhibitor are known in the art, and include both primary and metastatic tumors and cancers. For example, susceptible neoplasms within the scope of the present invention include but are not limited to breast cancer, colon cancer, lung cancer (including small cell lung cancer and non-small cell lung cancer), prostate cancer, endometrial cancer, gastric cancer, melanoma, ovarian cancer, pancreatic cancer, squamous cell carcinoma, carcinoma of the head and neck, esophageal carcinoma, hepatocellular carcinoma, and hematologic malignancies including but not limited to acute leukemias and aggressive lymphomas. In one particular embodiment, the present invention provides a method of treating breast cancer in an animal, such as a mammal (e.g., a human) in need thereof by administering a therapeutically effective amount of a compound of the present invention. In another particular embodiment, the present invention provides a method of treating ovarian cancer in an animal, such as a mammal (e.g., a human) in need thereof by administering a therapeutically effective amount of a compound of the present invention. In another particular embodiment, the present invention provides a method of treating non-small cell lung cancer in an animal, such as a mammal (e.g., a human) in need thereof by administering a therapeutically effective amount of a compound of the present invention. In another particular embodiment, the present invention provides a method of treating prostate cancer in an animal, such as a mammal (e.g., a human) in need thereof by administering a therapeutically effective amount of a compound of the present invention. In another particular embodiment, the present invention provides a method of treating acute leukemia, including acute myeloid leukemia and acute lymphoid leukemia, in an animal, such as a mammal (e.g., a human) in need thereof by administering a therapeutically effective amount of a compound of the present invention. In another particular embodiment, the present invention provides a method of treating aggressive lymphoma in an animal, such as a mammal (e.g., a human) in need thereof by administering a therapeutically effective amount of a compound of the present invention.

The compounds of the invention can be used alone in the treatment of such susceptible neoplasms or can be used to provide additive or synergistic effects with one or more other compounds of the invention, or in combination with certain existing chemotherapies and/or other anti-neoplastic therapies. In addition, the compounds of the invention can be used to restore effectiveness of one or more other compounds of the invention, certain existing chemotherapies and/or other anti-neoplastic therapies. As used herein, "anti-neoplastic therapies" includes but is not limited to cytotoxic chemotherapy, hormonal therapy, targeted kinase inhibitors, therapeutic monoclonal antibodies, surgery and radiation therapy.

The present invention also provides a method for treating a condition characterized by inappropriate cellular proliferation in an animal, such as a mammal (e.g., a human) in need thereof. The method comprises administering a therapeutically effective amount of a compound of the present invention. By "inappropriate cellular proliferation" is meant cellular proliferation resulting from inappropriate cell growth, cellular proliferation resulting from excessive cell division, cellular proliferation resulting from cell division at an accelerated rate, cellular proliferation resulting from inappropriate cell survival, and/or cellular proliferation in a normal cell occurring at a normal rate, which is nevertheless undesired. Conditions characterized by inappropriate cellular proliferation include but are not limited to neoplasms, blood vessel proliferative disorders, fibrotic disorders, mesangial cell proliferative disorders and inflammatory/immune-mediated diseases. Blood vessel proliferative disorders include arthritis and restenosis. Fibrotic disorders include hepatic cirrhosis and atherosclerosis. Mesangial cell proliferative disorders include glomerulonephritis, malignant nephrosclerosis, and glomerulopathies. Inflammatory/immune-mediated disorders include psoriasis, chronic wound healing, organ transplant rejection, thrombotic microangiopathy syndromes and neurodegenerative diseases. Osteoarthritis and other osteoclast proliferation dependent diseases of excess bone resorbtion are examples of conditions characterized by inappropriate cellular proliferation in which the cellular proliferation occurs in normal cells at a normal rate, but is nevertheless undesired.

The present invention also provides a method for inhibiting proliferation of a cell, which method comprises contacting the cell with an amount of a compound of the invention sufficient to inhibit proliferation of the cell. In one particular embodiment, the cell is a neoplastic cell. In one particular embodiment, the cell is an inappropriately proliferative cell. The term "inappropriately proliferative cell" as used herein refers to cells that grow inappropriately (abnormally), cells that divide excessively or at an accelerated rate, cells that inappropriately (abnormally) survive and/or normal cells that proliferate at a normal rate but for which proliferation is undesired. Neoplastic cells (including cancer cells) are an example of inappropriately proliferative cells but are not the only inappropriately proliferative cells.

PLK is essential for cellular mitosis and accordingly, the compounds of the invention are believed to be effective for inhibiting mitosis. "Inhibiting mitosis" refers to inhibiting the entry into the M phase of the cell cycle, inhibiting the normal progression of the M phase of the cell cycle once M phase has been entered and inhibiting the normal exit from the M phase of the cell cycle. Thus, the compounds of the present invention may inhibit mitosis by inhibiting the cell's entry into mitosis, by inhibiting the cell's progression through mitosis or by inhibiting the cell's exit from mitosis. As one aspect, the present invention provides a method for inhibiting mitosis in a cell, which method comprises administering to the cell an amount of a compound of the invention sufficient to inhibit mitosis. In one particular embodiment, the cell is a neoplastic cell. In one particular embodiment, the cell is an inappropriately proliferative cell.

The present invention also provides the use of a compound of the invention for the preparation of a medicament for the treatment of condition mediated by PLK in an animal, such as a mammal (e.g., a human). The present invention further provides the use of a compound for the preparation of a medicament for the treatment of a susceptible neoplasm in an animal. In particular, the present invention provides the use of a compound for the preparation of a medicament for the treatment of a breast cancer in an animal. The present invention also provides the use of a compound for the preparation of a medicament for the treatment of ovarian cancer in an animal. The present invention provides the use of a compound for the preparation of a medicament for the treatment of non-small cell lung cancer in an animal. The present invention also provides the use of a compound for the preparation of a medicament for the treatment of prostate cancer in an animal. The present invention provides the use of a compound for the preparation of a medicament for the treatment of acute leukemia (including acute myeloid and acute lymphoid leukemia) in an animal. The present invention provides the use of a compound for that the preparation of a medicament for the treatment of aggressive lymphoma in an animal. The present invention further provides the use of a compound for the preparation of a medicament for the treatment of a condition characterized by inappropriate cellular proliferation. The present invention further provides the use of a compound for the preparation of a medicament for inhibiting proliferation of a cell. The present invention further provides the use of a compound for the preparation of a medicament for inhibiting mitosis in a cell.

While it is possible that, for use in therapy, a therapeutically effective amount of a compound of the invention may be administered as the raw chemical, it is typically presented as the active ingredient of a pharmaceutical composition or formulation. Accordingly, the invention further provides a pharmaceutical composition comprising a compound of the invention. The pharmaceutical composition may further comprise one or more pharmaceutically acceptable carriers, diluents, and/or excipients. The carrier(s), diluent(s) and/or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the invention with one or more pharmaceutically acceptable carriers, diluents and/or excipients.

Pharmaceutical formulations may be presented in unit dose form containing a predetermined amount of active ingredient per unit dose. Such a unit may contain a therapeutically effective dose of the compound of the invention or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quarternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of active ingredient. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added. Where appropriate, dosage unit formulations for oral administration can be microencapsulated. The formulation can also be prepared to prolong or sustain the release as for example by coating or embedding particulate material in polymers, wax or the like.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the invention may also be delivered by the use of monoclonal antibodies as individual carriers to which the compound molecules are coupled. The compounds may also be coupled with soluble polymers as targetable drug carriers. Such polymers can include peptides, polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as ggenerally described in *Pharmaceutical Research,* 3(6): 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

In the above-described methods of treatment and uses, a compound of the invention may be employed alone, in combination with one or more other compounds of the invention or in combination with other therapeutic agents and/or in combination with other anti-neoplastic therapies. In particular, in methods of treating conditions mediated by PLK and methods of treating susceptible neoplasms, combination with other chemotherapeutic agents is envisaged as well as combination with surgical therapy and radiation therapy. The term "chemotherapeutic" as used herein refers to any chemical agent having a therapeutic effect on the subject to which it is administered. "Chemotherapeutic" agents include but are not limited to anti-neoplastic agents, analgesics and anti-emetics. As used herein, "anti-neoplastic agents" include both cytostatic and cytotoxic agents such as but not limited to cytotoxic chemotherapy, hormonal therapy, targeted kinase inhibitors and therapeutic monoclonal antibodies. Combination therapies according to the present invention thus comprise the administration of at least one compound of the invention and the use of at least one other cancer treatment method. In one embodiment, combination therapies according to the present invention comprise the administration of at least one compound of the invention and at least one other chemotherapeutic agent. In one particular embodiment, the present invention comprises the administration of at least one compound of the invention and at least one anti-neoplastic agent. As an additional aspect, the present invention provides the methods of treatment and uses as described above, which comprise administering a compound of the invention together with at least one chemotherapeutic agent. In one particular embodiment, the chemotherapeutic agent is an anti-neoplastic agent. In another embodiment, the present invention provides a pharmaceutical composition as described above further comprising at least one other chemotherapeutic agent, more particularly, the chemotherapeutic agent is an anti-neoplastic agent.

Typically, any chemotherapeutic agent that has activity versus a susceptible neoplasm being treated may be utilized in combination with the compounds of the invention, provided that the particular agent is clinically compatible with therapy employing a compound of the invention. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphor-ines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and antifolate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids. Examples of diterpenoids include, but are not limited to, paclitaxel and its analog docetaxel. Examples of vinca alkaloids include, but are not limited to, vinblastine, vincristine, and vinorelbine. Platinum coordination complexes are non-phase specific anti-neoplastic agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, oxaliplatin, cisplatin and carboplatin.

Alkylating agents are non-phase specific anti-neoplastic agents and strong electrophiles. Typically, alkylating agents form covalent linkages, by alkylation, to DNA through nucleophilic moieties of the DNA molecule such as phosphate, amino, and hydroxyl groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Antibiotic chemotherapeutic agents are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthracyclins such as daunorubicin and doxorubicin; and bleomycins.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine and thioguanine.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin. Hormones and hormonal analogues are useful compounds for treating cancers in which there is a relationship between the hormone(s) and growth and/or lack of growth of the cancer. Examples of hormones and hormonal analogues believed to be useful in the treatment of neoplasms include, but are not limited to, adrenocorti-costeroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene and iodoxyfene useful in the treatment of hormone dependent breast carcinoma; and gonadotropin-releasing hormone (GnRH) and analogues thereof, such as goserelin acetate and leuprolide, which stimulate the release of leutinizing hormone (LH) and/or follicle stimulating hormone (FSH) with short-term or intermittent use but lead to suppression of LH and FSH with long-term use indicated for the treatment prostatic carcinoma and hormone dependent breast carcinoma. Signal transduction pathway inhibitors are those inhibitors which block or inhibit a chemical process which evokes an intracellular change. As used herein this change is cell proliferation, survival, angiogenesis or differentiation. Signal tranduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are sometimes termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFR, ErbB2 and ErbB4), platelet derived growth factor receptor (PDGFR), vascular endothelial growth factor receptor (VEGFR), tyrosine kinase with immunoglobulin-like and epidermal growth factor homology domains (TIE-2), insulin growth factor-I receptor (IGF-I), macrophage colony stimulating factor (cfms), BTK, ckit, cmet, fibroblast growth factor (FGF) receptors, Trk receptors (TrkA, TrkB, and TrkC), ephrin (Eph) receptors, and the RET protooncogene. Several inhibitors of growth factor receptors are under development and include ligand antagonists, antibodies, tyrosine kinase inhibitors, anti-sense oligonucleotides and aptamers. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth Factor Receptors as Targets", New Molecular Targets for Cancer Chemotherapy, Ed. Workman, Paul and Kerr, David, CRC Press 1994, London.

Tyrosine kinases, which are not growth factor receptor kinases are termed non-receptor tyrosine kinases. Non-receptor tyrosine kinases useful in the present invention, which are targets or potential targets of anti-neoplastic drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual Review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (Rafk), Mitogen or Extracellular Regulated Kinase (MEKs), and Extracellular Regulated Kinases (ERKs); and Protein kinase C family member blockers including blockers of subtypes of PKCs (alpha, beta, gamma, epsilon, mu, lambda, iota, zeta), IkB kinase family (IKKa, IKKb), PKB family kinases, Akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60.1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; and Martinez-lacaci, L., et al, Int. J. Cancer (2000), 88(1), 44-52.

Inhibitors of Phosphotidyl Inositol-3 Kinase family members including blockers of PI3-kinase, ATM, DNA-PK, and Ku are also useful in combination with the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer Res, (2000) 60(6), 1541-1545.

Also useful in combination with the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC Press 1994, London.

Another group of signal transduction pathway inhibitors useful in combination with the present invention are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block Ras activation in cells containing wild type mutant Ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9(2)99-102; and BioChim. Biophys. Acta, (1989) 1423(3):19-30.

As mentioned above, antibodies to receptor kinase ligand binding may also serve as signal transduction inhibitors. This group of signal transduction pathway inhibitors includes the use of humanized antibodies to the extracellular ligand binding domain of receptor tyrosine kinases. For example, Imclone C225 EGFR specific antibody (see Green, M. C. et al, Monoclonal Antibody Therapy for Solid Tumors, Cancer Treat. Rev., (2000), 26(4), 269-286); Herceptin® ErbB2 antibody (see Tyrosine Kinase Signaling in Breast Cancer:ErbB Family Receptor Tyrosine Kinases, Breast Cancer Res., 2000, 2(3), 176-183); and 2CB VEGFR2 specific antibody (see Brekken, R. A. et al, Selective Inhibition of VEGFR2 Activity by a Monoclonal Anti-VEGF Antibody Blocks Tumor Growth in Mice, Cancer Res. (2000) 60, 5117-5124).

Receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Other inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$, beta$_3$) that will inhibit angiogenesis; endostatin and angiostatin (non-RTK) may also prove useful in combination with PLK inhibitors.

Agents used in immunotherapeutic regimens may also be useful in combination with the compounds of the invention.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al., J. Clin. Oncol 18:1812-1823 (2000); and Kitada S et al., Antisense Res. Dev. 4:71-79 (1994).

Cell cycle signaling inhibitors inhibit molecules involved in the control of the cell cycle. Cyclin dependent kinases (CDKs) and their interaction cyclins control progression through the eukaryotic cell cycle. The coordinated activation and inactivation of different cyclin/CDK complexes is necessary for normal progression through the cell cycle. Several inhibitors of cell cycle signaling are under development. For instance, examples of cyclin dependent kinases, including CDK2, CDK4, and CDK6 and inhibitors for the same are described in, for instance, Rosania, et al., Exp. Opin. Ther. Patents 10(2):215-230 (2000).

In one embodiment, the methods of the present invention comprise administering to the animal a compound of the invention in combination with a signal transduction pathway inhibitor, particularly gefitinib (IRESSA®).

The methods and uses employing these combinations may comprise the administration of the compound of the invention and the other chemotherapeutic/anti-neoplastic agent either sequentially in any order or simultaneously in separate or combined pharmaceutical compositions. When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of the invention is used in combination with a chemotherapeutic agent, the dose of each compound may differ from that when the compound is used alone. Appropriate doses will be readily appreciated by those skilled in the art. The appropriate dose of the compound(s) of the invention and the other therapeutically active agent(s) and the relative timings of administration will be selected in order to achieve the desired combined therapeutic effect, and are within the expertise and discretion of the attendent clinician.

The compounds of the invention may be conveniently prepared by the methods described in the examples which follow.

The present invention also provides radiolabeled compounds of the invention and biotinylated compounds of the invention and solid-support-bound versions thereof. Radiolabeled compounds of the invention and biotinylated compounds of the invention can be prepared using conventional techniques. For example, radiolabeled compounds of the invention can be prepared by reacting the compound of the invention with tritium gas in the presence of an appropriate catalyst to produce radiolabeled compounds of the invention. In one embodiment, the compounds are tritiated.

The radiolabeled compounds of the invention and biotinylated compounds of the invention are useful in assays for the identification of compounds which inhibit PLK, for the identification of compounds for the treatment of a condition mediated by PLK, for the treatment of susceptible neoplasms, for the treatment of conditions characterized by inappropriate proliferation, for the inhibition of proliferation of a cell and for the inhibition of mitosis in a cell. Accordingly, the present invention provides an assay method for identifying such compounds, which method comprises the step of specifically binding the radiolabeled compound of the invention or the biotinylated compound of the invention to the target protein or cellular homogenates. More specifically, suitable assay methods will include competition binding assays. The radiolabeled compounds of the invention and biotinylated compounds of the invention and solid-support-bound versions thereof, can be employed in assays according to the methods conventional in the art.

The following examples are intended for illustration only and are not intended to limit the scope of the invention in any way, the invention being defined by the claims which follow.

The following abbreviations as employed in the examples, have the recited meanings.

g gram(s)
mg milligram(s)
mol mole(s)
mmol millimole(s)
N normal
L liter(s)
mL milliliter(s)
μL microliter(s)
h hour(s)
min minute(s)
° C. degrees Centigrade
HCl hydrochloric acid
DCM dichloromethane
MeOH methanol
EtOAc ethyl acetate
$MgSO_4$ magnesium sulfate
$NaHCO_3$ sodium bicarbonate
$K_2CO_3$ potassium carbonate
$Na_2SO_4$ sodium sulfate
$N_2$ nitrogen
$H_2$ hydrogen
XANTPHOS (4,5-Bis(diphenylphosphino)-9,9-dimethylxanthene) is a commercially available catalyst, from Aldrich.

Reagents are commercially available or are prepared according to procedures in the literature. In the following structures, "Me" refers to the group —$CH_3$.

INTERMEDIATE EXAMPLE 1

Methyl 5-amino-3-({(1R)-1-[2-(trifluoromethyl)phenyl]ethyl}oxy)-2-thiophenecarboxylate

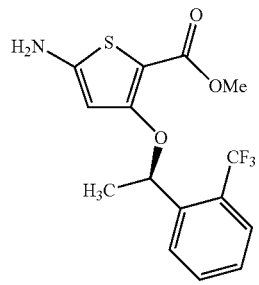

Step A—Methyl 5-nitro-3-({(1R)-1-[2-(trifluoromethyl)phenyl]ethyl}oxy)-2-thiophenecarboxylate

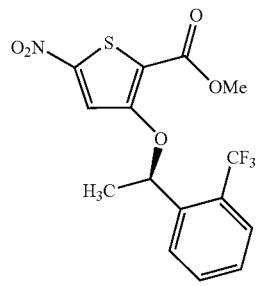

A slurry of polymer-supported triphenylphosphine (62.36 g, 2.21 mmol/g, 137.8 mmol) in DCM (1.0 L) was stirred at room temperature for 10 minutes. The mixture was cooled to 0° C. Methyl 3-hydroxy-5-nitro-2-thiophenecarboxylate (20.00 g, 98.44 mmol), which may be prepared in a manner analogous to the literature procedure (Barker, J. M.; Huddleston, P. R.; Wood, M. L.; Burkitt, S. A. *Journal of Chemical Research (Miniprint)* 2001, 1001-1022) was added, followed by (1S)-1-[2-(trifluoromethyl)phenyl]ethanol (26.20 g, 137.8 mmol) and di-tert-butyl azodicarboxylate (31.73 g, 137.8 mmol). The reaction mixture was stirred at room temperature for 21.25 h and then was filtered through a fritted funnel and concentrated. The residue was treated with 4 N HCl in 1,4-dioxane (300 mL) and stirred at room temperature for 3 h. The mixture was then quenched by addition of 3 N sodium hydroxide (300 mL) and saturated aqueous NaHCO$_3$ (200 mL). The mixture was extracted with DCM (3×250 mL). The combined organic fractions were dried over MgSO$_4$, filtered, and concentrated onto silica gel. Purification by column chromatography (0 to 25% EtOAc:hexanes) provided 36.08 g (98%) of the title compound as yellow oil. $^1$H NMR (300 MHz, CDCl$_3$): δ 7.82 (d, 1H, J=7.8 Hz), 7.68 (d, 1H, J=7.8 Hz), 7.59 (t, 1H, J=7.4 Hz), 7.46 (s, 1H), 7.42 (t, 1H, J=7.6 Hz), 5.77 (q, 1H, J=6.1 Hz), 3.94 (s, 3H), 1.74 (d, 3H, J=6.1 Hz).

Step B—Methyl 5-amino-3-({(1R)-1-[2-(trifluoromethyl)phenyl]ethyl}oxy)-2-thiophenecarboxylate

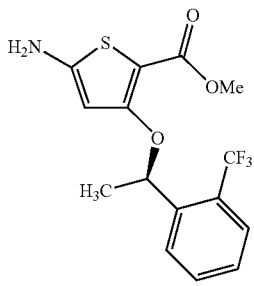

To a flask equipped with a temperature probe, an overhead mechanical stirrer, a reflux condenser, and an addition funnel was added iron powder (26.84 g, 480.6 mmol) and acetic acid (130 mL). The iron/acetic acid slurry was stirred mechanically and heated to an internal temperature of 50° C. To the addition funnel was added a solution of methyl 5-nitro-3-({(1R)-1-[2-(trifluoromethyl)phenyl]ethyl}oxy)-2-thiophenecarboxylate (36.08 g, 96.13 mmol) in acetic acid (160 mL). The solution in the addition funnel was then added dropwise to the iron/acetic acid slurry at a rate such that the internal temperature was maintained at <60° C. (2.5 h total addition time). The reaction mixture was cooled to room temperature, diluted with DCM (500 mL), and then quenched by addition of 6 N sodium hydroxide (750 mL) and saturated aqueous NaHCO$_3$ (200 mL). The entire mixture was then filtered through a pad of Celite to remove insoluble material, rinsing the Celite with additional DCM (250 mL). The aqueous and organic fractions were separated. The aqueous fraction was extracted with EtOAc (2×400 mL). The organic fractions were combined, dried over MgSO$_4$, filtered, and concentrated to afford 30.66 g (92%) of the title compound as an orange solid. $^1$H NMR (300 MHz, CDCl$_3$): δ 7.89 (d, 1H, J=7.7 Hz), 7.62 (d, 1H, J=7.7 Hz), 7.56 (t, 1H, J=7.7 Hz), 7.36 (t, 1H, J=7.7 Hz), 5.72 (s, 1H), 5.65 (q, 1H, J=6.3 Hz), 4.26 (br s, 2H), 3.80 (s, 3H), 1.66 (d, 3H, J=6.3 Hz); MS (APCI): 368.00 [M+Na]$^+$.

INTERMEDIATE EXAMPLE 2

Methyl 5-amino-3-{[(1R)-1-(2-chlorophenyl)ethyl]oxy}-2-thiophenecarboxylate

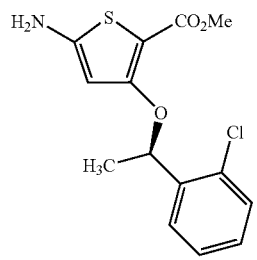

Step A—Methyl 3-{[(1R)-1-(2-chlorophenyl)ethyl]oxy}-5-nitro-2-thiophenecarboxylate

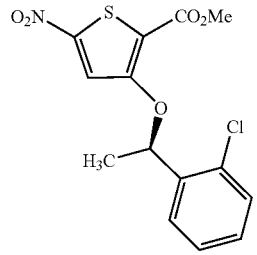

Methyl 3-{[(1R)-1-(2-chlorophenyl)ethyl]oxy}-5-nitro-2-thiophenecarboxylate was prepared from methyl 3-hydroxy-5-nitro-2-thiophenecarboxylate and (1S)-1-(2-chlorophenyl)ethanol by a procedure analogous to Intermediate Example 1, Step A. $^1$H NMR (400 MHz, DMSO-d$_6$): δ 7.96 (s, 1H), 7.65 (dd, 1H, J=1.7, 7.8 Hz), 7.47 (dd, 1H, J=1.5, 7.7 Hz), 7.40 (dt, 1H, J=1.3, 7.5 Hz), 7.34 (dt, 1H, J=1.9, 7.5 Hz), 5.98 (q, 1H, J=6.0 Hz), 3.85 (s, 3H), 1.59 (d, 3H, J=6.2 Hz).

Step B—Methyl 5-amino-3-{[(1R)-1-(2-chlorophenyl)ethyl]oxy}-2-thiophenecarboxylate

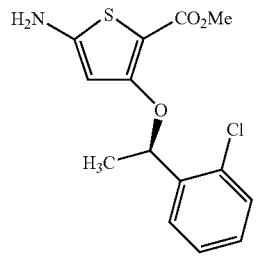

Methyl 5-amino-3-{[(1R)-1-(2-chlorophenyl)ethyl]oxy}-2-thiophenecarboxylate was prepared from methyl 3-{[(1R)-1-(2-chlorophenyl)ethyl]oxy}-5-nitro-2-thiophenecarboxylate by a procedure analogous to Intermediate Example 1, Step B. $^1$H NMR (400 MHz, DMSO-d$_6$): δ 7.54 (dd, 1H, J=1.8, 7.9 Hz), 7.45 (dd, 1H, J=1.4, 7.7 Hz), 7.37 (dt, 1H, J=1.4, 7.7 Hz), 7.31 (dt, 1H, J=1.8, 7.6 Hz), 6.76 (br s, 2H), 5.57 (q, 1H, J=6.2 Hz), 5.49 (s, 1H), 3.63 (s, 3H), 1.51 (d, 3H, J=6.4 Hz); MS (ESI): 334.03 [M+Na]$^+$.

EXAMPLE 1

5-{6-[(Methylsulfonyl)methyl]-1H-benzimidazol-1-yl}-3-({(1R)-1-[2-(trifluoromethyl)phenyl]ethyl}oxy)-2-thiophenecarboxamide

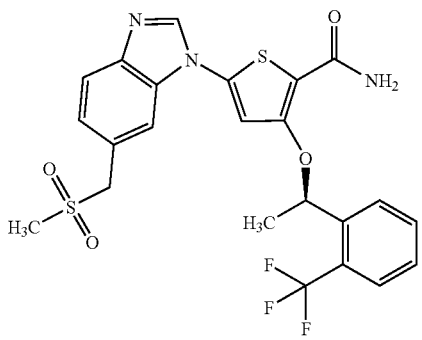

Route 1:

Step A—5-(Hydroxymethyl)-2-nitrophenol

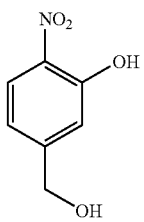

To a mixture of 3-hydroxy-4-nitrobenzoic acid (5.0 g, 27.3 mmol) in 1,2-dichloroethane (100 mL) was added trimethyl borate (4.9 mL, 43.7 mmol), followed by boron trifluoride diethyl etherate (5.5 mL, 43.7 mmol). Borane-pyridine complex (4.1 mL, 41.0 mmol) was then slowly added drop wise. The reaction was stirred 4 h at room temperature, then cooled to 0° C. and quenched with MeOH (10 mL). The mixture was concentrated under vacuum and the residue taken up in toluene (200 mL), then extracted with aqueous 1 N sodium hydroxide (3×100 mL). The combined aqueous layers were adjusted to pH 1.0 by addition of 12 N HCl, then extracted with EtOAc (3×250 mL). The combined organic layers were washed with water, brine, dried over MgSO$_4$ and concentrated under vacuum to give 4.55 g (98%) of the title compound as a light yellow solid. $^1$H NMR (400 MHz, DMSO-d$_6$): δ 10.87 (s, 1H), 7.85 (d, 1H, J=8.6 Hz), 7.08 (s, 1H), 6.88 (dd, 1H, J=1.19, 8.51 Hz), 5.43 (s, 1H), 3.33 (s, 2H).

Step B—3-Hydroxy-4-nitrobenzyl pivalate

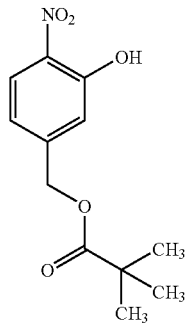

A mixture of 5-(hydroxymethyl)-2-nitrophenol (11.35 g, 67.15 mmol) and 3-(2,2-dimethylpropanoyl)-1,3-thiazolidine-2-thione (15.0 g, 73.89 mmol), which may be prepared in a manner analogous to the literature procedure (Yamada, S. Tetrahedron Letters 1992, 33, 2171-2174), was stirred in toluene (670 mL) at 100° C. for 40 h, then cooled to room temperature. The reaction was concentrated under vacuum to a volume of approximately 200 mL and the resulting slurry was filtered through filter paper, washing the solid with cold toluene. The filtrate was then concentrated under vacuum and purified by silica gel chromatography eluting with a gradient of 0-to-20% EtOAc/hexanes to give 11.09 g (65%) of the title compound as a clear yellow oil. $^1$H NMR (400 MHz, DMSO-d$_6$): δ 11.05 (s, 1H), 7.87 (d, 1H, J=8.42 Hz), 7.06 (s, 1H), 6.90 (dd, 1H, J=1.46, 8.42 Hz), 5.09 (s, 2H), 1.18 (s, 9H).

Step C—4-Nitro-3-{[(trifluoromethyl)sulfonyl]oxy}benzyl pivalate

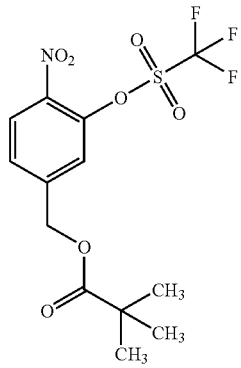

To a stirred, cooled (0° C.) solution of 3-hydroxy-4-nitrobenzyl pivalate (11.11 g, 43.9 mmol) and N-phenyltrifluoromethanesulfonimide (16.51 g, 46.2 mmol) in DCM (220 mL) was slowly added N,N-diisopropylethylamine (15.5 mL, 88.9 mmol). The reaction was stirred for 45 min at 0° C., then 45 min at room temperature. The reaction was then concentrated under vacuum and purified by silica gel chromatography eluting with a gradient of 5-to-20%

EtOAc/hexanes to give 16.87 g (99%) of the title compound as an off white solid. ¹H NMR (400 MHz, DMSO-d₆): δ 8.36 (d, 1H, J=8.42 Hz), 7.75-7.69 (m, 2H), 5.27 (s, 2H), 1.19 (s, 9H).

Step D—Methyl 5-[(5-{[(2,2-dimethylpropanoyl) oxy]methyl}-2-nitrophenyl)amino]-3-({(1R)-1-[2-(trifluoromethyl)phenyl]ethyl}oxy)thiophene-2-carboxylate

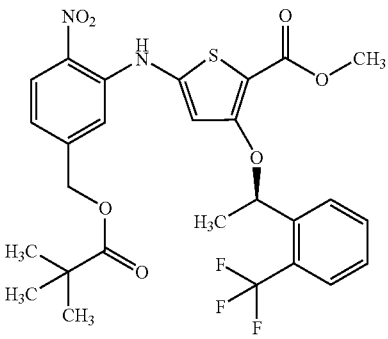

A mixture of 4-nitro-3-{[(trifluoromethyl)sulfonyl] oxy}benzyl pivalate (1.0 g, 2.60 mmol), methyl 5-amino-3-({(1R)-1-[2-(trifluoromethyl)phenyl]ethyl}-oxy)thiophene-2-carboxylate (1.34 g, 3.88 mmol), tetrakis (triphenylphosphine)palladium (0) (150 mg, 0.13 mmol), triphenylphosphine (68 mg, 0.26 mmol) and K₂CO₃ (900 mg, 6.5 mmol) were stirred in toluene (5.2 mL) at 100° C. for 2 h, then cooled to room temperature and filtered through Celite, washing with EtOAc and DCM. The filtrate was concentrated under vacuum and purified by silica gel chromatography eluting with a gradient of 5-to-25% EtOAc/hexane to give 1.26 g (84%) of the title compound as a red oil. ¹H NMR (400 MHz, DMSO-d₆): δ 9.75 (s, 1H), 8.09 (d, 1H, J=8.6 Hz), 7.89 (d, 1H, J=7.87 Hz), 7.69-7.78 (m, 2H), 7.52 (t, 1H, J=7.59 Hz), 7.34 (s, 1H), 7.01 (dd, 1H, J=1.46, 8.60 Hz), 6.62 (s, 1H), 5.70-5.75 (m, 1H), 5.07 (s, 2H), 3.74 (s, 3H), 1.58 (d, 3H, J=6.22 Hz), 1.13 (s, 9H).

Step E—Methyl 5-[(2-amino-5-{[(2,2-dimethylpropanoyl)oxy]methyl}phenyl)amino]-3-({(1R)-1-[2-(trifluoromethyl)phenyl]ethyl}oxy)thiophene-2-carboxylate

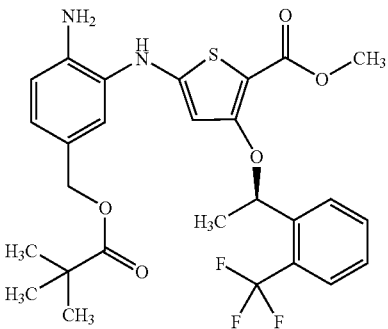

A mixture of methyl 5-[(5-{[(2,2-dimethylpropanoyl)oxy] methyl}-2-nitrophenyl)amino]-3-({(1R)-1-[2-(trifluoromethyl)phenyl]ethyl}oxy)thiophene-2-carboxylate (2.42 g, 4.17 mmol) and platinum (sulfided, 5 wt % on carbon) (811 mg, 0.21 mmol) in EtOAc (30 mL) was added to a high-pressure reaction flask. The reaction was purged with vacuum and N₂ gas, then H₂ gas was applied at 50 psi for 1 h. The reaction mixture was filtered through Celite, washing with EtOAc. The filtrate was concentrated under vacuum to give 2.27 g (99%) of the title compound as a tan solid. ¹H NMR (400 MHz, DMSO-d₆): δ 8.62 (s, 1H), 7.84 (d, 1H, J=7.87 Hz), 7.72 (dd, 2H, J=7.60, 13.09 Hz), 7.50 (t, 1H, J=7.60 Hz), 7.01 (d, 1H, J=1.46 Hz), 6.88 (dd, 1H, J=1.74, 8.15), 6.68 (d, 1H, J=8.24 Hz), 5.83 (s, 1H), 5.59-5.65 (m, 1H), 4.97 (s, 2H), 4.85 (s, 2H), 3.64 (s, 3H), 1.55 (d, 3H, J=6.23 Hz), 1.11 (s, 9H); MS (ESI): 551 [M+H]⁺.

Step F—Methyl 5-(6-{[(2,2-dimethlylpropanoyl) oxy]methyl}-1H-benzimidazol-1-yl)-3-({(1R)-1-[2-(trifluoromethyl)phenyl]ethyl}oxy)thiophene-2-carboxylate

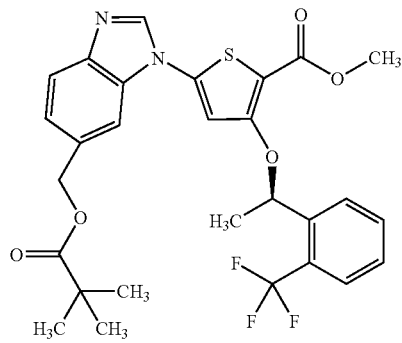

To a mixture of methyl 5-[(2-amino-5-{[(2,2-dimethylpropanoyl)oxy]methyl}phenyl)amino]-3-({(1R)-1-[2-(trifluoromethyl)phenyl]ethyl}-oxy)thiophene-2-carboxylate (2.27 g, 4.13 mmol) in triethylorthoformate (10 mL, 60.2 mmol) and DCM (3 mL) was added pyridinium p-toluenesulfonate (100 mg, 0.4 mmol). The reaction was stirred at 40° C. for 1 h, then cooled to room temperature. The entire reaction mixture was loaded onto silica gel and purified by silica gel chromatography eluting with a gradient of 0-to-50% EtOAc/hexanes to give 2.0 g (86%) of the title compound as a light tan solid. ¹H NMR (400 MHz, DMSO-d₆): δ 8.65 (s, 1H), 7.99 (d, 1H, J=7.87 Hz), 7.75-7.80 (m, 2H), 7.72 (d, 1H, J=7.87 Hz), 7.63 (s, 1H), 7.53 (t, 1H, J=7.60 Hz), 7.40 (s, 1H), 7.35 (d, 1H, J=8.42 Hz), 5.96 (q, 1H, J=6.10 Hz), 5.21 (s, 2H), 3.83 (s, 3H), 1.65 (d, 3H, J=6.23 Hz), 1.16 (s, 9H); MS (ESI): 561 [M+H]⁺.

Step G—Methyl 5-[6-(hydroxymethyl)-1H-benzimidazol-1-yl]-3-({(1R)-1-[2-(trifluoromethyl)phenyl]ethyl}oxy)thiophene-2-carboxylate

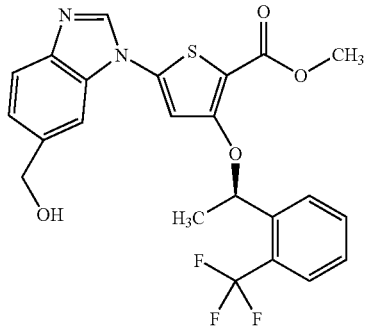

To a stirred solution of methyl 5-(6-{[(2,2-dimethylpropanoyl)oxy]methyl}-1H-benzimidazol-1-yl)-3-({(1R)-1-[2-(trifluoromethyl)phenyl]ethyl}oxy)thiophene-2-carboxylate (5.21 g, from a different batch using procedure analogous to Example 1, Route 1, Step F, 9.30 mmol) in MeOH (24 mL) was added 0.5M sodium hydroxide in MeOH (24.0 mL, 12 mmol). The reaction was stirred at room temperature for 72 h, then quenched with acetic acid (2 mL). The mixture was diluted with DCM (350 mL) and half saturated aqueous brine solution (150 mL). The aqueous layer was extracted with DCM (250 mL). The combined organics were dried over MgSO$_4$ and concentrated under vacuum to give 4.40 g (99%) of the title compound as a light yellow solid. $^1$H NMR (400 MHz, DMSO-d$_6$): δ 8.58 (s, 1H), 7.99 (d, 1H, J=7.87 Hz), 7.69-7.81 (m, 3H), 7.51-7.58 (m, 2H), 7.38 (s, 1H), 7.30 (d, 1H, J=8.42), 5.96 (q, 1H, J=6.10 Hz), 5.30 (t, 1H, J=5.77 Hz) 4.62 (d, 2H, J=5.86 Hz), 3.83 (s, 3H), 1.65 (d, 3H, J=6.23 Hz); MS (ESI): 477 [M+H]$^+$.

Step H—Methyl 5-[6-(chloromethyl)-1H-benzimidazol-1-yl]-3-({(1R)-1-[2-(trifluoromethyl)phenyl]ethyl}oxy)thiophene-2-carboxylate

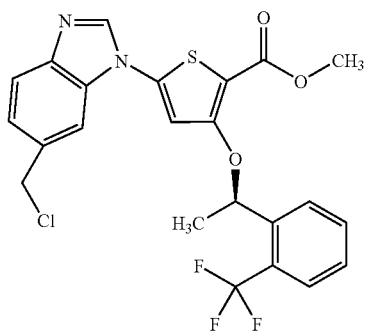

To a stirred solution of methyl 5-[6-(hydroxymethyl)-1H-benzimidazol-1-yl]-3-({(1R)-1-[2-(trifluoromethyl)phenyl]ethyl}oxy)thiophene-2-carboxylate (1.47 g, 3.08 mmol) and triphenylphosphine (1.05 g, 4.01 mmol) in DCM (30 mL) was added N-chlorosuccinimide (0.53 g, 4.01 mmol). The reaction was then heated to reflux and stirred for 20 minutes, then cooled to room temperature. The reaction was diluted with DCM (400 mL) and half saturated aqueous brine solution (150 mL). The aqueous layer was then extracted with DCM. The combined organic layers were dried over Na$_2$SO$_4$, concentrated under vacuum and purified by silica gel chromatography eluting with a gradient of 10-to-60% EtOAc/hexanes to give 1.4 g (92%) of the title compound as a white solid. $^1$H NMR (400 MHz, DMSO-d$_6$): δ 8.65 (s, 1H), 7.99 (d, 1H, J=7.87 Hz), 7.72-7.81 (m, 3H), 7.69 (s, 1H), 7.54 (t, 1H, J=7.69 Hz), 7.43 (d, 1H, J=8.42), 7.38 (s, 1H), 5.97 (q, 1H, J=6.10 Hz), 4.91 (s, 2H), 3.84 (s, 3H), 1.66 (d, 3H, J=6.23 Hz); MS (ESI): 495 [M+H]$^+$.

Step I—Methyl 5-{6-[(methylthio)methyl]-1H-benzimidazol-1-yl}-3-({(1R)-1-[2-(trifluoromethyl)phenyl]ethyl}oxy)thiophene-2-carboxylate

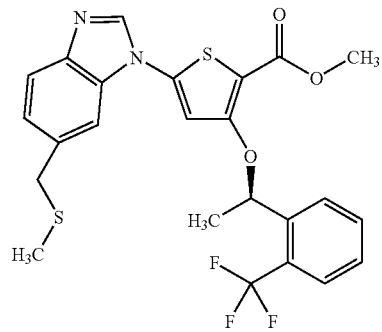

To a stirred mixture of methyl 5-[6-(chloromethyl)-1H-benzimidazol-1-yl]-3-({(1R)-1-[2-(trifluoromethyl)phenyl]ethyl}oxy)thiophene-2-carboxylate (200 mg, 0.40 mmol) in N,N-dimethylformamide (2.5 mL) was added sodium thiomethoxide (37 mg, 0.52 mmol). The reaction was stirred 30 min, then diluted with EtOAc, washed with water (5×), brine, dried over Na$_2$SO$_4$, concentrated under vacuum and purified by silica gel chromatography eluting with a gradient of 0-to-60% EtOAc/hexanes to give 147 mg (72%) of the title compound as a white solid. MS (ESI): 507 [M+H]$^+$.

Step J—5-{(6-[(Methylthio)methyl]-1H-benzimidazol-1-yl}-3-({(1R)-1-[2-(trifluoromethyl)phenyl]ethyl}oxy)thiophene-2-carboxamide

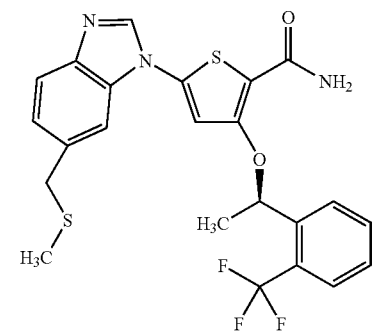

A mixture of methyl 5-{6-[(methylthio)methyl]-1H-benzimidazol-1-yl}-3-({(1R)-1-[2-(trifluoromethyl)phenyl]ethyl}oxy)thiophene-2-carboxylate (144.0 mg, 0.28 mmol) and 7N ammonia in MeOH (18 mL, 126.0 mmol) was added to a high-pressure glass reaction flask. The flask was sealed, then heated to 80° C. for approx. 16 h. The flask was cooled to room temperature, opened, and the reaction mixture concentrated under vacuum, then purified by silica gel chromatography, eluting with a 0-to-3% gradient of MeOH/DCM with 1% ammonium hydroxide to give 130 mg (93%) of the title compound as a white gold solid. $^1$H NMR (400 MHz, DMSO-$d_6$): δ 8.49 (s, 1H), 7.93 (d, 1H, J=7.68 Hz), 7.85 (br s, 1H), 7.80-7.75 (m, 2H), 7.69 (d, 1H, J=8.23 Hz), 7.56 (t, 1H, J=7.68 Hz), 7.39 (s, 1H), 7.29 (d, 1H, J=8.42 Hz), 7.15 (br s, 1H), 7.08 (s, 1H), 5.94 (m, 1H), 3.79 (s, 2H), 1.93 (s, 3H), 1.75 (d, 3H, J=6.22 Hz); MS (ESI): 492 [M+H]$^+$.

Step K—5-{6-[(Methylsulfonyl)methyl]-1H-benzimidazol-1-yl}-3-({(1R)-1-[2-(trifluoromethyl)phenyl]ethyl}oxy)thiophene-2-carboxamide

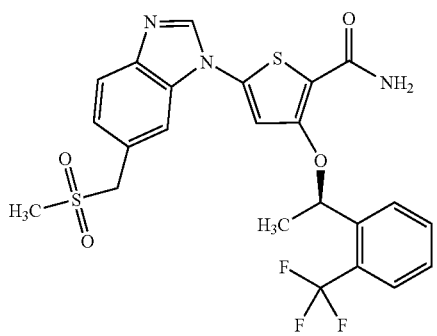

To a stirred, cooled (−10° C.) solution of 5-{6-[(methylthio)methyl]-1H-benzimidazol-1-yl}-3-({(1R)-1-[2-(trifluoromethyl)phenyl]ethyl}oxy)thiophene-2-carboxamide (76 mg, 0.15 mmol) in DCM (3.0 mL) was added m-chloroperoxybenzoic acid (70 mg, 0.31 mmol). The reaction was stirred 30 min, warmed to room temperature and stirred 15 min, then was concentrated under vacuum. The residue was diluted with chloroform and washed with aqueous saturated NaHCO$_3$, water, dried over Na$_2$SO$_4$, concentrated under vacuum, and purified by silica gel chromatography eluting with a gradient of 0-to-5% MeOH/DCM, with 1% ammonium hydroxide, to give 78 mg (96%) of the title compound as a white solid. $^1$H NMR (400 MHz, DMSO-$d_6$): δ 8.57 (s, 1H), 7.95 (d, 1H, J=7.87 Hz), 7.85 (br s, 1H), 7.80-7.73 (m, 3H), 7.69 (s, 1H), 7.55 (t, 1H, J=7.69 Hz), 7.38 (d, 1H, J=8.42 Hz), 7.19 (s, 1H), 7.12 (br s, 1H), 5.95-5.89 (m, 1H), 4.61-4.58 (m, 2H), 2.89 (s, 3H), 1.75 (d, 3H, J=6.04 Hz); MS (ESI): 524 [M+H]$^+$.

Route 2:

Step A—Methyl 5-{6-[(methylsulfonyl)methyl]-1H-benzimidazol-1-yl}-3-({(1R)-1-[2-(trifluoromethyl)phenyl]ethyl}oxy)-2-thiophenecarboxylate

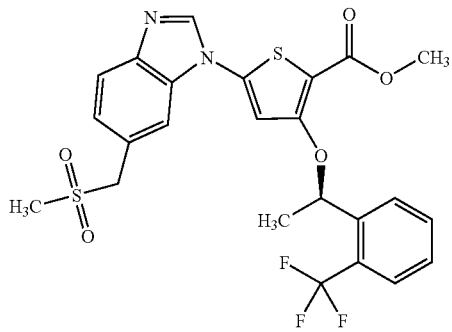

A mixture of methyl 5-[6-(chloromethyl)-1H-benzimidazol-1-yl]-3-({(1R)-1-[2-(trifluoromethyl)phenyl]ethyl}oxy)thiophene-2-carboxylate (4.53 g, from a different batch using procedure analogous to Example 1, Route 1, Step H, 9.17 mmol), methanesulfonic acid sodium salt (2.81 g, 27.5 mmol) and ethanol (40.0 mL) was added to a high-pressure glass reaction flask. The flask was sealed, then heated to 85° C. for approximately 16 h. The flask was cooled to room temperature, opened, and the reaction mixture concentrated under vacuum, then purified by silica gel chromatography, eluting with a 5-to-35% gradient of EtOAc/hexane to give 4.54 g (92%) of the title compound as a light yellow solid. $^1$H NMR (400 MHz, DMSO-$d_6$): δ 8.67 (s, 1H), 8.01 (d, 1H, J=7.87 Hz), 7.82-7.70 (m, 4H), 7.53 (t, 1H, J=7.69 Hz), 7.45 (s, 1H), 7.40 (d, 1H, J=8.42 Hz), 5.95 (m, 1H), 4.63 (m, 2H), 3.83 (s, 3H), 2.90 (s, 3H), 1.65 (d, 3H, J=6.204 Hz); MS (ESI): 539 [M+H]$^+$.

Step B—5-{6-[(Methylsulfonyl)methyl]-1H-benzimidazol-1-yl}-3-({(1R)-1-[2-(trifluoromethyl)phenyl]ethyl}oxy)thiophene-2-carboxamide

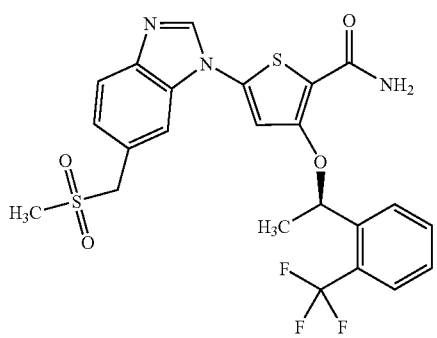

A mixture of methyl 5-{6-[(methylsulfonyl)methyl]-1H-benzimidazol-1-yl}-3-({(1R)-1-[2-(trifluoromethyl)phenyl]ethyl}oxy)-2-thiophenecarboxylate (4.53 g, 8.42 mmol) and 7N ammonia in MeOH (250.0 mL, 1.75 mol) was added to a high-pressure glass reaction flask. The flask was sealed, then heated to 85° C. for approx. 36 h. The flask was cooled to room temperature, opened, and the reaction mixture combined with a second batch of methyl 5-{6-[(methylsulfonyl)

methyl]-1H-benzimidazol-1-yl}-3-({(1R)-1-[2-(trifluoromethyl)phenyl]ethyl}oxy)-2-thiophenecarboxylate (4.11 g, 7.63 mmol), which had also been treated with 7N ammonia in MeOH (200.0 mL, 1.40 mol) in a high-pressure glass reaction flask at 85° C. for approximately 36 h, then cooled to room temperature and opened. The combined reaction mixtures were concentrated under vacuum, then purified by silica gel chromatography, eluting with a 0-to-5% gradient of MeOH/DCM, with 1% ammonium hydroxide, to give 7.47 g (89%) of the title compound as an off-white solid. MS (ESI): 524 [M+H]+.

EXAMPLE 2

3-{[(1R)-1-(2-Chlorophenyl)ethyl]oxy}-5-{6-[(methylsulfonyl)methyl]-1H-benzimidazol-1-yl}-2-thiophenecarboxamide

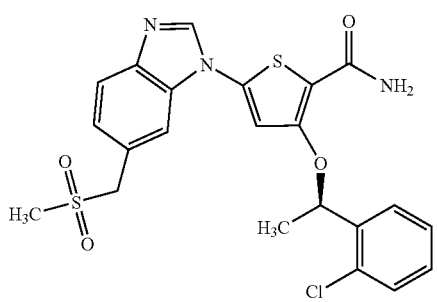

Step A—Methyl 3-{[(1R)-1-(2-chlorophenyl)ethyl]oxy}-5-{6-[(methylthio)methyl]-1H-benzimidazol-1-yl}thiophene-2-carboxylate

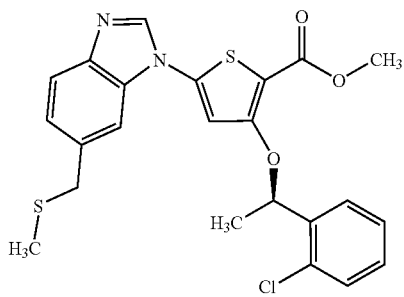

The title compound was prepared from methyl 5-[6-(chloromethyl)-1H-benzimidazol-1-yl]-3-{[(1R)-1-(2-chlorophenyl)ethyl]oxy}thiophene-2-carboxylate by a procedure analogous to Example 1, Route 1, Step I. MS (ESI): 473 [M+H]+.

Step B—3-{[(1R)-1-(2-Chlorophenyl)ethyl]oxy}-5-{6-[(methylthio)methyl]-1H-benzimidazol-1-yl}thiophene-2-carboxamide

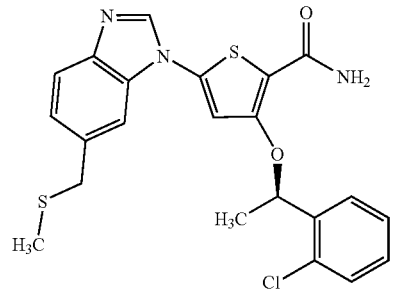

The title compound was prepared from methyl 3-{[(1R)-1-(2-chlorophenyl)ethyl]oxy}-5-{6-[(methylthio)methyl]-1H-benzimidazol-1-yl}thiophene-2-carboxylate by a procedure analogous to Example 1, Route 1, Step J. ¹H NMR (400 MHz, DMSO-d₆): δ 8.53 (s, 1H), 7.83 (s, 1H), 7.71-7.66 (m, 2H), 7.49 (d, 1H, J=7.87 Hz), 7.45-7.35 (m, 3H), 7.29 (d, 1H, J=8.42 Hz), 7.16-7.11 (m, 2H), 6.01-5.95 (m, 1H), 3.82 (s, 2H), 1.94 (s, 3H), 1.73 (d, 3H, J=6.41 Hz); MS (ESI): 458 [M+H]+.

Step C—3-{[(1R)-1-(2-Chlorophenyl)ethyl]oxy}-5-{6-[(methylsulfonyl)methyl]-1H-benzimidazol-1-yl}-2-thiophenecarboxamide

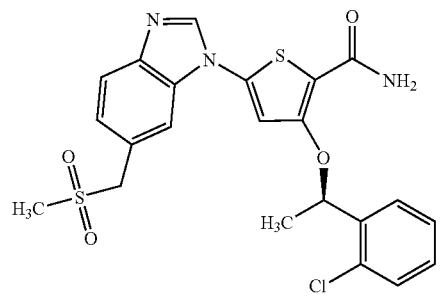

The title compound was prepared from 3-{[(1R)-1-(2-chlorophenyl)ethyl]oxy}-5-{6-[(methylthio)methyl]-1H-benzimidazol-1-yl}thiophene-2-carboxamide by a procedure analogous to Example 1, Route 1, Step K. ¹H NMR (400 MHz, DMSO-d₆): δ 8.61 (s, 1H), 7.84 (s, 1H), 7.79 (d, 1H, J=8.24 Hz), 7.73 (s, 1H), 7.70-7.67 (m, 1H), 7.49-7.47 (m, 1H), 7.44-7.33 (m, 3H), 7.26 (s, 1H), 7.12 (s, 1H), 5.97-5.93 (m, 1H), 4.64-4.60 (m, 2H), 2.90 (s, 3H), 1.73 (d, 3H, J=6.41 Hz); MS (ESI): 490 [M+H]+.

INTERMEDIATE EXAMPLE 3

Methyl 5-(6-bromo-1H-benzimidazol-1-yl)-3-hydroxy-2-thiophenecarboxylate

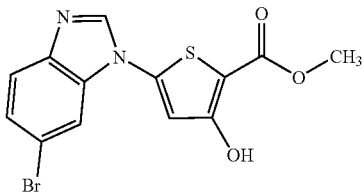

Step A—Methyl 5-(6-bromo-1H-benzimidazol-1-yl)-3-{[(1,1-dimethylethyl)(dimethyl)silyl]oxy}-2-thiophenecarboxylate

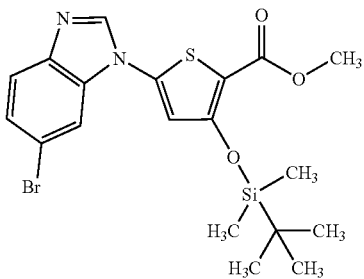

To a mixture of 5-bromo-1H-benzimidazole (43.78 g, 222.0 mmol) in chloroform (800 mL) was added N-methylimidazole (44.5 mL, 560.0 mmol), followed by methyl 2-chloro-3-oxo-2,3-dihydro-2-thiophenecarboxylate (44.8 g, 233.0 mmol). The reaction was stirred 20 h at room temperature, then N-methylimidazole (18.0 mL, 226.0 mmol) was added, followed by t-butyldimethylsilylchloride (36.8 g, 245.0 mmol). The reaction was stirred 1 hr, then quenched with MeOH and poured into DCM and water. The aqueous layer was extracted with DCM (3×). The combined organics were then dried over Na$_2$SO$_4$, concentrated and chromatographed on silica gel, eluting with a 50-to-75% gradient of 25% EtOAc in hexane/hexane to give 25.18 g (24%) of the title compound. MS (ESI): 467 [M+H]$^+$.

Step B—Methyl 5-(6-bromo-1H-benzimidazol-1-yl)-3-hydroxy-2-thiophenecarboxylate

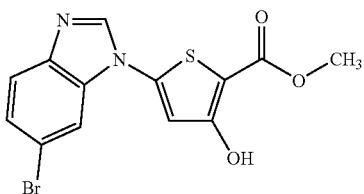

To a stirred solution of methyl 5-(6-bromo-1H-benzimidazol-1-yl)-3-{[(1,1-dimethylethyl)(dimethyl)silyl]oxy}-2-thiophenecarboxylate (25.18 g, 53.9 mmol) in THF (540.0 mL) was added 1.0M tetrabutylammonium flouride in THF (60.0 mL, 60.0 mmol). The reaction was stirred 1.5 h then aqueous saturated NH$_4$Cl was added (200 mL). The resulting slurry was stirred 15 min then diluted with water (750 mL) and EtOAc (1.0 L). The aqueous layer was separated and its pH adjusted to 3.0 by addition of aqueous 1M HCl. The aqueous layer was then extracted with EtOAc (3×). The combined organic layers were washed with aqueous 0.1M HCl, brine, dried over MgSO$_4$ and concentrated under vacuum to give 19.4 g (100%) of the title compound as a light yellow solid. MS (ESI): 353 [M+H]$^+$.

EXAMPLE 3

5-{6-[(4-Methylpiperazin-1-yl)methyl]-1H-benzimidazol-1-yl}-3-{(1R)-1-[2-(trifluoromethyl)phenyl]ethoxy}thiophene-2-carboxamide

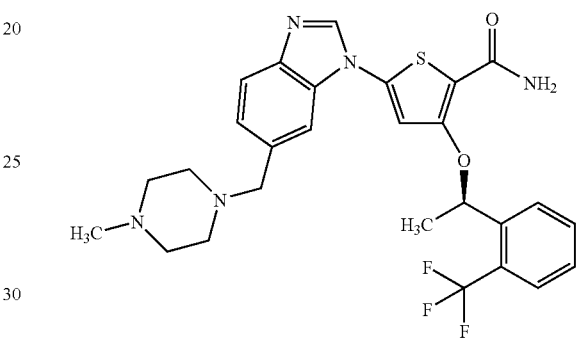

Route 1:

Step A—3- Methyl 5-(6-bromo-1H-benzimidazol-1-yl)-3-{(1R)-1-[2-(trifluoromethyl)phenyl]ethoxy}thiophene-2-carboxylate

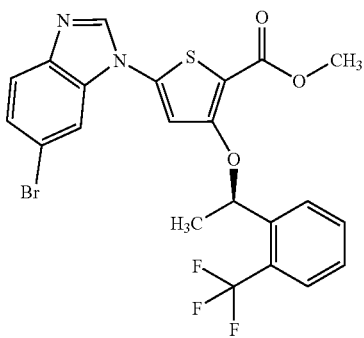

A slurry of polymer-supported triphenylphosphine (53.0 g, 2.04 mmol/g, 108 mmol), (1S)-1-[2-(trifluoromethyl)phenyl]ethanol (15.4 g, 81.0 mmol), and methyl 5-(6-bromo-1H-benzimidazol-1-yl)-3-hydroxythiophene-2-carboxylate (Intermediate Example 3) (19.0 g, 53.9 mmol) in DCM (750 mL) was stirred at room temperature, for 10 min. The slurry was then treated with di-tert-butyl azodicarboxylate (24.8 g, 108 mmol). The reaction mixture was stirred for 3 h, then poured through filter paper, washing the resin solids with DCM and MeOH. The filtrate was concentrated under vacuum and purified by silica gel chromatography, eluting with a 5-to-50% gradient of EtOAc/hexane to give 23.8 g (84%) of the title compound as a light yellow solid. ¹H NMR (400 MHz, DMSO-d₆): δ 8.63 (s, 1H), 7.97 (d, 1H, J=7.87 Hz), 7.80-7.71 (m, 3H), 7.65 (d, 1H, J=1.65 Hz), 7.57-7.48 (m, 2H), 7.35 (s, 1H), 5.99 (q, 1H, J=5.98 Hz), 3.83 (s, 3H), 1.65 (d, 3H, J=6.04 Hz); MS (ESI): 525 [M+H]⁺.

Step B—Methyl 3-{(1R)-1-[2-(trifluoromethyl)phenyl]ethoxy}-5-(6-vinyl-1H-benzimidazol-1-yl)thiophene-2-carboxylate

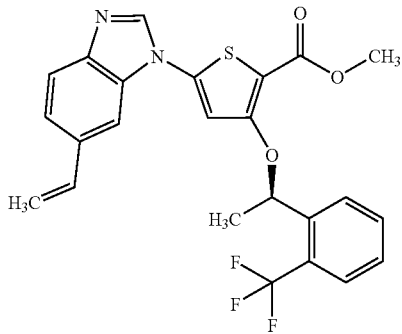

To a mixture of 3-methyl-5-(6-bromo-1H-benzimidazol-1-yl)-3-{(1R)-1-[2-(trifluoromethyl)phenyl]ethoxy}thiophene-2-carboxylate (23.8 g, 45.4 mmol), potassium vinyltrifluoroborate (7.25 g, 54.5 mmol) and triethylamine (6.3 mL, 45.4 mmol), stirred at room temperature in n-propanol (230 mL) was added [1,1'-bis(diphenylphosphino)-ferrocene]dichloropalladium(II) dichloromethane complex (750 mg, 0.91 mmol). The mixture was then heated to reflux and stirred for 3 h, then cooled to room temperature, poured into water and extracted with EtOAc (3×). The combined organic layers were washed with brine, dried over MgSO₄, concentrated under vacuum and purified by silica gel chromatography, eluting with a 10-to-40% gradient of EtOAc/hexane to give 17.06 g (80%) of the title compound as a yellow foam solid. ¹H NMR (400 MHz, DMSO-d₆): δ 8.59 (s, 1H), 7.98 (d, 1H, J=7.87 Hz), 7.80-7.71 (m, 3H), 7.59 (s, 1H), 7.56-7.52 (m, 2H), 7.39 (s, 1H), 6.85 (dd, 1H, J=10.98 and 17.75 Hz), 6.00 (q, 1H, J=6.10 Hz), 5.86 (d, 1H, J=17.56 Hz), 5.31 (d, 1H, J=10.98 Hz), 3.83 (s, 3H), 1.65 (d, 3H, J=6.04 Hz); MS (ESI): 473 [M+H]⁺.

Step C—Methyl 5-[6-(1,2-dihydroxyethyl)-1H-benzimidazol-1-yl]-3-{(1R)-1-[2-(trifluoromethyl)phenyl]ethoxy}thiophene-2-carboxylate

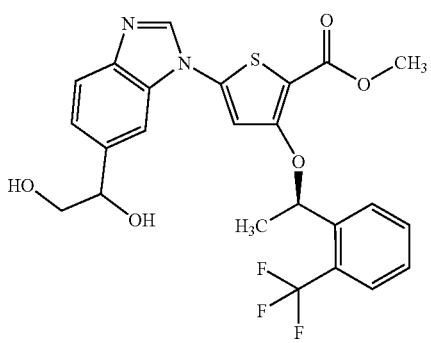

To a stirred solution of methyl 3-{(1R)-1-[2-(trifluoromethyl)phenyl]ethoxy}-5-(6-vinyl-1H-benzimidazol-1-yl)thiophene-2-carboxylate (17.06 g, 36.1 mmol) in 360 mL of acetone/water (3:1) was added 4-methylmorpholine N-oxide (5.1 g, 43.4 mmol) followed by 2.5 weight % solution osmium tetroxide in 2-methyl-2-propanol (10.0 mL, 0.8 mmol). The reaction was stirred at room temperature for 18 h, then quenched with aqueous (saturated) sodium sulfite. The mixture was extracted with EtOAc (3×). The combined organic layers were washed with brine, dried over MgSO₄, concentrated under vacuum and purified by silica gel chromatography, eluting with a 1-to-8% gradient of MeOH/DCM with 1% ammonium hydroxide to give 16.72 g (92%) of the title compound as a light yellow foam solid. ¹H NMR (400 MHz, DMSO-d): δ 8.59 (d, 1H, J=1.46 Hz), 7.98 (d, 1H, J=7.87 Hz), 7.80-7.68 (m, 3H), 7.59-7.52 (m, 2H), 7.36-7.31 (m, 2H), 5.95 (q, 1H, J=6.10 Hz), 5.37 (t, 1H, J=3.66 Hz), 4.76-4.64 (m, 2H), 3.83 (s, 3H), 3.46-3.42 (m, 2H), 1.65 (d, 3H, J=6.04 Hz); MS (ESI): 507 [M+H]⁺.

Step D—Methyl 5-(6-formyl-1H-benzimidazol-1-yl)-3-{(1R)-1-[2-(trifluoromethyl)phenyl]ethoxy}thiophene-2-carboxylate

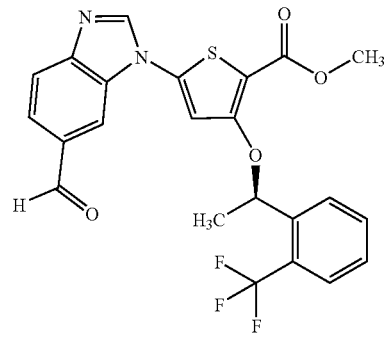

To a solution of methyl 5-[6-(1,2-dihydroxyethyl)-1H-benzimidazol-1-yl]-3-{(1R)-1-[2-(trifluoromethyl)phenyl]ethoxy}thiophene-2-carboxylate (16.72 g, 33.0 mmol) in 1:1:1 DCM/water/MeOH (220 mL) was added sodium periodate (10.58 g, 49.5 mmol). The resulting slurry was stirred for 1 h, then was diluted with water and EtOAc. The aqueous layer was extracted with EtOAc (3×). The combined organic layers were washed with brine, dried over MgSO₄ and concentrated under vacuum to give 14.76 g (94%) of the title compound as a light yellow foam solid. ¹H NMR (400 MHz, DMSO-d₆): δ 10.09 (s, 1H), 8.87 (s, 1H), 8.19 (s, 1H), 8.02-7.89 (m, 3H), 7.81-7.72 (m, 2H), 7.57-7.51 (m, 2H), 5.98 (q, 1H, J=6.10 Hz), 3.84 (s, 3H), 1.66 (d, 3H, J=6.22 Hz); MS (ESI): 475 [M+H]⁺.

Step E—Methyl 5-{6-[(4-methylpiperazin-1-yl)methyl]-1H-benzimidazol-1-yl}-3-{(1R)-1-[2-(trifluoromethyl)phenyl]ethoxy}thiophene-2-carboxylate

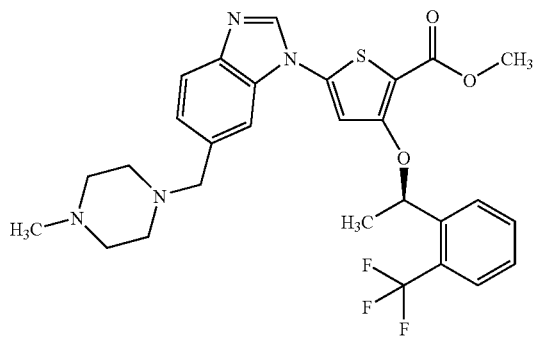

To a stirred solution of methyl 5-(6-formyl-1H-benzimidazol-1-yl)-3-{(1R)-1-[2-(trifluoromethyl)phenyl]ethoxy}thiophene-2-carboxylate (14.76 g, 31.1 mmol), n-methylpiperazine (5.72 mL, 62.3 mmol) and acetic acid (2.1 mL, 37.4 mmol) in dichloroethane (150 mL) was added sodium triacetoxyborohydride (9.9 g, 46.7 mmol). The reaction was stirred for 1.5 h, then aqueous 5% $K_2CO_3$ was added until the pH was approx. 8. The mixture was then diluted with EtOAc and water. The aqueous layer was extracted with EtOAc (3×). The combined organic layers were washed with brine, dried over $Na_2SO_4$, concentrated under vacuum and purified by silica gel chromatography, eluting with a 1-to-8% gradient of MeOH/DCM with 1% ammonium hydroxide to give 15.82 g (91%) of the title compound as a light yellow foam solid. $^1$H NMR (400 MHz, DMSO-$d_6$): δ 8.57 (s, 1H), 7.98 (d, 1H, J=7.87 Hz), 7.80-7.68 (m, 3H), 7.54 (t, 1H, J=7.59 Hz), 7.46 (s, 1H), 7.33-7.28 (m, 2H), 5.97 (q, 1H, J=6.16 Hz), 3.83 (s, 3H), 3.55 (s, 2H), 2.45-2.20 (m, 8H), 2.13 (s, 3H), 1.66 (d, 3H, J=6.04 Hz); MS (ESI): 559 [M+H]$^+$.

Step F—5-{6-[(4-methylpiperazin-1-yl)methyl]-1H-benzimidazol-1-yl}-3-{(1R)-1-[2-(trifluoromethyl)phenyl]ethoxy}thiophene-2-carboxamide

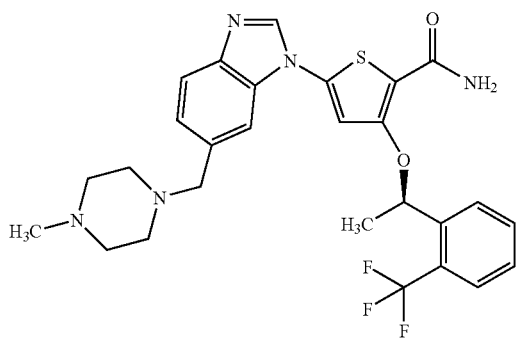

A mixture of methyl 5-{6-[(4-methylpiperazin-1-yl)methyl]-1H-benzimidazol-1-yl}-3-{(1R)-1-[2-(trifluoromethyl)phenyl]ethoxy}thiophene-2-carboxylate (15.82 g, 28.35 mmol) and 7N ammonia in MeOH (250 mL, 1.75 mol) was added to a high-pressure glass reaction flask. The flask was sealed, then heated to 80° C. for approx. 40 h. The flask was cooled to room temperature, opened, and the reaction mixture concentrated under vacuum, then purified by silica gel chromatography, eluting with a 2-to-8% gradient of MeOH/DCM with 1% ammonium hydroxide to give 14.11 g (92%) of the title compound as a white foam solid. $^1$H NMR (400 MHz, DMSO-$d_6$): δ 8.49 (s, 1H), 7.93 (d, 1H, J=7.87 Hz), 7.86 (br s, 1H), 7.80-7.75 (m, 2H), 7.68 (d, 1H, J=8.23 Hz), 7.56 (t, 1H, J=7.68 Hz), 7.33 (s, 1H), 7.28 (d, 1H, J=8.42 Hz), 7.15 (br s, 1H), 7.06 (s, 1H), 5.94 (q, 1H, J=6.10 Hz), 3.52 (s, 2H), 2.45-2.20 (m, 8H), 2.13 (s, 3H), 1.74 (d, 3H, J=6.22 Hz); MS (ESI): 544 [M+H]$^+$.

Route 2:

Step A—2-bromo-4-{[(methyloxy)methyl]oxy}-1-nitrobenzene

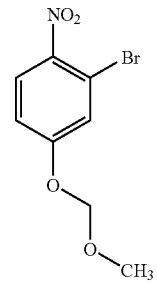

A solution of 3-bromo-4-nitrophenol (20.0 g, 91.7 mmol) in DCM (475 mL) was stirred at 0° C. Diisopropylethylamine (19.2 mL, 110.0 mmol) was added, followed by the drop wise addition of a solution of chloromethyl methyl ether (7.7 mL, 100.9 mmol) in DCM (25 mL). The reaction was stirred at 0° C. for 1 hr, then warmed to room temperature and quenched with water (150 mL). The mixture was poured into brine (150 mL) and the aqueous layer extracted with EtOAc (3×). The combined organic layers were washed with brine, dried over $MgSO_4$, concentrated under vacuum and chromatographed on silica gel (330 g), eluting with a 0-to-25% gradient of EtOAc/hexane to give 20.0 g (83%) of the title compound as a clear orange oil. $^1$H NMR (400 MHz, DMSO-$d_6$): δ 8.07 (d, 1H, J=8.97 Hz), 7.50 (d, 1H, J=2.20 Hz), 7.21 (dd, 1H, J=8.97 and 2.38 Hz), 5.34 (s, 2H), 3.39 (s, 3H).

Step B—Methyl 5-[(5-{[(methyloxy)methyl]oxy}-2-nitrophenyl)amino]-3-({(1R)-1-[2-(trifluoromethyl)phenyl]ethyl}oxy)-2-thiophenecarboxylate

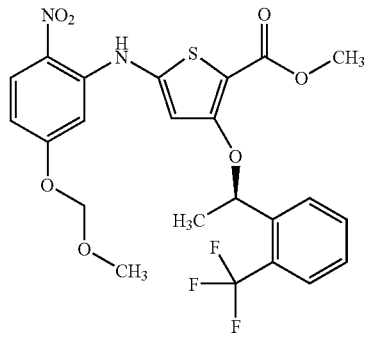

To a stirred solution of methyl 5-amino-3-({(1R)-1-[2-(trifluoromethyl)phenyl]-ethyl}oxy)-2-thiophenecarboxylate (1.32 g, 3.82 mmol) and 2-bromo-4-{[(methyloxy)methyl]oxy}-1-nitrobenzene (1.0 g, 3.82 mmol) in dioxane (20 mL) was added tris(dibenzylideneacetone)dipalladium(0) (70.0 mg, 0.076 mmol) and XANTPHOS (97.0 mg, 0.17 mmol) followed by cesium carbonate (6.2 g, 19.0 mmol). The mixture was heated to 60° C. and stirred for 12 h, then cooled to room temperature, diluted with EtOAc and filtered through Celite, washing the solids with EtOAc and DCM. The filtrate was concentrated under vacuum and chromatographed on silica gel (120 g), eluting with a 5-to-35% gradient of EtOAc/hexane to give 1.64 g (82%) of the title compound as a red oil. $^1$H NMR (400 MHz, DMSO-$d_6$): δ 9.85 (s, 1H), 8.12 (d, 1H, J=9.33 Hz), 7.90 (d, 1H, J=7.87 Hz), 7.74 (m, 2H), 7.53 (t, 1H, J=7.68 Hz), 6.84 (d, 1H, J=2.56 Hz), 6.73-6.68 (m, 2H), 5.77-5.72 (m, 1H), 5.23 (s, 2H), 3.75 (s, 3H), 3.37 (s, 3H), 1.58 (d, 3H, J=6.22 Hz); MS (ESI): 527 [M+H]$^+$.

Step C—Methyl 5-(6-{[(methyloxy)methyl]oxy}-1H-benzimidazol-1-yl)-3-({(1R)-1-[2-(trifluoromethyl)phenyl]ethyl}oxy)-2-thiophenecarboxylate

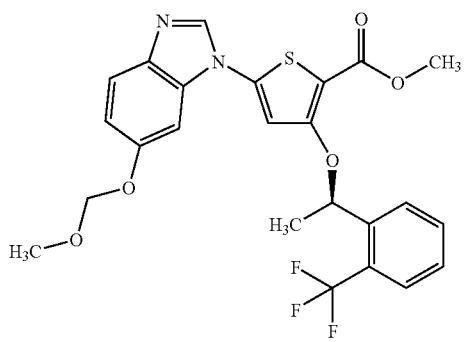

To a high-pressure hydrogenation reaction flask was added methyl 5-[(5-{[(methyloxy)methyl]oxy}-2-nitrophenyl)amino]-3-({(1R)-1-[2-(trifluoromethyl)phenyl]ethyl}oxy)-2-thiophenecarboxylate (2.0 g, 3.8 mmol), pyridinium p-toluene sulfonate (95.0 mg, 0.38 mmol), 5% by weight platinum on carbon (sulfided) (740 mg, 0.19 mmol) and trimethylorthoformate (40 mL). The flask was purged with N$_2$ (gas) vacuum (3×), then with H$_2$ (gas)/vacuum (3×). H$_2$ gas was then applied at 50 psi for 3 h. The reaction mixture was then filtered through Celite, washing the solids with EtOAc and DCM. The filtrate was then concentrated under vacuum to 1.92 g (100%) of the title compound as a light yellow foam solid. $^1$H NMR (400 MHz, DMSO-$d_6$): δ 8.49 (s, 1H), 7.98 (d, 1H, J=8.05 Hz), 7.79-7.66 (m, 3H), 7.53 (t, 1H, J=7.59 Hz), 7.35 (s, 1H), 7.22 (d, 1H, J=2.20 Hz), 7.06 (dd, 1H, J=8.78 and 2.20 Hz) 5.97 (q, 1H, J=6.04 Hz), 5.23 (s, 2H), 3.83 (s, 3H), 3.39 (s, 2H), 1.65 (d, 3H, J=6.22 Hz); MS (ESI): 507 [M+H]$^+$.

Step D—Methyl 5-(6-hydroxy-1H-benzimidazol-1-yl)-3-({(1R)-1-[2-(trifluoromethyl)phenyl]ethyl}oxy)-2-thiophenecarboxylate

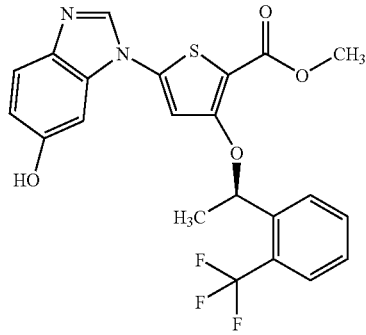

To a stirred solution of methyl 5-(6-{[(methyloxy)methyl]oxy}-1H-benzimidazol-1-yl)-3-({(1R)-1-[2-(trifluoromethyl)phenyl]ethyl}oxy)-2-thiophenecarboxylate (8.18 g, a different batch using procedure analogous to Example 3, Route 2, Step C, 16.16 mmol) in 1:1 THF/MeOH (130 mL) was added 1N HCl in water (65 mL, 65.0 mmol). The reaction mixture was heated to 35° C. and stirred for 72 h then cooled to room temperature. The reaction was poured into DCM (500 mL) and water added (100 mL). The mixture was neutralized to pH 7 by addition of aqueous (saturated) NaHCO$_3$. The aqueous layer was then extracted with DCM (1×) and EtOAc (1×). The combined organic layers were dried over MgSO$_4$, concentrated under vacuum, and chromatographed on silica gel (120 g), eluting with a 10-to-60% gradient of EtOAc/hexane to give 6.9 g (92%) of the title compound as a light salmon colored foam solid. $^1$H NMR (400 MHz, DMSO-$d_6$): δ 9.62 (s, 1H), 8.41 (s, 1H), 8.00 (d, 1H, J=7.87 Hz), 7.80-7.71 (m, 2H), 7.56-7.51 (m, 2H), 7.38 (s, 1H), 7.05 (d, 1H, J=2.01 Hz), 6.81 (dd, 1H, J=8.70 and 2.11 Hz) 5.95 (m, 1H), 3.83 (s, 3H), 1.64 (d, 3H, J=6.23 Hz); MS (ESI): 463 [M+H]$^+$.

Step E—Methyl 3-({(1R)-1-[2-(trifluoromethyl)phenyl]ethyl}oxy)-5-(6-{[(trifluoromethyl)sulfonyl]oxy}-1H-benzimidazol-1-yl)-2-thiophenecarboxylate

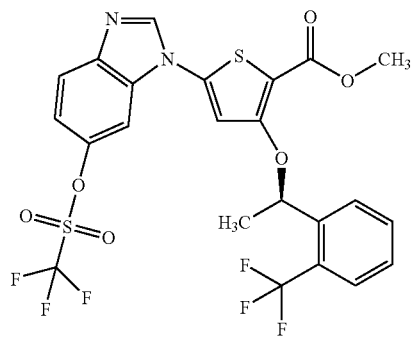

To a stirred, cooled (0° C.) solution of methyl 5-(6-hydroxy-1H-benzimidazol-1-yl)-3-({(1R)-1-[2-(trifluoromethyl)phenyl]ethyl}oxy)-2-thiophenecarboxylate (2.49 g, 5.38 mmol) and n-phenyltrifluoromethane sulfonamide (2.06 g, 5.76 mmol) in DCM (30 mL) was added diisopropylethylamine (2.0 mL, 11.5 mmol). The reaction was allowed to warm to room temperature and stirred for 12 h. The reaction mixture was then concentrated under vacuum, and chromatographed on silica gel (120 g), eluting with a 5-to-40% gradient of EtOAc/hexane to give 3.12 g (98%) of the title compound as a light yellow solid. $^1$H NMR (400 MHz, DMSO-$d_6$): δ 8.76 (s, 1H), 8.01-7.94 (m, 2H), 7.80-7.70 (m, 3H), 7.56-7.43 (m, 3H), 5.98 (q, 1H, J=6.10 Hz), 3.84 (s, 3H), 1.65 (d, 3H, J=6.22 Hz); MS (ESI): 595 [M+H]$^+$.

Step F—3-{(1R)-1-[2-(Trifluoromethyl)phenyl]ethoxy}-5-(6-vinyl-1H-benzimidazol-1-yl)thiophene-2-carboxylate

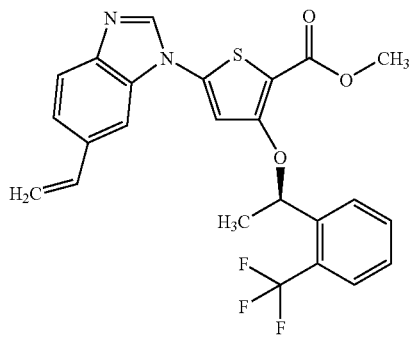

To a mixture of methyl 3-({(1R)-1-[2-(trifluoromethyl)phenyl]ethyl}oxy)-5-(6-{[(trifluoromethyl)sulfonyl]oxy}-1H-benzimidazol-1-yl)-2-thiophenecarboxylate (20.69 g, from a different batch using procedure analogous to Example 3, Route 2, Step E, 34.83 mmol), potassium vinyltrifluoroborate (5.6 g, 42.10 mmol) and triethylamine (4.85 mL, 34.86 mmol), stirred at room temperature in n-propanol (175 mL) was added [1,1'-bis(diphenylphosphino)-ferrocene]dichloropalladium(II) dichloromethane complex (570 mg, 0.70 mmol). The mixture was then heated to reflux and stirred for 3 h, then cooled to room temperature, poured into water and extracted with EtOAc (3×). The combined organic layers were washed with brine, dried over MgSO$_4$, concentrated under vacuum and purified by silica gel chromatography, eluting with a 10-to-50% gradient of EtOAc/hexane to give 12.98 g (79%) of the title compound as a light yellow foam solid. MS (ESI): 473 [M+H]$^+$.

Step G—Methyl 5-[6-(1,2-dihydroxyethyl)-1H-benzimidazol-1-yl]-3-{(1R)-1-[2-(trifluoromethyl)phenyl]ethoxy}thiophene-2-carboxylate

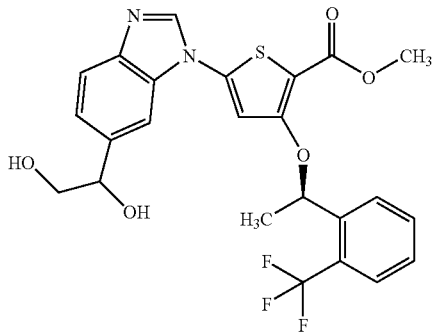

The title compound can be prepared by a procedure analogous to Example 3, Route 1, Step C.

Step H—Methyl 5-(6-formyl-1H-benzimidazol-1-yl)-3-{(1R)-1-[2-(trifluoromethyl)phenyl]ethoxy}thiophene-2-carboxylate

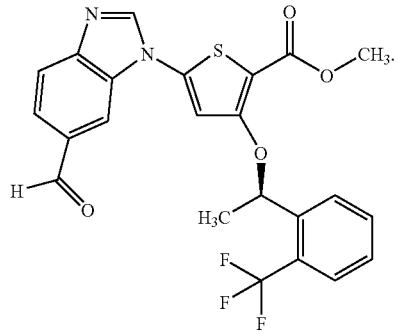

The title compound can be prepared by a procedure analogous to Example 3, Route 1, Step D.

Step I—Methyl 5-{6-[(4-methylpiperazin-1-yl)methyl]-1H-benzimidazol-1-yl}-3-{(1R)-1-[2-(trifluoromethyl)phenyl]ethoxy}thiophene-2-carboxylate

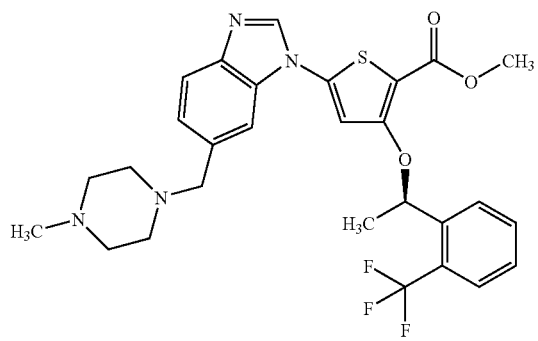

The title compound can be prepared by a procedure analogous to Example 3, Route 1, Step E.

Step J—5-{6-[(4-Methylpiperazin-1-yl)methyl]-1H-benzimidazol-1-yl}-3-{(1R)-1-[2-(trifluoromethyl)phenyl]ethoxy}thiophene-2-carboxamide

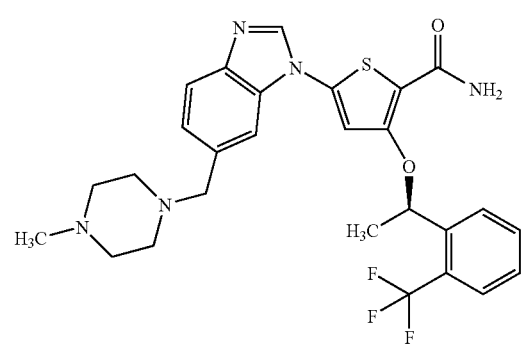

The title compound can be prepared by a procedure analogous to Example 3, Route 1, Step F.

Route 3:

Step A—Methyl 5-{6-[(4-methylpiperazin-1-yl)methyl]-1H-benzimidazol-1-yl}-3-({(1R)-1-[2-(trifluoromethyl)phenyl]ethyl}oxy)thiophene-2-carboxylate

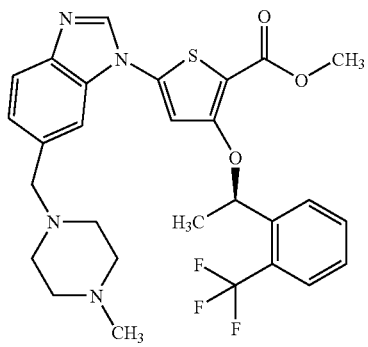

To a stirred, solution of methyl 5-[6-(chloromethyl)-1H-benzimidazol-1-yl]-3-({(1R)-1-[2-(trifluoromethyl)phenyl]ethyl}oxy)thiophene-2-carboxylate (150 mg, 0.30 mmol) in dioxane (1.0 mL) was added N-methylpiperazine (50 µL, 0.45 mmol). The reaction was heated at 60° C. for 18 h, cooled to room temperature and concentrated under vacuum. The residue was dissolved in EtOAc and water. The aqueous layer was extracted with EtOAc. The combined organic layers were washed with brine, dried over sodium sulfate, concentrated under vacuum, and purified by silica gel chromatography eluting with a gradient of 0-to-10% MeOH/DCM, with 1% ammonium hydroxide, to give 134 mg (79%) of the title compound as a white solid. MS (ESI): 559 [M+H]+.

Step B—5-{6-[(4-Methylpiperazin-1-yl)methyl]-1H-benzimidazol-1-yl}-3-{(1R)-1-[2-(trifluoromethyl)phenyl]ethoxy}thiophene-2-carboxamide

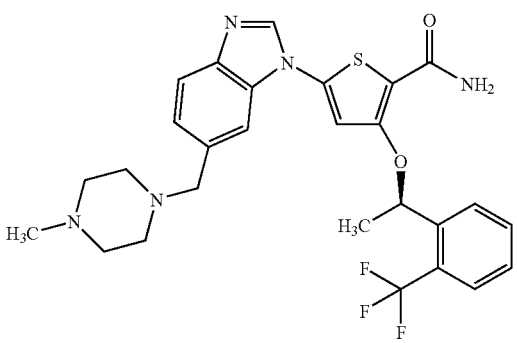

The title compound can be prepared by a procedure analogous to Example 3, Route 1, Step F.

Route 4:

Step A—4-[Bis(methyloxy)methyl]-2-bromo-1-nitrobenzene

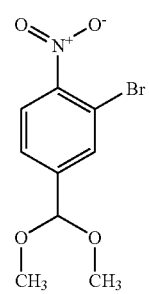

A solution of 3-bromo-4-nitrobenzaldehyde (7.97 g, 34.6 mmol), which was prepared in a manner analogous to the literature procedure (Katritzky, A. R.; Xie, L. *Tetrahedron Letters* 1996, 37, 347-350), trimethyl orthoformate (11.4 mL, 104 mmol), and p-toluenesulfonic acid hydrate (329 mg, 1.73 mmol) in MeOH (69 mL) was refluxed for 3 h. The reaction was then quenched by addition of saturated aqueous ammonium hydroxide (1 mL) and concentrated onto silica gel. Purification by column chromatography (10 to 25% EtOAc: hexanes) provided 8.76 g (92%) of the title compound as an orange oil. $^1$H NMR (300 MHz, CDCl$_3$): δ 7.89 (m, 2H), 7.59 (m, 1H), 5.47 (s, 1H), 3.38 (s, 6H).

Step B—Methyl 5-({5-[bis(methyloxy)methyl]-2-nitrophenyl}amino)-3-({(1R)-1-[2-(trifluoromethyl)phenyl]ethyl}oxy)-2-thiophenecarboxylate

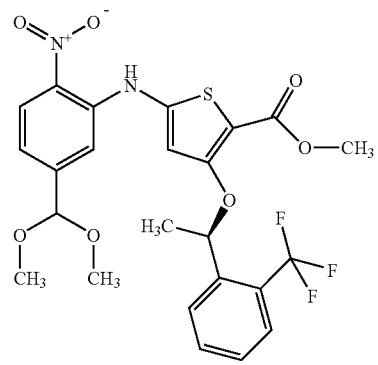

A solution of tris(dibenzylideneacetone) dipalladium(0) (117 mg, 0.127 mmol), 9,9-dimethyl-4,5-bis(diphenylphosphino)xanthene (162 mg, 0.280 mmol), methyl 5-amino-3-({(1R)-1-[2-(trifluoromethyl)phenyl]ethyl}oxy)-2-thiophenecarboxylate (2.31 g, 6.69 mmol), 4-[bis(methyloxy)methyl]-2-bromo-1-nitrobenzene (1.76 g, 6.37 mmol), and cesium carbonate (10.39 g, 31.89 mmol) in 1,4-dioxane (25 mL) was prepared in a round-bottom flask under N$_2$. The flask was evacuated and refilled three times with N$_2$ and then stirred at 60° C. for 16 h. The reaction mixture was then diluted with tetrahydrofuran (100 mL) and concentrated onto silica gel. Purification by column chromatography (5 to 75% EtOAc:hexanes) provided 2.79 g (81%) of the title compound as a red foam. $^1$H NMR (300 MHz, CDCl$_3$): δ 9.63 (br s, 1H), 8.21 (m, 1H), 7.94 (m, 1H), 7.62 (m, 2H), 7.48 (s, 1H), 7.40 (m, 1H), 7.02 (m, 1H), 6.47 (s, 1H), 5.73 (q, 1H, J=6.2 Hz), 3.88 (s, 3H), 3.34 (s, 1H), 3.31 (s, 3H), 3.28 (s, 3H), 1.72 (d, 3H, J=6.2 Hz); MS (ESI): 541 [M+H]+.

Step C—Methyl 5-{6-[bis(methyloxy)methyl]-1H-benzimidazol-1-yl}-3-({(1R)-1-[2-(trifluoromethyl)phenyl]ethyl}oxy)-2-thiophenecarboxylate

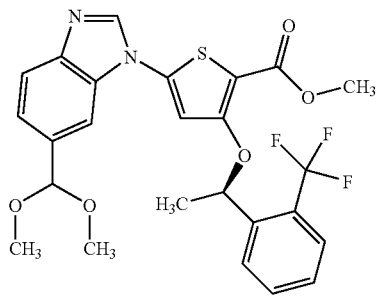

To a solution of methyl 5-({5-[bis(methyloxy)methyl]-2-nitrophenyl}amino)-3-({(1R)-1-[2-(trifluoromethyl)phenyl]ethyl}oxy)-2-thiophenecarboxylate (2.71 g, 5.01 mmol) in trimethyl orthoformate (50 mL) in a Fischer-Porter bottle was added pyridinium p-toluenesulfonate (126 mg, 0.501 mmol) and sulfided platinum on carbon (5 wt % Pt, 977 mg, 0.250 mmol Pt). The mixture was hydrogenated on a Fischer-Porter hydrogenation apparatus at 50 psi of hydrogen until the uptake of hydrogen had ceased (17 h). The reaction mixture was filtered through a sintered glass filter to remove the catalyst, washing with DCM (75 mL). The eluant was concentrated to afford 2.61 g (100%) of the crude title compound as an orange oil, which was carried on to the next step without purification. MS (ESI): 521 [M+H]+.

Step D—Methyl 5-(6-formyl-1H-benzimidazol-1-yl)-3-({(1R)-1-[2-(trifluoromethyl)phenyl]ethyl}oxy)-2-thiophenecarboxylate

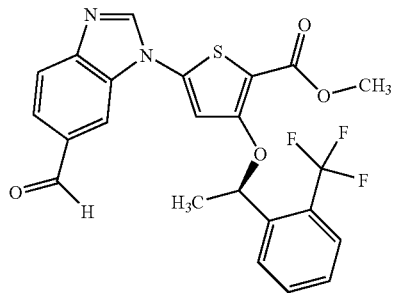

To a solution of crude methyl 5-{6-[bis(methyloxy)methyl]-1H-benzimidazol-1-yl}-3-({(1R)-1-[2-(trifluoromethyl)phenyl]ethyl}oxy)-2-thiophenecarboxylate (2.61 g, 5.01 mmol) (from Step C, above) in acetone (20 mL) and water (5 mL) was added pyridinium p-toluenesulfonate (126 mg, 0.501 mmol). The reaction stirred for 2 h at room temperature and was then poured into water (30 mL) and saturated aqueous NaHCO3 (30 mL). The mixture was extracted with DCM (2×30 mL). The combined organic fractions were dried over sodium sulfate, filtered, and concentrated onto silica gel. Purification by column chromatography (30 to 100% EtOAc:hexanes) provided 1.37 g (58%, 2 steps) of the title compound as a light yellow solid. 1H NMR (300 MHz, CDCl3): δ 10.06 (s, 1H), 8.13 (s, 1H), 7.96-7.88 (m, 4H), 7.72-7.61 (m, 2H), 7.44 (m, 1H), 6.82 (s, 1H), 5.84 (q, 1H, J=6.3 Hz), 3.95 (s, 3H), 1.79 (d, 3H, J=6.3 Hz); MS (ESI): 475 [M+H]+.

Step E—Methyl 5-{6-[(4-methyl-1-piperazinyl)methyl]-1H-benzimidazol-1-yl}-3-({(1R)-1-[2-(trifluoromethyl)phenyl]ethyl}oxy)-2-thiophenecarboxylate

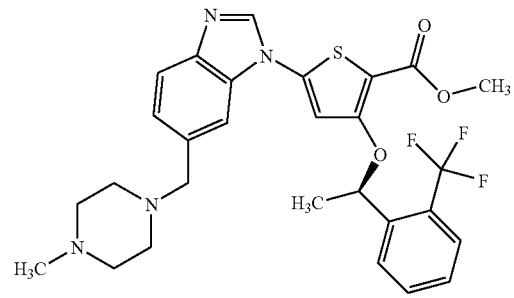

The title compound can be prepared by a procedure analogous to Example 3, Route 1, Step E.

Step F—5-{6-[(4-Methylpiperazin-1-yl)methyl]-1H-benzimidazol-1-yl}-3-{(1R)-1-[2-(trifluoromethyl)phenyl]ethoxy}thiophene-2-carboxamide

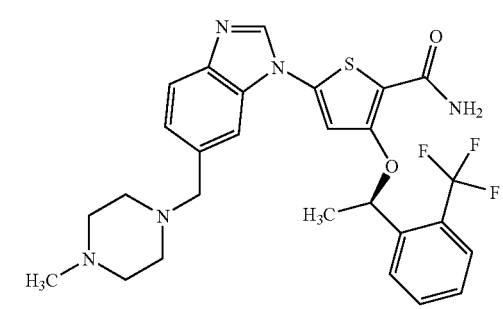

The title compound can be prepared by a procedure analogous to Example 3, Route 1, Step F.

EXAMPLE 4

3-{[(1R)-1-(2-Chlorophenyl)ethyl]oxy}-5-{6-[(4-methylpiperazin-1-yl)methyl]-1H-benzimidazol-1-yl}thiophene-2-carboxamide

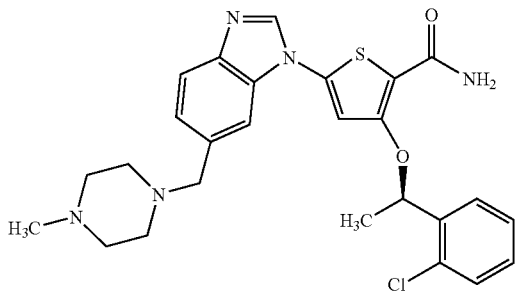

Step A—Methyl 3-{[(1R)-1-(2-chlorophenyl)ethyl]oxy}-5-[(5-{[(2,2-dimethylpropanoyl)oxy]methyl}-2-nitrophenyl)amino]-2-thiophenecarboxylate

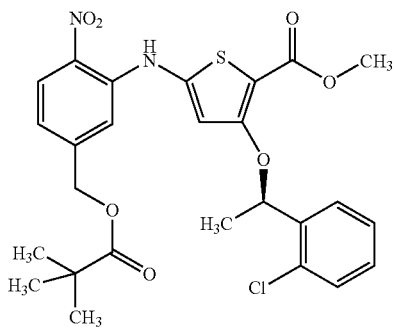

To a mixture of (4-nitro-3-{[(trifluoromethyl)sulfonyl]oxy}phenyl)methyl 2,2-dimethylpropanoate (1.0 g, 2.59 mmol), methyl 5-amino-3-{[(1R)-1-(2-chlorophenyl)ethyl]oxy}-2-thiophenecarboxylate (Intermediate Example 2) (860 mg, 2.75 mmol), tris(dibenzylideneacetone)dipalladium(0) (70.0 mg, 0.076 mmol), and XANTPHOS (90.0 mg, 0.16 mmol) was added toluene (7.0 mL). Stirring was begun, followed by the addition of cesium carbonate (2.95 g, 9.1 mmol). The reaction was heated to 60° C. and stirred for 30 min, then cooled to room temperature, diluted with EtOAc and filtered through Celite, washing the solids with EtOAc and DCM. The filtrate was concentrated under vacuum and chromatographed on silica gel (40 g), eluting with a 5-to-15% gradient of acetone/hexane to give 920 mg (65%) of the title compound as a red solid. $^1$H NMR (400 MHz, DMSO-$d_6$): δ 9.77 (s, 1H), 8.09 (d, 1H, J=8.61 Hz), 7.63 (dd, 1H, J=7.69 and 1.65 Hz), 7.46-7.30 (m, 4H), 7.01 (dd, 1H, J=8.79 and 1.47 Hz), 6.67 (s, 1H), 5.76-5.70 (m, 1H), 5.09 (s, 2H), 3.73 (s, 3H), 1.56 (d, 3H, J=6.23 Hz), 1.14 (s, 9H); MS (ESI): 547 [M+H]$^+$.

Step B—Methyl 5-[(2-amino-5-{[(2,2-dimethylpropanoyl)oxy]methyl}-phenyl)amino]-3-{[(1R)-1-(2-chlorophenyl)ethyl]oxy}-2-thiophenecarboxylate

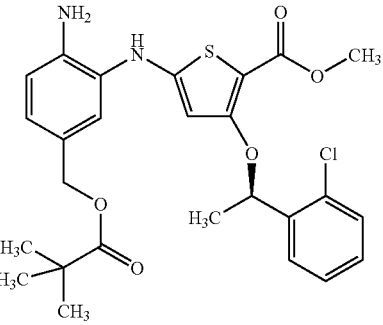

To a high-pressure hydrogenation reaction flask was added methyl 3-{[(1R)-1-(2-chlorophenyl)ethyl]oxy}-5-[(5-{[(2,2-dimethylpropanoyl)oxy]methyl}-2-nitrophenyl)amino]-2-thiophenecarboxylate (6.5 g, from a different batch using procedure analogous to Example 4, Step A, 11.9 mmol), 5% by weight platinum on carbon (sulfided) (2.2 g, 0.56 mmol) and EtOAc (95 mL). The flask was purged with $N_2$ (gas) vacuum (3×), then with $H_2$ (gas) vacuum (3×). Hydrogen gas was then applied at 50 psi for 3 h. The reaction mixture was then filtered through Celite, washing the solids with EtOAc and DCM. The filtrate was then concentrated under vacuum to give 5.46 g (89%) of the title compound as a yellow solid. MS (ESI): 517 [M+H]$^+$.

Step C—Methyl 3-{[(1R)-1-(2-chlorophenyl)ethyl]oxy}-5-(6-{[(2,2-dimethylpropanoyl)oxy]methyl}-1H-benzimidazol-1-yl)-2-thiophenecarboxylate

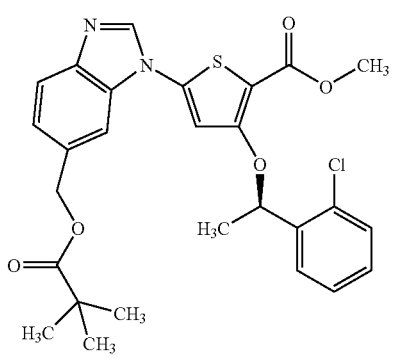

A stirred mixture of methyl 5-[(2-amino-5-{[(2,2-dimethylpropanoyl)oxy]methyl}phenyl)amino]-3-{[(1R)-1-(2-chlorophenyl)ethyl]oxy}-2-thiophenecarboxylate (5.45 g, 10.5 mmol), pyridinium p-toluene sulfonate (265 mg, 1.0 mmol) and triethylorthoformate (15 mL) was heated to 40° C. for 1 h, then cooled to room temperature. The entire mixture was poured onto a silica gel cartridge (25 g) and purified by silica gel chromatography (120 g), eluting with 100% hexanes for 10 min, then a 0-to-10% EtOAc/hexane gradient to give 4.71 g (85%) of the title compound as a yellow solid. MS (ESI): 527 [M+H]$^+$.

Step D—Methyl 3-{[(1R)-1-(2-chlorophenyl)ethyl]oxy}-5-[6-(hydroxymethyl)-1H-benzimidazol-1-yl]-2-thiophenecarboxylate

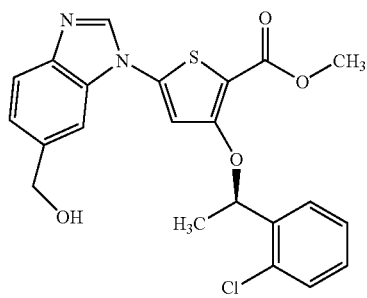

The title compound was prepared from methyl 3-{[(1R)-1-(2-chlorophenyl)ethyl]oxy}-5-(6-{[(2,2-dimethylpropanoyl)oxy]methyl}-1H-benzimidazol-1-yl)-2-thiophenecarboxylate by a procedure analogous to Example 1, Route 1, Step G. MS (ESI): 443 [M+H]⁺.

Step E—Methyl 5-[6-(chloromethyl)-1H-benzimidazol-1-yl]-3-{[(1R)-1-(2-chlorophenyl)ethyl]oxy}-2-thiophenecarboxylate

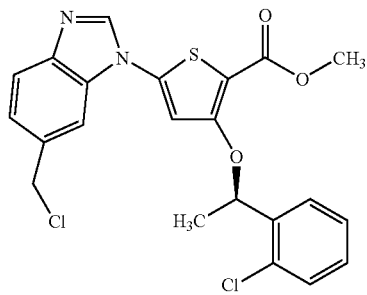

The title compound was prepared from methyl 3-{[(1R)-1-(2-chlorophenyl)ethyl]oxy}-5-[6-(hydroxymethyl)-1H-benzimidazol-1-yl]-2-thiophenecarboxylate by a procedure analogous to Example 1, Route 1, Step H. MS (ESI): 461 [M+H]⁺.

Step F—Methyl 3-{[(1R)-1-(2-chlorophenyl)ethyl]oxy}-5-{6-[(4-methylpiperazin-1-yl)methyl]-1H-benzimidazol-1-yl}thiophene-2-carboxylate

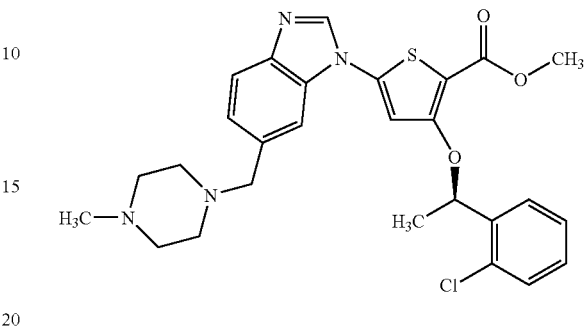

To a stirred mixture of methyl 5-[6-(chloromethyl)-1H-benzimidazol-1-yl]-3-{[(1R)-1-(2-chlorophenyl)ethyl]oxy}-2-thiophenecarboxylate (150 mg, 0.32 mmol) in dioxane (1.5 mL) was added n-methylpiperazine (55 uL, 0.49 mmol) and triethylamine (136 uL, 0.97 mmol). The reaction was then heated at 45° C. for 18 h, cooled to room temperature and concentrated under vacuum. The residue was dissolved in EtOAc (125 mL) and water (50 mL). The aqueous layer was then extracted with EtOAc. The combined organic layers were washed with brine, dried over MgSO₄, concentrated under vacuum and chromatographed on silica gel (4 g), eluting with a 0-to-10% gradient of MeOH/DCM, with 1% ammonium hydroxide, to give 123 mg (72%) of the title compound as a light yellow solid. MS (ESI): 525 [M+H]⁺.

Step G—3-{[(1R)-1-(2-Chlorophenyl)ethyl]oxy}-5-{6-[(4-methylpiperazin-1-yl)methyl]-1H-benzimidazol-1-yl}thiophene-2-carboxamide

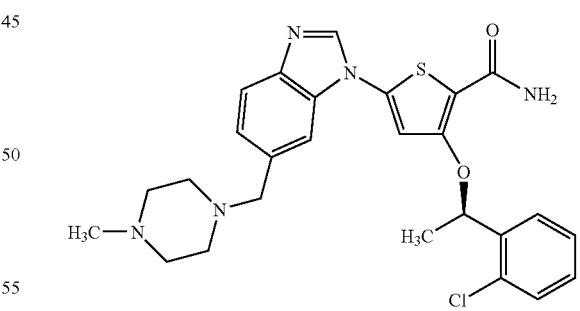

The title compound was prepared from methyl 3-{[(1R)-1-(2-chlorophenyl)ethyl]oxy}-5-{6-[(4-methylpiperazin-1-yl)methyl]-1H-benzimidazol-1-yl}thiophene-2-carboxylate by a procedure analogous to Example 3, Route 1, Step F. ¹H NMR (400 MHz, DMSO-d₆): δ 8.52 (s, 1H), 7.83 (s, 1H), 7.69 (d, 2H, J=8.24 Hz), 7.51-7.34 (m, 4H), 7.28 (d, 1H, J=8.24 Hz), 7.16-7.11 (m, 2H), 5.98 (q, 1H, J=6.35 Hz), 3.55 (s, 2H), 2.42-2.22 (m, 8H), 2.13 (s, 3H), 1.72 (d, 3H, J=6.23 Hz); MS (ESI): 510 [M+H]⁺.

INTERMEDIATE EXAMPLE 4

Methyl 3-{[(1R)-1-(2-chlorophenyl)ethyl]oxy}-5-(6-hydroxy-1H-benzimidazol-1-yl)-2-thiophenecarboxylate

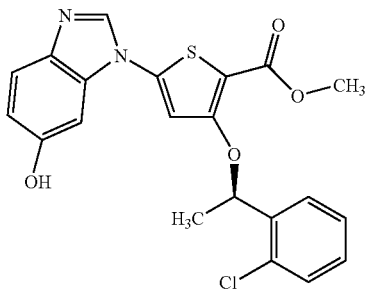

Step A—2-Bromo-4-({[4-(methyloxy)phenyl]methyl}oxy)-1-nitrobenzene

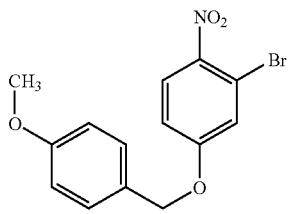

2-Bromo-4-fluoro-1-nitrobenzene (20.0 g, 90.9 mmol) and 4-methoxybenzyl alcohol (22.7 mL, 182 mmol) were dissolved in DCM (400 mL) with stirring. 1N sodium hydroxide solution (400 mL) was added followed by tetrabutylammonium hydrogensulfate (3.09 g, 9.10 mmol). The reaction was stirred for 8 h and poured into a separatory funnel. The layers were separated and the aqueous was extracted once with DCM and once with diethyl ether. The combined organic layers were dried over MgSO$_4$, filtered, and concentrated in vacuo. Purification by flash chromatography afforded 28.01 g (91%) of the title compound. $^1$H NMR (400 MHz, CDCl$_3$): δ 8.03 (d, 1H, J=9.2 Hz), 7.50 (d, 1H, J=2.6 Hz), 7.39-7.34 (m, 2H), 7.17 (dd, 1H, J=2.7, 9.0 Hz), 6.95-6.91 (m, 2H), 5.14 (s, 2H), 3.73 (s, 3H).

Step B—Methyl 3-([(1R)-1-(2-chlorophenyl)ethyl]oxy)-5-{[5-({[4-(methyloxy)phenyl]methyl}oxy)-2-nitrophenyl]amino}-2-thiophenecarboxylate

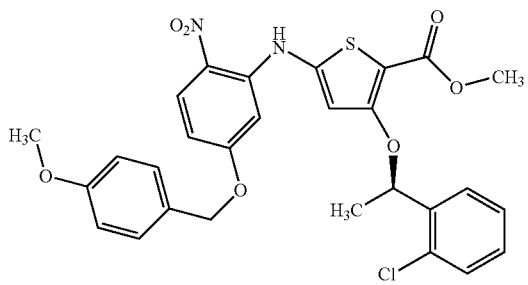

2-Bromo-4-({[4-(methyloxy)phenyl]methyl}oxy)-1-nitrobenzene (20.19 g, 59.7 mmol) and methyl 5-amino-3-{[(1R)-1-(2-chlorophenyl)ethyl]oxy}-2-thiophenecarboxylate (18.60 g, 59.7 mmol) were dissolved in 1,4-dioxane (500 mL) with stirring in a flask equipped with a mechanical stirrer, reflux condenser, and thermometer. The solution was degassed for 75 min by bubbling nitrogen through the stirring solution. 9,9-Dimethyl-4,5-bis(diphenylphosphino)xanthene (1.52 g, 2.63 mmol), cesium carbonate (97.26 g, 299 mmol), and tris(dibenzylideneacetone) dipalladium(0) (1.09 g, 1.19 mmol) were added. The reaction was heated to 60° C. and stirred for 16 h. The reaction was cooled to room temperature and filtered through Celite. The solid was washed with 20% MeOH in DCM. The filtrate was concentrated onto approximately 200 g of silica gel. The solid was placed in a fritted funnel and washed with 10% EtOAc in DCM. The filtrate was concentrated in vacuo. Purification by flash chromatography provided 27.18 g (80%) of the title compound. $^1$H NMR (400 MHz, CDCl$_3$): δ 9.87 (s, 1H), 8.10 (d, 1H, J=9.5 Hz), 7.63 (m, 1H), 7.39-7.29 (m, 4H), 7.23 (m, 1H), 6.96-6.90 (m, 2H), 6.80 (d, 1H, J=2.6 Hz), 6.75 (s, 1H), 6.69 (dd, 1H, J=2.6, 9.3 Hz), 5.75 (q, 1H, J=6.3 Hz), 5.03 (AB, 2H, J$_{AB}$=13.2 Hz, J$_{AB}$=11.3 Hz), 3.74 (s, 3H), 3.74 (s, 3H), 1.55 (d, 3H, J=6.4 Hz).

Step C—Methyl 5-{[2-amino-5-({[4-(methyloxy)phenyl]methyl}oxy)-phenyl]amino}-3-{[(1R)-1-(2-chlorophenyl)ethyl]oxy}-2-thiophenecarboxylate

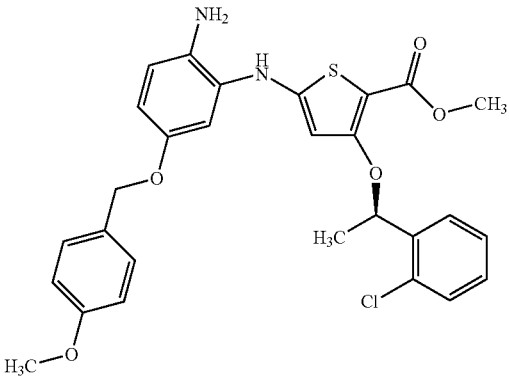

Methyl 3-{[(1R)-1-(2-chlorophenyl)ethyl]oxy}-5-{[5-({[4-(methyloxy)phenyl]-methyl}oxy)-2-nitrophenyl]amino}-2-thiophenecarboxylate (27.18 g, 47.8 mmol) was dissolved in EtOAc (400 mL) with stirring. Sulfided platinum (5% weight on carbon, 2.80 g) was added, and the reaction was placed under 1 atm of H$_2$ using a balloon apparatus. After 36 h an additional amount of catalyst (2.80 g) was added and stirring was continued under 1 atm of hydrogen. After 16 h more, the reaction was filtered through a Celite pad washing with EtOAc. The filtrate was concentrated to afford the title compound, which was immediately carried into the next step. $^1$H NMR (400 MHz, CDCl$_3$): δ 8.66 (br s, 1H), 7.56 (dd, 1H, J=1.7, 7.8 Hz), 7.41-7.09 (m, 5H), 6.93-6.88 (m, 2H), 6.71 (d, 1H, J=2.8 Hz), 6.65 (d, 1H, J=8.6 Hz), 6.57 (dd, 1H, J=2.7, 8.6 Hz), 5.87 (s, 1H), 5.62 (q, 1H, J=6.4 Hz), 4.82 (s, 2H), 4.46 (br s, 2H), 3.73 (s, 3H), 3.64 (s, 3H), 1.52 (d, 3H, J=6.2 Hz).

Step D—Methyl 3-{[(1R)-1-(2-chlorophenyl)ethyl]oxy}-5-[6-({[4-(methyloxy)phenyl]methyl}oxy)-1H-benzimidazol-1-yl]-2-thiophenecarboxylate

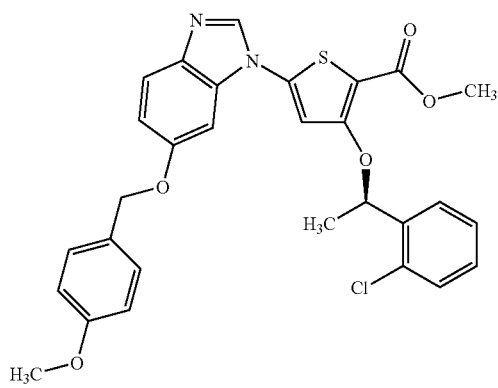

Methyl 5-{[2-amino-5-({[4-(methyloxy)phenyl]methyl}oxy)phenyl]amino}-3-{[(1R)-1-(2-chlorophenyl)ethyl]oxy}-2-thiophenecarboxylate was dissolved in trimethyl orthoformate (100 mL) and diethyl ether (100 mL) with stirring. Pyridinium p-toluenesulfonate (0.601 g, 2.39 mmol) was added in a single portion. The reaction was stirred for 2.5 h and quenched by the addition of triethylamine (approximately 3 mL). The mixture was concentrated and purified by flash chromatography to afford 25.45 g (97% over 2 steps) of the title compound. $^1$H NMR (400 MHz, CDCl$_3$): δ 8.47 (s, 1H), 7.71 (dd, 1H, J=1.6, 8.2 Hz), 7.63 (d, 1H, J=9.0 Hz), 7.43-7.08 (m, 7H), 7.00 (dd, 1H, J=2.4, 8.8 Hz), 6.96-6.90 (m, 2H), 5.97 (q, 1H, J=6.4 Hz), 5.03 (AB, 2H, J$_{AB}$=17.1 Hz, J$_{AB}$=11.3 Hz), 3.80 (s, 3H), 3.73 (s, 3H), 1.60 (d, 3H, J=6.4 Hz).

Step E—Methyl 3-{[(1R)-1-(2-chlorophenyl)ethyl]oxy}-5-(6-hydroxy-1H-benzimidazol-1-yl)-2-thiophenecarboxylate

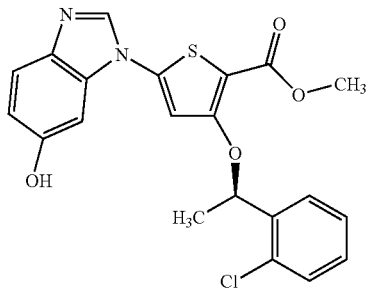

Methyl 3-{[(1R)-1-(2-chlorophenyl)ethyl]oxy}-5-[6-({[4-(methyloxy)phenyl]-methyl}oxy)-1H-benzimidazol-1-yl]-2-thiophenecarboxylate (25.45 g, 46.4 mmol) was dissolved in DCM (120 mL) and cooled to 0° C. with stirring. Trifluoroacetic acid (40.0 mL, 519 mmol) was added dropwise via addition funnel. The reaction was stirred for 1 h and sodium hydroxide (20.0 g, 500 mmol) in water (120 mL) was added dropwise via addition funnel. The pH of the mixture was then adjusted to neutral with saturated NaHCO$_3$ solution. The reaction was poured into a separatory funnel, and the layers were separated. The aqueous layer was washed with EtOAc. The combined organic layers were dried over MgSO$_4$, filtered, and concentrated in vacuo. Purification by flash chromatography afforded 14.86 g (75%) of the title compound. $^1$H NMR (400 MHz, CDCl$_3$): δ 9.62 (s, 1H), 8.45 (s, 1H), 7.74 (dd, 1H, J=1.7, 7.7 Hz), 7.53 (d, 1H, J=8.8 Hz), 7.46-7.38 (m, 3H), 7.32 (m, 1H), 7.08 (d, 1H, J=2.2 Hz), 6.79 (dd, 1H, J=2.2, 8.6 Hz), 5.94 (q, 1H, J=6.2 Hz), 3.79 (s, 3H), 1.60 (d, 3H, J=6.2 Hz).

INTERMEDIATE EXAMPLE 5

Methyl 5-(6-hydroxy-1H-benzimidazol-1-yl)-3-({(1R)-1-[2-(trifluoromethyl)phenyl]ethyl}oxy)-2-thiophenecarboxylate

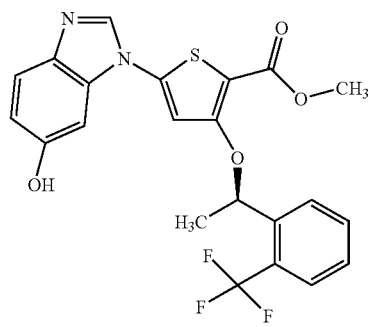

Step A—Methyl 5-{[5-({[4-(methyloxy)phenyl]methyl}oxy)-2-nitrophenyl]amino}-3-({(1R)-1-[2-(trifluoromethyl)phenyl]ethyl}oxy)-2-thiophenecarboxylate

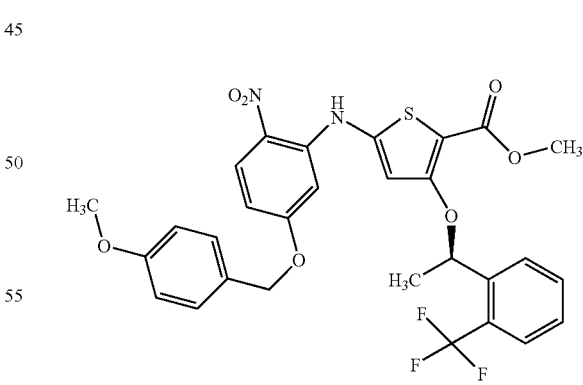

The title compound was prepared from methyl 5-amino-3-({(1R)-1-[2-(trifluoromethyl)phenyl]ethyl}oxy)-2-thiophene carboxylate and 2-bromo-4-({[4-(methyloxy)phenyl]methyl}oxy)-1-nitrobenzene by a procedure analogous to Intermediate Example 4, Step B. MS (ESI): 603 [M+H]$^+$.

Step B—Methyl 5-{[2-amino-5-({[4-(methyloxy) phenyl]methyl}oxy)phenyl]amino}-3-({(1R)-1-[2-(trifluoromethyl)phenyl]ethyl}oxy)-2-thiophenecarboxylate

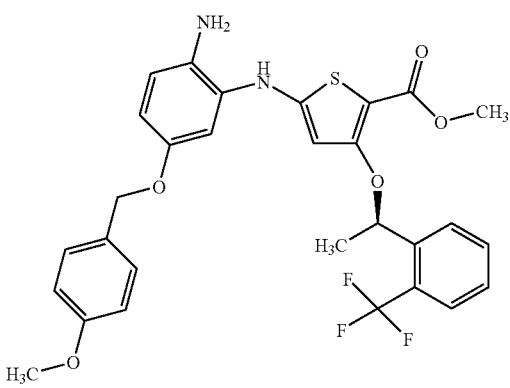

The title compound was prepared from methyl 5-{[5-({[4-(methyloxy)phenyl]methyl}oxy)-2-nitrophenyl]amino}-3-({(1R)-1-[2-(trifluoromethyl)phenyl]ethyl}oxy)-2-thiophenecarboxylate by a procedure analogous to Intermediate Example 4, Step C. MS (ESI): 573 [M+H]⁺.

Step C—Methyl 5-(6-hydroxy-1H-benzimidazol-1-yl)-3-({(1R)-1-[2-(trifluoromethyl)phenyl]ethyl}oxy)-2-thiophenecarboxylate

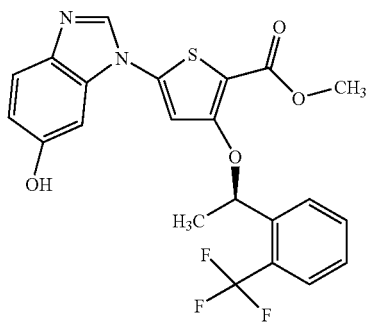

Methyl 5-{[2-amino-5-({[4-(methyloxy)phenyl]methyl}oxy)phenyl]amino}-3-({(1R)-1-[2-(trifluoromethyl)phenyl]ethyl}oxy)-2-thiophenecarboxylate (11 g, 19.19 mmol) was dissolved in 100 mL of trimethyl orthoformate with stirring. Pyridinium ptoluenesulfonate (0.502 g, 1.91 mmol) was added in a single portion. The reaction was stirred for 2.5 h. The mixture was concentrated and the crude methyl 5-[6-({[4-(methyloxy)phenyl]methyl}oxy)-1H-benzimidazol-1-yl]-3-({(1R)-1-[2-(trifluoromethyl)phenyl]ethyl}oxy)-2-thiophenecarboxylate was dissolved in chloroform (75 mL) and cooled to 0° C. with stirring. Trifluoroacetic acid (50.0 mL, 649 mmol) was added. The reaction was stirred for 1 h and allowed to come to room temperature. The mixture was concentrated while cooling to remove most of the trifluoroacetic acid. The mixture was dissolved in chloroform (200 mL). The reaction was poured into a separatory funnel, and the layers were separated. The pH of the mixture was then adjusted to neutral with saturated NaHCO₃ solution. The aqueous layer was washed with chloroform. The combined organic layers were dried over MgSO₄, filtered, and concentrated in vacuo. Purification by flash chromatography afforded 8.16 g (92% over 2 steps) of the title compound. ¹H NMR (400 MHz, CDCl₃): δ 7.88 (d, 1H, J=7.87 Hz), 7.83 (s, 1H), 7.66-7.55 (m, 3H), 7.40 (t, 1H, J=7.7 Hz), 6.92 (d, 1H, J=2.2 Hz), 6.85 (dd, 1H, J=2.3, 8.7 Hz), 5.78 (q, 1H, J=6.23 Hz), 5.47 (s, 1H), 3.91 (s, 3H), 1.75 (d, 3H, J=6.23 Hz); MS (ESI): 463 [M+H]⁺.

EXAMPLE 5

5-[6-(4-Piperidinyloxy)-1H-benzimidazol-1-yl]-3-({(1R)-1-[2-(trifluoromethyl)phenyl]ethyl}oxy)-2-thiophenecarboxamide

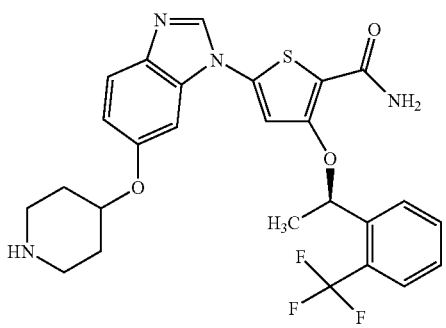

Step A—1,1-Dimethylethyl 4-({1-[5-[(methyloxy)carbonyl]-4-({(1R)-1-[2-(trifluoromethyl)phenyl]ethyl}oxy)-2-thienyl]-1H-benzimidazol-6-yl}oxy)-1-piperidinecarboxylate

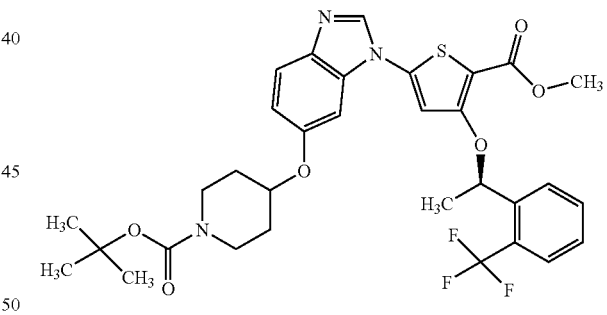

Methyl 5-(6-hydroxy-1H-benzimidazol-1-yl)-3-({(1R)-1-[2-(trifluoromethyl)phenyl]-ethyl}oxy)-2-thiophenecarboxylate (0.478 g, 1.03 mmol), cesium carbonate (0.470 g, 1.44 mmol), and 4-(Toluene-4-sulfonyloxy)-piperidine-1-carboxylic acid tert-butyl ester (0.439 g, 1.24 mmol) were combined in 10 mL of N,N-dimethylformamide and heated to 60° C. with stirring. The reaction was heated for 36 h and cooled to room temperature. The mixture was poured into EtOAc and water, and the layers were separated. The organic layer was washed with brine, and the combined aqueous layers were extracted with EtOAc. The combined organic layers were dried over MgSO₄, filtered, and concentrated in vacuo. Purification by flash chromatography afforded 0.482 g (72%) of the title compound. ¹H NMR (400 MHz, DMSO-d₆) δ 8.43 (s, 1H), 7.95 (dd, J=7.7 Hz, 1H), 7.78-7.66 (m, 2H), 7.63 (d, J=8.8 Hz, 1H), 7.50 (m, 1H), 7.29 (s, 1H), 7.09 (d, J=2.2 Hz, 1H), 7.01 (dd, J=8.8, 2.2 Hz, 1H), 5.97 (q, J=6.2 Hz, 1H), 4.59 (m, 1H), 3.81 (s, 3H), 3.65-3.56 (m, 2H), 3.25-3.15 (m, 2H), 1.91-1.82 (m, 2H), 1.63 (d, J=6.2 Hz, 3H), 1.59-1.49 (m, 2H), 1.38 (s, 9H). MS m/z 646 (M+1).

Step B—Methyl 5-[6-(4-piperidinyloxy)-1H-benzimidazol-1-yl]-3-({(1R)-1-[2-(trifluoromethyl)phenyl]ethyl}oxy)-2-thiophenecarboxylate

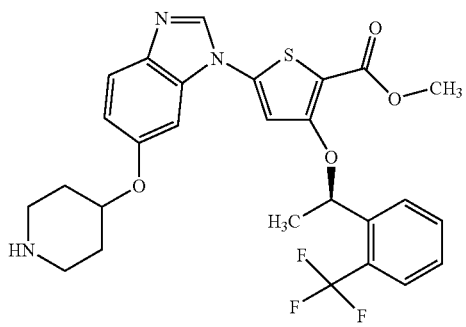

1,1-Dimethylethyl 4-({1-[5-[(methyloxy)carbonyl]-4-({(1R)-1-[2-(trifluoromethyl)phenyl]ethyl}oxy)-2-thienyl]-1H-benzimidazol-6-yl}oxy)-1-piperidinecarboxylate (1.84 g, from a different batch using procedure analogous to Example 5, Step A, 2.85 mmol) was dissolved in 30 mL of DCM with stirring and cooled to 0° C. Trifluoroacetic acid (10.0 mL, 130 mmol) was added dropwise via addition funnel. The reaction was stirred for 1 h, and 2 N sodium hydroxide solution (60 mL) was added dropwise via addition funnel. Saturated aqueous NaHCO$_3$ solution was used to adjust the pH to basic. The mixture was poured into a separatory funnel, and the layers were separated. The aqueous layer was washed once with DCM and once with diethyl ether. The combined organic layers were dried over MgSO$_4$, filtered, and concentrated in vacuo. Purification by flash chromatography provided 1.37 g (88%) of the title compound. $^1$H NMR (400 MHz, DMSO-d$_6$): δ 8.42 (s, 1H), 7.95 (d, J=7.9 Hz, 1H), 7.78-7.67 (m, 2H), 7.61 (d, J=8.6 Hz, 1H), 7.61 (m, 1H), 7.30 (s, 1H), 7.05 (d, J=2.2 Hz, 1H), 6.97 (dd, J=8.8, 2.2 Hz, 1H), 5.96 (q, J=6.1 Hz, 1H), 4.41 (m, 1H), 3.80 (s, 3H), 2.97-2.88 (m, 2H), 2.59-2.49 (m, 2H), 1.92-1.83 (m, 2H), 1.63 (d, J=6.1 Hz, 3H), 1.51-1.38 (m, 2H). MS m/z 546 (M+1).

Step C—5-[6-(4-Piperidinyloxy)-1H-benzimidazol-1-yl]-3-({(1R)-1-[2-(trifluoromethyl)phenyl]ethyl}oxy)-2-thiophenecarboxamide

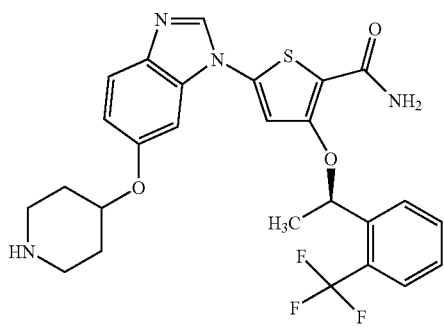

Methyl 5-[6-(4-piperidinyloxy)-1H-benzimidazol-1-yl]-3-({(1R)-1-[2-(trifluoromethyl)phenyl]ethyl}oxy)-2-thiophenecarboxylate (0.154 g, 0.282 mmol) was dissolved in 7 N ammonia in MeOH (12.0 mL, 84.0 mmol) in a sealed tube and heated to 80° C. for 2 days. The reaction was cooled to room temperature and concentrated in vacuo. Purification by flash chromatography afforded 0.129 g (86%) of the title compound. $^1$H NMR (400 MHz, DMSO-d$_6$) δ 8.34 (s, 1H), 7.91 (d, J=8.0 Hz, 1H), 7.81 (br s, 1H), 7.78-7.70 (m, 2H), 7.61 (d, J=8.4 Hz, 1H), 7.53 (m, 1H), 7.12 (brs, 1H), 7.03 (s, 1H), 7.00-6.93 (m, 2H), 5.94 (q, J=6.2 Hz, 1H), 4.44 (m, 1H), 3.03-2.94 (m, 2H), 2.70-2.61 (m, 2H), 1.96-1.86 (m, 2H), 1.72 (d, J=6.2 Hz, 3H), 1.59-1.46 (m, 2H). MS m/z 531 (M+1).

EXAMPLE 6

3-{[(1R)-1-(2-Chlorophenyl)ethyl]oxy}-5-[6-(4-piperidinyloxy)-1H-benzimidazol-1-yl]-2-thiophenecarboxamide

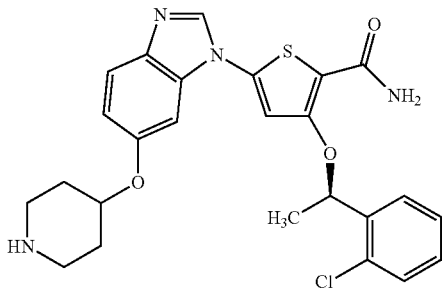

Step A—1,1-Dimethylethyl 4-[(1-{4-{[(1R)-1-(2-chlorophenyl)ethyl]oxy}-5-[(methyloxy)carbonyl]-2-thienyl}-1H-benzimidazol-6-yl)oxy]-1-piperidinecarboxylate

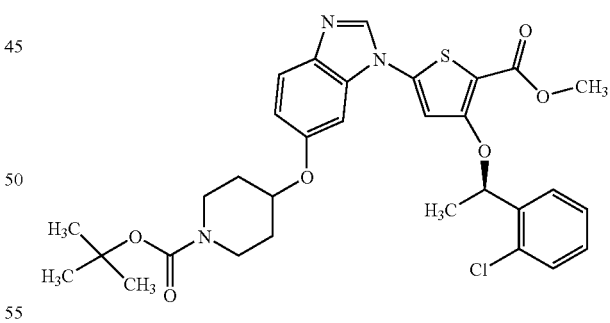

Methyl 3-{[(1R)-1-(2-chlorophenyl)ethyl]oxy}-5-(6-hydroxy-1H-benzimidazol-1-yl)-2-thiophenecarboxylate (2.00 g, 4.66 mmol), triphenylphosphine (4.89 g, 18.6 mmol), and t-butyl 4-hydroxy-1-piperidinecarboxylate (1.88 g, 9.34 mmol) were dissolved in DCM (50 mL) with stirring and cooled to 10° C. Diisopropyl azodicarboxylate (1.84 mL, 9.35 mmol) was added dropwise via syringe. The reaction was stirred for 5 min and allowed to warm to room temperature. The reaction was stirred for 4 h and adsorbed onto silica gel. Purification by flash chromatography afforded the title compound along with small amounts of impurity. $^1$H NMR (400 MHz, DMSO-$d_6$): δ 8.47 (s, 1H), 7.70 (dd, 1H, J=1.6, 7.7 Hz), 7.64 (d, 1H, J=8.8 Hz), 7.44-7.37 (m, 2H), 7.34 (s, 1H), 7.31 (m, 1H), 7.15 (d, 1H, J=2.4 Hz), 7.01 (dd, 1H, J=2.2, 8.8 Hz), 5.97 (q, 1H, J=6.2 Hz), 4.59 (m, 1H), 3.80 (s, 3H), 3.65-3.56 (m, 2H), 3.27-3.14 (m, 2H), 1.92-1.81 (m, 2H), 1.60 (d, 3H, J=6.2 Hz), 1.60-1.47 (m, 2H), 1.38 (s, 9H); MS (ESI): 612 [M+H]$^+$.

Step B—Methyl 3-{[(1R)-1-(2-chlorophenyl)ethyl]oxy}-5-[6-(4-piperidinyloxy)-1H-benzimidazol-1-yl]-2-thiophenecarboxylate

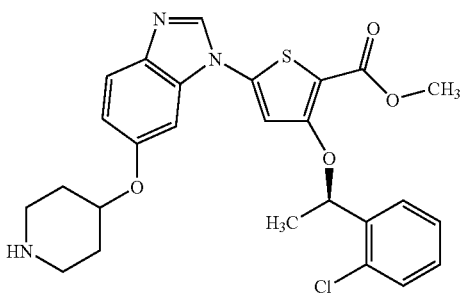

1,1-Dimethylethyl 4-[(1-{4-{[(1R)-1-(2-chlorophenyl)ethyl]oxy}-5-[(methyloxy)-carbonyl]-2-thienyl}-1H-benzimidazol-6-yl)oxy]-1-piperidinecarboxylate was dissolved in DCM (60 mL) and cooled to 0° C. Trifluoroacetic acid (15.0 mL, 195 mmol) was added dropwise via addition funnel. The reaction was stirred for 1.5 h, and 2 N sodium hydroxide solution (88 mL) was added dropwise via addition funnel. Saturated aqueous NaHCO$_3$ solution was used to adjust the pH to ~8. The mixture was poured into a separatory funnel, and the layers were separated. The aqueous layer was washed with DCM (3×) and EtOAc (1×). The combined organic layers were dried over MgSO$_4$, filtered, and concentrated in vacuo. Purification by flash chromatography provided 1.95 g (82% over 2 steps) of the title compound. $^1$H NMR (400 MHz, DMSO-$d_6$): δ 8.46 (s, 1H), 7.71 (dd, 1H, J=1.7, 7.7 Hz), 7.62 (d, 1H, J=8.8 Hz), 7.46-7.38 (m, 2H), 7.35 (s, 1H), 7.32 (m, 1H), 7.09 (d, 1H, J=2.2 Hz), 6.97 (dd, 1H, J=2.2, 8.8 Hz), 5.97 (q, 1H, J=6.2 Hz), 4.42 (m, 1H), 3.80 (s, 3H), 2.96-2.88 (m, 2H), 2.58-2.49 (m, 2H), 1.93-1.84 (m, 2H), 1.60 (d, 3H, J=6.2 Hz), 1.51-1.39 (m, 2H); MS (ESI): 512 [M+1]$^+$.

Step C—3-{[(1R)-1-(2-Chlorophenyl)ethyl]oxy}-5-[6-(4-piperidinyloxy)-1H-benzimidazol-1-yl]-2-thiophenecarboxamide

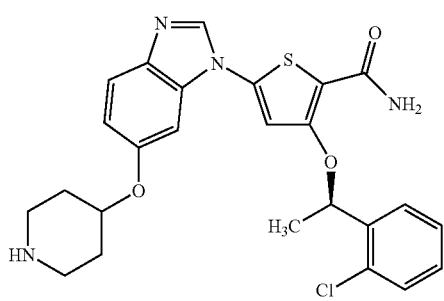

Methyl 3-{[(1R)-1-(2-chlorophenyl)ethyl]oxy}-5-[6-(4-piperidinyloxy)-1H-benzimidazol-1-yl]-2-thiophenecarboxylate (0.150 g, 0.293 mmol) was dissolved in 7 N ammonia in MeOH (12.0 mL, 84.0 mmol) in a sealed tube and heated to 80° C. for 48 h. The solution was concentrated down and recharged with fresh 7 N ammonia in MeOH (12.0 mL, 84.0 mmol) and heated to 110° C. for 72 h. The reaction was cooled to room temperature and concentrated in vacuo. Purification by flash chromatography afforded 0.126 g (87%) of the title compound. $^1$H NMR (400 MHz, DMSO-$d_6$): δ 8.38 (s, 1H), 7.79 (br s, 1H), 7.66 (dd, 1H, J=1.6, 7.7 Hz, 1H), 7.61 (d, 1H, J=8.8 Hz), 7.45 (dd, 1H, J=1.3, 7.8 Hz), 7.40 (m, 1H), 7.84 (m, 1H), 7.11 (s, 1H), 7.11 (br s, 1H), 7.01 (d, 1H, J=2.2 Hz), 6.96 (dd, 1H, J=2.3, 8.7 Hz), 5.98 (q, 1H, J=6.2 Hz), 4.41 (m, 1H), 2.98-2.89 (m, 2H), 2.62-2.53 (m, 2H), 1.94-1.84 (m, 2H), 1.70 (d, 3H, J=6.2 Hz), 1.54-1.40 (m, 2H); MS (ESI): 497 [M+H]$^+$.

EXAMPLE 7

5-{6-[(1-Methyl-4-piperidinyl)oxy]-1H-benzimidazol-1-yl}-3-({(1R)-1-[2-(trifluoromethyl)phenyl]ethyl}oxy)-2-thiophenecarboxamide

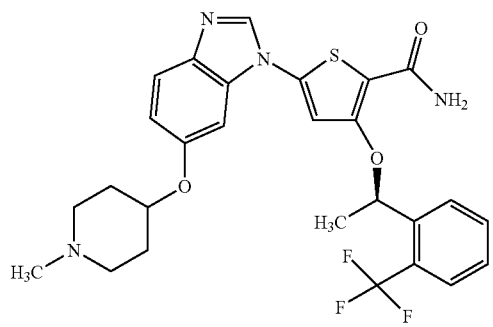

Step A—Methyl 5-{6-[(1-methyl-4-piperidinyl)oxy]-1H-benzimidazol-1-yl}-3-({(1R)-1-[2-(trifluoromethyl)phenyl]ethyl}oxy)-2-thiophenecarboxylate

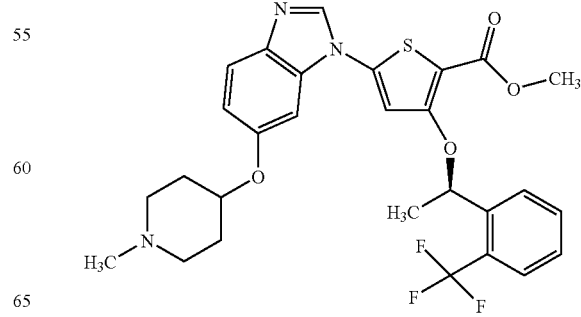

Methyl 5-[6-(4-piperidinyloxy)-1H-benzimidazol-1-yl]-3-({(1R)-1-[2-(trifluoromethyl)phenyl]ethyl}oxy)-2-thiophenecarboxylate (0.200 g, 0.367 mmol) was dissolved in DCM (4 mL) and MeOH (2 mL). Acetic acid (0.025 mL, 0.44 mmol) and formaldeldehyde (0.055 mL, 37% in water, 0.74 mmol) were added via syringe. Sodium triacetoxyborohydride (0.117 g, 0.552 mmol) was added in a single portion. The reaction was stirred for 1 h and quenched with saturated NaHCO₃ solution. The mixture was poured into DCM and half-saturated aqueous NaHCO₃. The layers were separated, and the aqueous layer was washed with DCM (3×) and EtOAc (1×). The combined organic layers were dried over MgSO₄, filtered, and concentrated in vacuo. Purification by flash chromatography afforded 0.150 g (73%) of the title compound. $^1$H NMR (400 MHz, DMSO-d₆): δ 8.43 (s, 1H), 7.96 (d, J=7.7 Hz, 1H), 7.78-7.68 (m, 2H), 7.62 (d, J=9.0 Hz, 1H), 7.51 (m, 1H), 7.32 (s, 1H), 7.06 (br s, 1H), 6.98 (m, 1H), 5.97 (q, J=6.0 Hz, 1H), 4.41 (m, 1H), 3.80 (s, 3H), 3.26 (s, 3H), 2.52-2.43 (m, 2H), 2.27-2.11 (m, 2H), 1.98-1.85 (m, 2H), 1.73-1.60 (m, 2H), 1.62 (d, J=6.0 Hz, 3H). MS (ESI): 560 [M+H]⁺.

Step B—5-{6-[(1-Methyl-4-piperidinyl)oxy]-1H-benzimidazol-1-yl}-3-({(1R)-1-[2-(trifluoromethyl)phenyl]ethyl}oxy)-2-thiophenecarboxamide

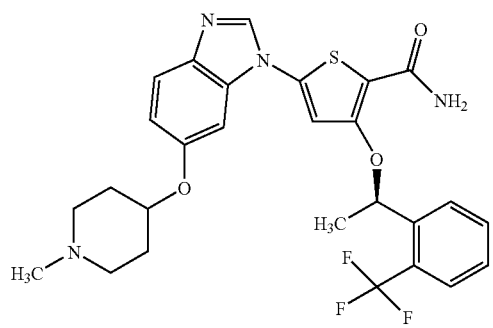

Methyl 5-{6-[(1-methyl-4-piperidinyl)oxy]-1H-benzimidazol-1-yl}-3-({(1R)-1-[2-(trifluoromethyl)phenyl]ethyl}oxy)-2-thiophenecarboxylate (0.148 g, 0.264 mmol) was dissolved in 7 N ammonia in MeOH (12.0 mL, 84.0 mmol) in a sealed tube and heated to 80° C. for 24 hours. The reaction was cooled to room temperature and concentrated in vacuo. Purification by flash chromatography afforded 0.138 g (96%) of the title compound. $^1$H NMR (400 MHz, DMSO-d₆): δ 8.35 (s, 1H), 7.92 (d, J=7.7 Hz, 1H), 7.82 (br s, 1H), 7.80-7.71 (m, 2H), 7.64-7.51 (m, 2H), 7.12 (brs, 1H), 7.06 (s, 1H), 6.99-6.94 (m, 2H), 5.95 (q, J=6.2 Hz, 1H), 4.36 (m, 1H), 2.64-2.53 (m, 2H), 2.23-2.11 (m, 2H), 2.17 (s, 3H), 1.94-1.84 (m, 2H), 1.73 (d, J=6.2 Hz, 3H), 1.71-1.57 (m, 2H). MS (ESI): 545 [M+H]⁺.

EXAMPLE 8

3-{[(1R)-1-(2-Chlorophenyl)ethyl]oxy}-5-{6-[(1-methyl-4-piperidinyl)oxy]-1H-benzimidazol-1-yl}-2-thiophenecarboxamide

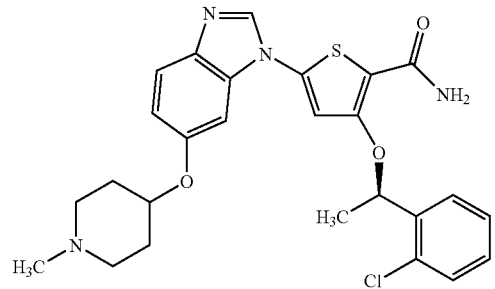

Step A—Methyl 3-{[(1R)-1-(2-chlorophenyl)ethyl]oxy}-5-{6-[(1-methyl-4-piperidinyl)oxy]-1H-benzimidazol-1-yl}-2-thiophenecarboxylate

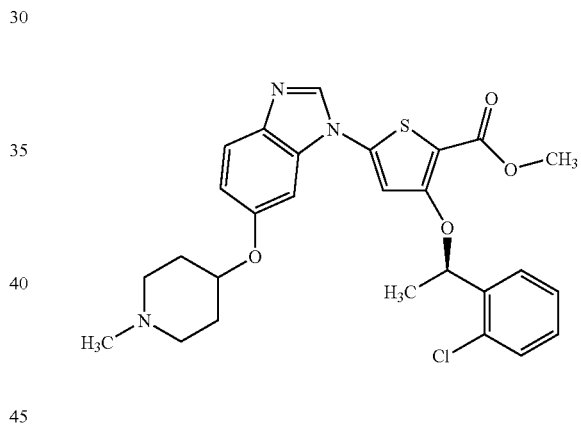

Methyl 3-{[(1R)-1-(2-chlorophenyl)ethyl]oxy}-5-[6-(4-piperidinyloxy)-1H-benzimidazol-1-yl]-2-thiophenecarboxylate (0.260 g, 0.508 mmol) was dissolved in DCM (4 mL) and MeOH (2 mL). Acetic acid (0.035 mL, 0.61 mmol) and formaldeldehyde (0.076 mL, 37% in water, 1.0 mmol) were added via syringe. Sodium triacetoxyborohydride (0.161 g, 0.760 mmol) was added in a single portion. The reaction was stirred for 2 h and poured into DCM and half-saturated aqueous NaHCO₃. The layers were separated, and the aqueous layer was washed with DCM and EtOAc. The combined organic layers were dried over MgSO₄, filtered, and concentrated in vacuo. Purification by flash chromatography afforded 0.215 g (80%) of the title compound. $^1$H NMR (400 MHz, DMSO-d₆): δ 8.48 (s, 1H), 7.73 (dd, 1H, J=1.8, 7.7 Hz), 7.63 (d, 1H, J=8.8 Hz), 7.47-7.40 (m, 2H), 7.38 (s, 1H), 7.34 (m, 1H), 7.12 (d, 1H, J=2.2 Hz), 6.99 (dd, 1H, J=2.2, 8.8 Hz), 5.98 (q, 1H, J=6.2 Hz), 4.41 (m, 1H), 3.80 (s, 3H), 2.65-2.54 (m, 2H), 2.24-2.13 (m, 2H), 2.17 (s, 3H), 1.97-1.87 (m, 2H), 1.72-1.61 (m, 2H), 1.62 (d, 3H, J=6.2 Hz); MS (ESI): 526 [M+H]⁺.

Step B—3-{[(1R)-1-(2-Chlorophenyl)ethyl]oxy}-5-{6-[(1-methyl-4-piperidinyl)oxy]-1H-benzimidazol-1-yl}-2-thiophenecarboxamide

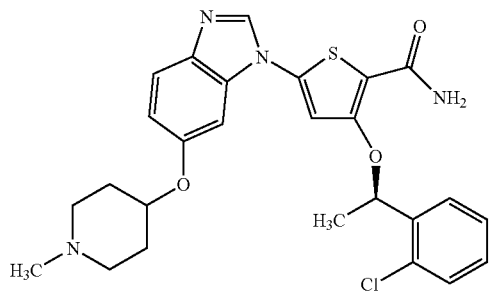

Methyl 3-{[(1R)-1-(2-chlorophenyl)ethyl]oxy}-5-{6-[(1-methyl-4-piperidinyl)oxy]-1H-benzimidazol-1-yl}-2-thiophenecarboxylate (0.214 g, 0.407 mmol) was dissolved in 7 N ammonia in MeOH (12.0 mL, 84.0 mmol) in a sealed tube and heated to 80° C. for 2.5 days. The reaction was cooled to room temperature and concentrated in vacuo. Purification by flash chromatography afforded 0.208 g (100%) of the title compound. $^1$H NMR (400 MHz, DMSO-$d_6$): δ 8.39 (s, 1H), 7.80 (br s, 1H), 7.67 (dd, 1H, J=1.5, 7.6 Hz), 7.62 (d, 1H, J=8.6 Hz), 7.45 (m, 1H), 7.41 (m, 1H), 7.34 (m, 1H), 7.13 (s, 1H), 7.11 (br s, 1H), 7.02 (d, 1H, J=2.0 Hz), 6.97 (dd, 1H, J=2.2, 8.8 Hz), 5.99 (q, 1H, J=6.2 Hz), 4.37 (m, 1H), 2.63-2.53 (m, 2H), 2.22-2.14 (m, 2H), 2.17 (s, 3H), 1.95-1.86 (m, 2H), 1.71 (d, 3H, J=6.2 Hz), 1.70-1.59 (m, 2H); MS (ESI): 511 [M+H]$^+$.

COMPARATIVE EXAMPLES

Comparative Example numbers 121, 126, 127, 136 and 143 can be prepared using methods known in the art, including those described in PCT Publication No. WO2004/014899 to SmithKline Beecham Corp.

| Number | Structure |
|---|---|
| 121 | 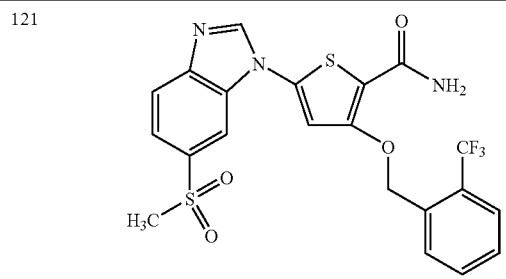 |
| 126 | 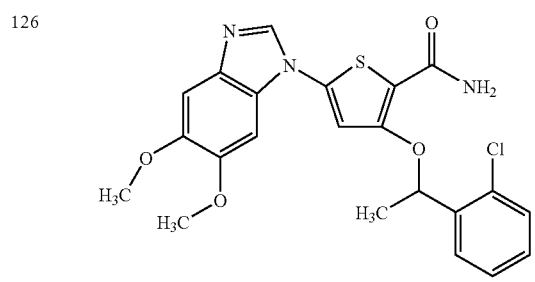 |
| 127 | 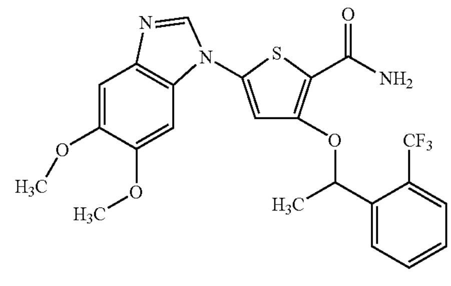 |
| 136 | 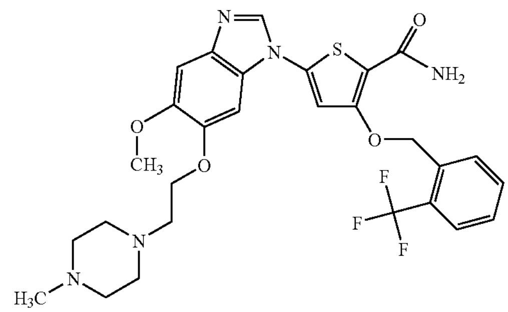 |
| 143 | 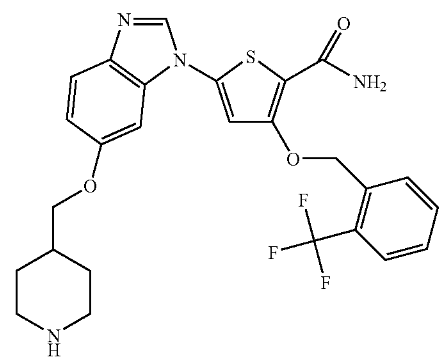 |

BIOLOGICAL EXAMPLES

I. Assay for Inhibition of PLK1

A. Preparation of 6×N-terminal His-tagged PLK kinase domain

6×N-terminal His-tagged PLK kinase domain (amino acids 21-346 proceeded by MKKGHHHHHHD) SEQ ID: No. 1. was prepared from baculovirus infected *T. ni* cells under polyhedrin promoter control. All procedures were performed at 4° C. Cells were lysed in 50 mM HEPES, 200 mM NaCl, 50 mM imidazole, 5% glycerol; pH 7.5. The homogenate was centrifuged at 14K rpm in a SLA-1500 rotor for 1 h and the supernatant filtered through a 1.2 micron filter. The supernatant was loaded onto a Nickel chelating Sepharose (Amersham Pharmacia) column and washed with lysis buffer. Protein was eluted using 20%, 30% and 100% buffer B steps where buffer B is 50 mM HEPES, 200 mM NaCl, 300 mM imidazole, 5% glycerol; pH 7.5. Fractions containing PLK were determined by SDS-PAGE. Fractions containing PLK were diluted five-fold with 50 mM HEPES, 1 mM DTT, 5% glycerol; pH 7.5, then loaded on an SP Sepharose (Amersham Pharmacia) column. After washing the column with 50 mM HEPES, 1 mM DTT, 5% glycerol; pH 7.5, PLK was step eluted with 50 mM HEPES, 1 mM DTT, 500 mM NaCl; 5% glycerol; pH 7.5. PLK was concentrated using a 10 kDa molecular weight cutoff membrane and then loaded onto a Superdex 200 gel filtration (Amersham Pharmacia) column equilibrated in 25 mM HEPES, 1 mM DTT, 500 mM NaCl, 5% glycerol; pH 7.5. Fractions containing PLK were determined by SDS-PAGE. PLK was pooled, aliquoted and stored at −80° C. Samples were quality controlled using mass spectrometry, N-terminal sequencing and amino acid analysis.

B. Enzyme activity +/− inhibitors was determined as follows:

All measurements were obtained under conditions where signal production increased linearly with time and enzyme. Test compounds were added to white 384-well assay plates (0.1 μL for 10 μL and some 20 μL assays, 1 μL for some 20 μL assays) at variable known concentrations in 100% DMSO. DMSO (1-5% final, as appropriate) and EDTA (65 mM in reaction) were used as controls. Reaction Mix was prepared as follows at 22° C.:

25 mM HEPES, pH 7.2
15 mM MgCl2
1 μM ATP
0.05 μCi/well $^{33}$P-γ ATP (10Ci/mMol)
1 μM substrate peptide (Biotin-Ahx-SFNDTLDFD) SEQ ID:No. 2.
0.15 mg/mL BSA
1 mM DTT
2 nM PLK1 kinase domain (added last)

Reaction Mix (10 or 20 μL) was quickly added to each well immediately following addition of enzyme via automated liquid handlers and incubated 1-1.5 h at 22° C. The 20 μL enzymatic reactions were stopped with 50 μL of stop mix (50 mM EDTA, 4.0 mg/ml Streptavidin SPA beads in Standard Dulbecco's PBS (without $Mg^{2+}$ and $Ca^{2+}$), 50 mM ATP) per well. The 10 μL reactions were stopped with 10 μL of stop mix (50 mM EDTA, 3.0 mg/mL Streptavidin-coupled SPA Imaging Beads ("LeadSeeker") in Standard Dulbecco's PBS (without $Mg^{2+}$ and $Ca^{2+}$), 50 μM ATP) per well. Plates were sealed with clear plastic seals, spun at 500×g for 1 min or settled overnight, and counted in Packard TopCount for 30 seconds/well (regular SPA) or imaged using a Viewlux imager (LeadSeeker SPA). Signal above background (EDTA controls) was converted to percent inhibition relative to that obtained in control (DMSO-only) wells.

C. Results

The data are reported in Table 1 below. In Table 1, +=$pIC_{50}$<6; ++=$gpIC_{50}$ 6-8; +++=$pIC_{50}$>8.

II. Methylene Blue Growth Inhibition Assay—Inhibition of Cell Proliferation by PLK1 Inhibitors Generally, exponentially growing cell lines of different tumor origins, cultured in appropriate media containing 10% fetal bovine serum at 37° C. in a 5% $CO_2$ incubator were plated at low density (less than 2000 cells/well) in 96-well plates. Twenty four hours post-plating, cells were treated with different concentrations of test compounds ranging from 10 uM to 0.04 nM. Several wells were left untreated as a control. Seventy two hours post-treatment, cell numbers were determined using 10 μl per well of methylene blue (Sigma M9140) (0.5% in 50:50 Ethanol:water). Stain was incubated at room temperature for 30 minutes before plates were rinsed and dye solubilized in 1% N-lauroyl sarcosine, sodium salt, (Sigma L5125, in PBS) (further details of a methylene blue assay are described below). Plates were read on a microplate reader, measuring the OD at 620 nm.

Percent inhibition of cell growth was expressed as percent proliferation relative to 100% proliferation (control). Concentration of test compound that inhibited 50% of cell growth ($IC_{50}$) was determined by 4 parameter fit of data using XLfit, (value of no cell control was subtracted from all samples for background). The data are shown in Table 1 below and represent a compilation of several different experiments, each performed using the general parameters outlined above, although minor variations may have been employed in some instances.

In one assay, normal human foreskin fibroblasts (HFF), human colon (HCT116, RKO), lung (H460, A549) and breast (MCF7) tumor cell lines were cultured in high glucose DMEM (Life Technologies) containing 10% fetal bovine serum (FBS) at 37° C. in a humidified 5% $CO_2$, 95% air incubator. Cells were harvested using trypsin/EDTA, counted using a haemocytometer, and plated in 100 μL of culture media per well, at the following densities, in a 96-well tissue culture plate (Falcon 3075): HFF 5,000 cells/well, HCT116 3,000 cells/well, RKO 2,500 cells/well, H460 2,500 cells/well, A549 5,000 cells/well, MCF7 4,000 cells/well. The next day, compounds were diluted in low glucose DMEM containing 100 μg/mL gentamicin, at twice the final required concentration, from 10 mM stock solutions in DMSO. 100 μL/well of these dilutions were added to the 100 μL of media currently in the assay plates. Medium containing 0.6% DMSO was added to control wells. The final concentration of DMSO in all wells was 0.3%. Cells were incubated at 37° C., 5% $CO_2$ for 72 h. Medium was removed by aspiration. Cell biomass was estimated by staining cells with 80 μL per well methylene blue (Sigma M9140, 0.5% in 50:50 ethanol:water), and incubation at room temperature for 30-60 min. Stain was removed by aspiration and the plates rinsed by immersion in water, then air-dried. To release stain from the cells, 100 μL of solubilization solution was added (1% N-lauroyl sarcosine, Sodium salt, Sigma L5125, in PBS), and plates were shaken gently for about 30 min. Optical density at 620 nM was measured on a microplate reader. Percent inhibition of cell growth was calculated relative to vehicle treated control wells. Concentration of compound that inhibits 50% of cell growth ($IC_{50}$) was interpolated using nonlinear regression (Levenberg-Marquardt) and the equation, $y=V_{max}*(1-(x/(K+x)))+Y2$, where "K" was equal to the $IC_{50}$.

The data are reported in Table 1 below. In Table 1, +=$IC_{50}$>1μM; ++=$IC_{50}$ 0.1-1 μM: +++=$IC_{50}$<0.1 μM.

III. Determination of Protein Binding to Human Plasma Proteins Using Equilibrium Dialysis 96 Well Plate (High Throughput Dialysis): Stock solutions of compounds were spiked into human plasma at a target concentration of 2000 ng/mL. The mixture was inverted gently several times to insure homogeneity and triplicate 50 μL aliquots were collected to verify initial concentrations. Following assembly of dialysis plate (HTDialysis membrane strips, molecular weight cut off limit of 12,000-14,000 daltons), spiked plasma (150 μL) was placed in the donor compartment of the well and Phosphate Buffered Saline pH 7.4 (150 μL) in the receiver compartment. Eight wells were set up per compound and plasma type. Plate was placed in a 37° C. incubator on a plate shaker. Following the 6 h incubation period, the plate was removed. Single 50 μL aliquots from each donor and receiver compartment (per well) were analyzed. Sample analysis was by LC/MS/MS (results reported as Drug Peak Area/Internal Standard Peak Area ratios). Protein binding assay can also be performed using dialysis cells instead of HT Dialysis 96 well plates. The data are reported in Table 1 below. In Table 1, % Protein Binding, +=>98%; ++=95-98%: +++=<95%.

IV. High Throughput Solubility Assay

Two samples are prepared for each compound. One (the standard sample) contains the compound at a fixed concentration of 20 μM in an aqueous/organic mixed solvent cocktail. The other (the test sample) contains the compound at a maximum concentration of 200 μM in pH 7.4, 0.05M phosphate buffer and shaking for 24 h. The test sample is filtered by 0.45μ filter and then spun for 10 min to remove any undissolved solid. HPLC analyses are preformed on these samples. The peak areas are used for computing solubility. The data are reported in Table 1 below. In Table 1, solubility, +=<30 μM; ++=30-100 μM: +++=>100 μM.

Plates were incubated at room temperature for 15 minutes and the chemiluminescent signal was read on the Victor V or Envison 2100 reader.

Percent inhibition of cell growth was expressed as percent proliferation relative to 100% proliferation (control). Concentration of test compound that inhibited 50% of cell growth ($IC_{50}$) was determined by 4 parameter fit of data using XLfit, (value of no cell control was subtracted from all samples for background). The Cell-Titer Glo data are shown in Table 2 below and represent a compilation of several different experiments, each performed using the general parameters outlined above, although minor variations may have been employed in some instances. In Table 2, $+=IC_{50}>1$ μM; $++=IC_{50}$ 0.5-1 μM: $+++=IC_{50}<0.5$ μM.

TABLE 1

| Example # | PLK1 $pIC_{50}$ | HCT116 $IC_{50}$ (μM) | H460 $IC_{50}$ (μM) | MCF7 $IC_{50}$ (μM) | A549 $IC_{50}$ (μM) | RKO $IC_{50}$ (μM) | HFF $IC_{50}$ (μM) | % Protein Binding | Solubility (μM) |
|---|---|---|---|---|---|---|---|---|---|
| 1 | +++ | +++ | +++ | +++ | +++ | +++ | ++ | ++ | ++ |
| 2 | +++ | +++ | +++ | +++ | +++ | +++ | ++ | ++ | ++ |
| 3 | +++ | +++ | +++ | +++ | +++ | +++ | +++ | +++ | +++ |
| 4 | +++ | +++ | +++ | +++ | +++ | +++ | +++ | ND | +++ |
| 5 | +++ | +++ | +++ | +++ | +++ | +++ | ++ | ++ | +++ |
| 6 | +++ | +++ | +++ | ND | +++ | +++ | ++ | +++ | +++ |
| 7 | +++ | +++ | +++ | +++ | +++ | +++ | ++ | +++ | +++ |
| 8 | +++ | +++ | +++ | ND | +++ | +++ | +++ | +++ | +++ |
| Com. Ex 127 | +++ | ++ | +++ | ++ | +++ | +++ | + | + | + |
| Com. Ex 126 | +++ | +++ | +++ | + | +++ | +++ | ++ | + | ND |
| Com. Ex 121 | ++ | + | + | + | + | + | + | ++ | ND |
| Com. Ex 136 | ++ | ++ | ++ | ++ | ND | ++ | + | +++ | ND |
| Com. Ex 143 | ++ | ++ | + | ++ | + | ++ | + | +++ | + |

ND: Not Determined

Table 1 shows that the instantly claimed compounds possess superior properties over the comparative examples tested. For example, example compounds 1-8 have superior enzyme and cell potency over comparative examples 121, 136 and 143 in PLK1 enzyme assay and methylene blue cell proliferation assay in multiple cell lines examined. Example compounds 1-8 have superior solubility in pH 7.4, 0.05 M phosphate buffer over comparative example 127. Example compounds 1-3 and 5-8 have superior protein binding in human serum by equilibrium dialysis assay over comparative example 126 and 127.

V. Cell-Titer-Glo—Inhibition of Cell Proliferation by PLK1 Inhibitors

Exponentially growing cell lines of different tumor origins, cultured in appropriate media containing 10% fetal bovine serum at 37° C. in a 5% $CO_2$ incubator were plated at low density (less than 2000 cells/well) in 96-well plates. Twenty four hours post-plating, cells were treated with different concentrations of test compounds ranging from 10 uM to 0.04 nM. Several wells were left untreated as a control. Seventy two hours post-treatment, cell numbers were determined using 50-100 ul per well of CellTiter-Glo (Promega #G7573).

TABLE 2

| Cell Line | Ex 1 | Ex 2 | Ex 3 | Ex 4 | Ex 5 | Ex 6 | Ex 7 | Ex 8 |
|---|---|---|---|---|---|---|---|---|
| HCT116 $IC_{50}$ | ND | ND | +++ | ND | +++ | ND | ND | ND |
| A549-L $IC_{50}$ | ND | ND | +++ | ND | +++ | ND | ND | ND |
| COLO205 $IC_{50}$ | ND | ND | +++ | ND | +++ | ND | ND | ND |
| HT29 $IC_{50}$ | ND | ND | +++ | ND | +++ | ND | ND | ND |
| MX-1 $IC_{50}$ | ND | ND | +++ | ND | +++ | ND | ND | ND |
| SKOV-3 $IC_{50}$ | ND | ND | +++ | ND | +++ | ND | ND | ND |
| LNCaP $IC_{50}$ | ND | ND | +++ | ND | ND | ND | ND | ND |
| P388 $IC_{50}$ | ND | ND | +++ | ND | ND | ND | ND | ND |
| H1299 $IC_{50}$ | ND | ND | +++ | ND | +++ | ND | ND | ND |
| Hela $IC_{50}$ | ND | ND | +++ | ND | ND | ND | ND | ND |
| HN5 $IC_{50}$ | ND | ND | +++ | ND | ND | ND | ND | ND |
| MCF7 $IC_{50}$ | ND | ND | +++ | ND | +++ | ND | ND | ND |
| MV522 $IC_{50}$ | ND | ND | +++ | ND | ND | ND | ND | ND |
| MDA-MB-468 $IC_{50}$ | ND | ND | +++ | ND | +++ | ND | ND | ND |
| PANC-1 $IC_{50}$ | ND | ND | +++ | ND | ND | ND | ND | ND |
| MiaPaca $IC_{50}$ | ND | ND | +++ | ND | ND | ND | ND | ND |
| ASPC3 $IC_{50}$ | ND | ND | +++ | ND | ND | ND | ND | ND |
| BXPC3 $IC_{50}$ | ND | ND | +++ | ND | ND | ND | ND | ND |

That which is claimed is:

1. The compound

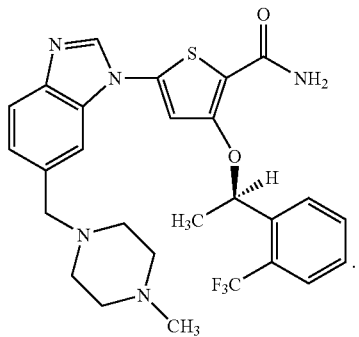

2. A pharmaceutically acceptable salt of the compound

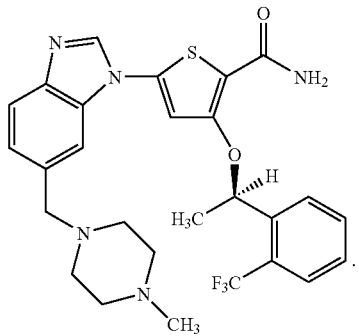

3. A pharmaceutical composition comprising the compound of claim 1, or a salt according to claim 2, and a pharmaceutically acceptable carrier, diluent, or excipient.

4. The pharmaceutical composition of claim 3 wherein said composition is enantiomerically enriched with the depicted R isomer relative to the corresponding S isomer.

5. The pharmaceutical composition of claim 4 wherein said composition comprises at least 90% by weight of the depicted R isomer relative to the corresponding S isomer.

6. A method of treating breast cancer, ovarian cancer, non-small cell lung cancer, prostate cancer, gastric cancer, carcinoma of the head and neck, or a hematologic malignancy in a human in need thereof, said method comprising administering to the human a therapeutically effective amount of a compound according to claim 1 or a salt according to claim 2.

7. A method for treating a susceptible neoplasm in a human in need thereof, said method comprising administering to the human a therapeutically effective amount of a compound according to claim 1 or a salt according to claim 2, wherein said susceptible neoplasm is selected from the group consisting of breast cancer, colon cancer, small cell lung cancer, non-small cell lung cancer, prostate cancer, endometrial cancer, gastric cancer, melanoma, ovarian cancer, pancreatic cancer, squamous cell carcinoma, carcinoma of the head and neck, esophageal carcinoma, hepatocellular carcinoma, and hematologic malignancies.

8. A method for treating breast cancer or ovarian cancer in a human in need thereof, said method comprising administering to the human a therapeutically effective amount of a compound according to claim 1 or a salt according to claim 2.

* * * * *